United States Patent
Paul et al.

(10) Patent No.: US 9,855,410 B2
(45) Date of Patent: Jan. 2, 2018

(54) OPTIC-BASED CONTACT SENSING ASSEMBLY AND SYSTEM

(75) Inventors: Saurav Paul, Minneapolis, MN (US); Troy T. Tegg, Elk River, MN (US); Reed R. Heimbecher, Hamel, MN (US); Richard E. Stehr, Stillwater, MN (US); Riki Chou Thao, Maplewood, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 637 days.

(21) Appl. No.: 13/143,001

(22) PCT Filed: Dec. 30, 2009

(86) PCT No.: PCT/US2009/069857
§ 371 (c)(1),
(2), (4) Date: Jun. 30, 2011

(87) PCT Pub. No.: WO2010/078453
PCT Pub. Date: Jul. 8, 2010

(65) Prior Publication Data
US 2011/0270046 A1 Nov. 3, 2011

Related U.S. Application Data

(63) Continuation-in-part of application No. 11/941,073, filed on Nov. 15, 2007, now Pat. No. 8,577,447.
(Continued)

(51) Int. Cl.
*A61B 6/00* (2006.01)
*A61M 39/10* (2006.01)
(Continued)

(52) U.S. Cl.
CPC .......... *A61M 39/10* (2013.01); *A61B 5/0084* (2013.01); *A61B 5/065* (2013.01); *A61B 5/1076* (2013.01);
(Continued)

(58) Field of Classification Search
CPC .......... A61B 18/24; A61B 2017/00057; A61B 2017/00084; A61B 2019/465
See application file for complete search history.

(56) References Cited

U.S. PATENT DOCUMENTS 4,757,194 A 7/1988 Simms
4,834,101 A 5/1989 Collison et al.
(Continued)

FOREIGN PATENT DOCUMENTS

EP 0900549 3/1999
EP 2062545 5/2009
(Continued)

OTHER PUBLICATIONS

"Fiber Optic Interferometer Fabry-Perot", http://physics.nad.ru/Physics/English/ifp_txt.htm, Oct. 15, 2007, 1-5.
(Continued)

*Primary Examiner* — James Kish
(74) *Attorney, Agent, or Firm* — Dykema Gossett PLLC

(57) ABSTRACT

A contact sensing assembly including a catheter and an electrode including a tip portion and a base portion, and a generally central axis, with the electrode being connected to a distal end of the catheter. Optical sensor(s) may be provided for emitting and/or receiving an optical signal, with a part of the optical signal being transverse to the central axis. Optical interference member(s) may be provided for interfering with the optical signal. A method for sensing contact force exerted by an electrode on a tissue includes directing an optical signal along a portion of a
(Continued)

catheter, emitting and/or receiving an optical signal, with a part of the optical signal being at a predetermined angle relative to the central axis, and sensing changes in intensity of the optical signal based on displacement associated with the electrode tip portion based on the contact force exerted by the electrode on the tissue.

30 Claims, 42 Drawing Sheets

Related U.S. Application Data

(60) Provisional application No. 61/142,079, filed on Dec. 31, 2008, provisional application No. 60/915,387, filed on May 1, 2007.

(51) Int. Cl.

| | | |
|---|---|---|
| *A61B 5/00* | (2006.01) | |
| *A61B 18/14* | (2006.01) | |
| *A61M 25/00* | (2006.01) | |
| *A61M 25/01* | (2006.01) | |
| *A61B 5/06* | (2006.01) | |
| *A61B 5/107* | (2006.01) | |
| *A61B 18/24* | (2006.01) | |
| *A61B 17/00* | (2006.01) | |
| *A61B 90/00* | (2016.01) | |

(52) U.S. Cl.
CPC .......... *A61B 5/6852* (2013.01); *A61B 5/6885* (2013.01); *A61B 18/1492* (2013.01); *A61M 25/0043* (2013.01); *A61M 25/0068* (2013.01); *A61M 25/0069* (2013.01); *A61M 25/0074* (2013.01); *A61M 25/01* (2013.01); *A61M 25/0138* (2013.01); *A61B 18/24* (2013.01); *A61B 2017/00057* (2013.01); *A61B 2017/00084* (2013.01); *A61B 2090/065* (2016.02); *A61M 25/007* (2013.01); *A61M 25/0071* (2013.01); *A61M 25/0141* (2013.01); *A61M 2025/0002* (2013.01)

(56) References Cited

U.S. PATENT DOCUMENTS

| | | | |
|---|---|---|---|
| 5,122,137 A | 6/1992 | Lennox et al. | |
| 5,413,107 A | 5/1995 | Oakley | |
| 5,460,182 A | 10/1995 | Goodman et al. | |
| 5,462,521 A * | 10/1995 | Brucker | A61B 18/1492 604/20 |
| 5,928,222 A | 7/1999 | Kleinerman | |
| 6,016,435 A * | 1/2000 | Maruo et al. | 600/316 |
| 6,113,590 A | 9/2000 | Fischer et al. | |
| 6,743,239 B1 | 6/2004 | Kuehn | |
| 7,060,965 B2 | 6/2006 | Vidovic et al. | |
| 8,048,063 B2 * | 11/2011 | Aeby et al. | 606/1 |
| 2002/0123749 A1 | 9/2002 | Jain | |
| 2004/0116992 A1 | 6/2004 | Wardle | |
| 2005/0245789 A1 | 11/2005 | Smith et al. | |
| 2007/0012094 A1 | 1/2007 | Degertekin et al. | |
| 2007/0060847 A1 | 3/2007 | Leo et al. | |
| 2007/0191829 A1 | 8/2007 | McGee et al. | |
| 2008/0009750 A1 * | 1/2008 | Aeby | A61B 5/042 600/478 |
| 2008/0294144 A1 | 11/2008 | Leo et al. | |
| 2009/0060977 A1 | 3/2009 | Lamson | |
| 2009/0093806 A1 | 4/2009 | Govari | |

FOREIGN PATENT DOCUMENTS

| | | |
|---|---|---|
| GB | 2189638 A | 10/1987 |
| GB | 2331580 | 5/1999 |
| WO | WO-2004/069072 | 8/2004 |
| WO | WO-2008/137303 | 11/2008 |

OTHER PUBLICATIONS

"General Pharmacology Samba—Blood Pressure Systems", http://www.bioseb.com/bioseb/anglais/default/item_id=94_cat_id=3_Samba%20-%20Pressure%20System.php, Oct. 2007, 1-4.

"International Search Report & Written Opinion", PCT/US2009/069857 dated Mar. 2010.

"Micro Pressure Measurement System—Product Overview", *Biopac Systems, Inc.*, Aug. 2007, 1-39.

"The Samba Technology", *Samba Sensors*: www.samba.se/index2.cfm?PageID=45, Oct. 2007.

Grace, Daniel, "High-Tech Partnership Bundles Catheters with Fiber-Optic Sensors", *Medical Product Manufacturing News*, Sep. 2007.

Peirs, J. et al., "Design of an Optical Force Sensor for Force Feedback during Minimally Invasive Robotic Surgery", *Katholieke Universiteit Leuven*, Leuven Belgium; www.mech.kuleuven.ac.be, 2003, 1-4.

"Supplementary European Search Report", EP 08746501 dated Jul. 2, 2012.

"Supplementary European Search Report", EP 09837175 dated Apr. 3, 2013.

International Search Report for PCT Application No. PCT/US2008/061092, dated Sep. 3, 2008. 1 pg.

Publications related to Samba Sensors AB, 3 pages. Publication date unknown.

* cited by examiner

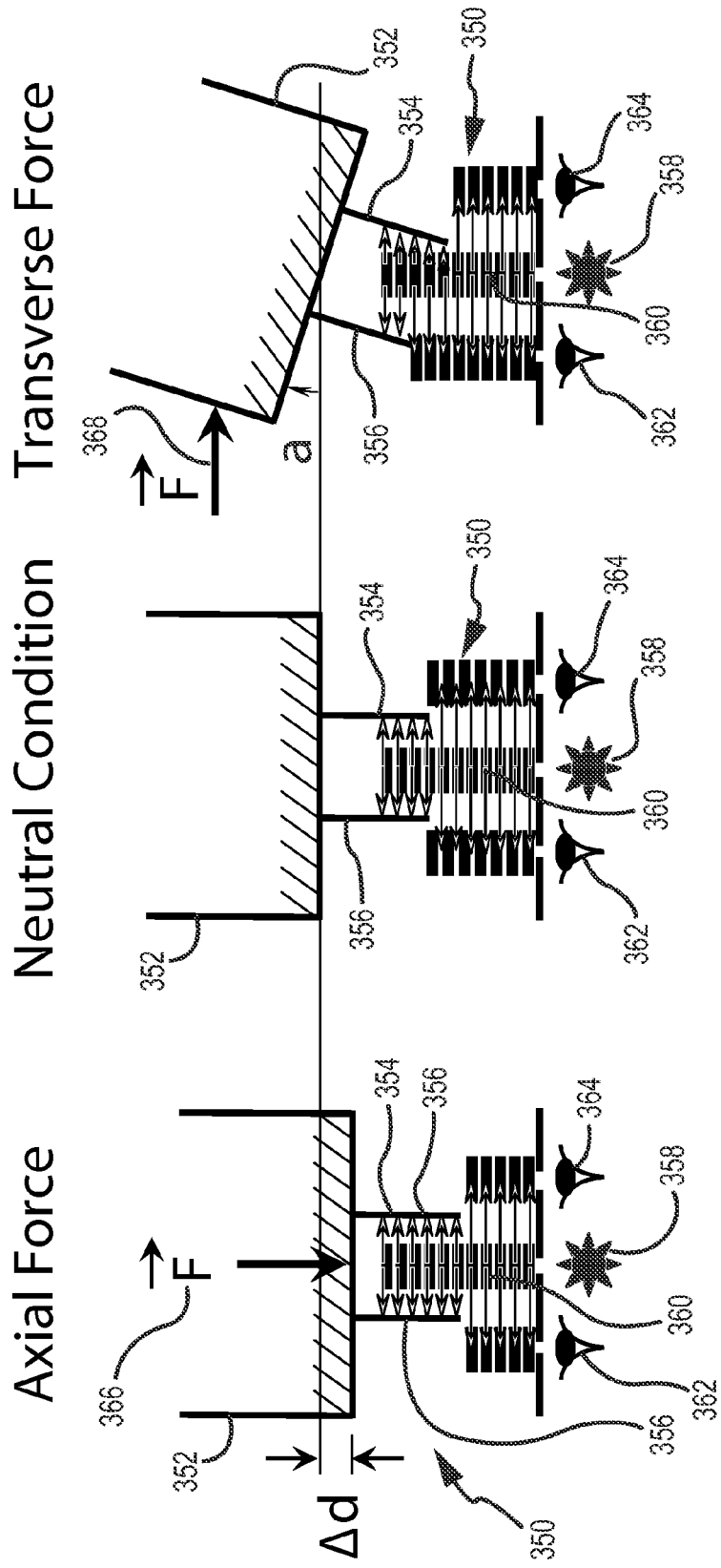

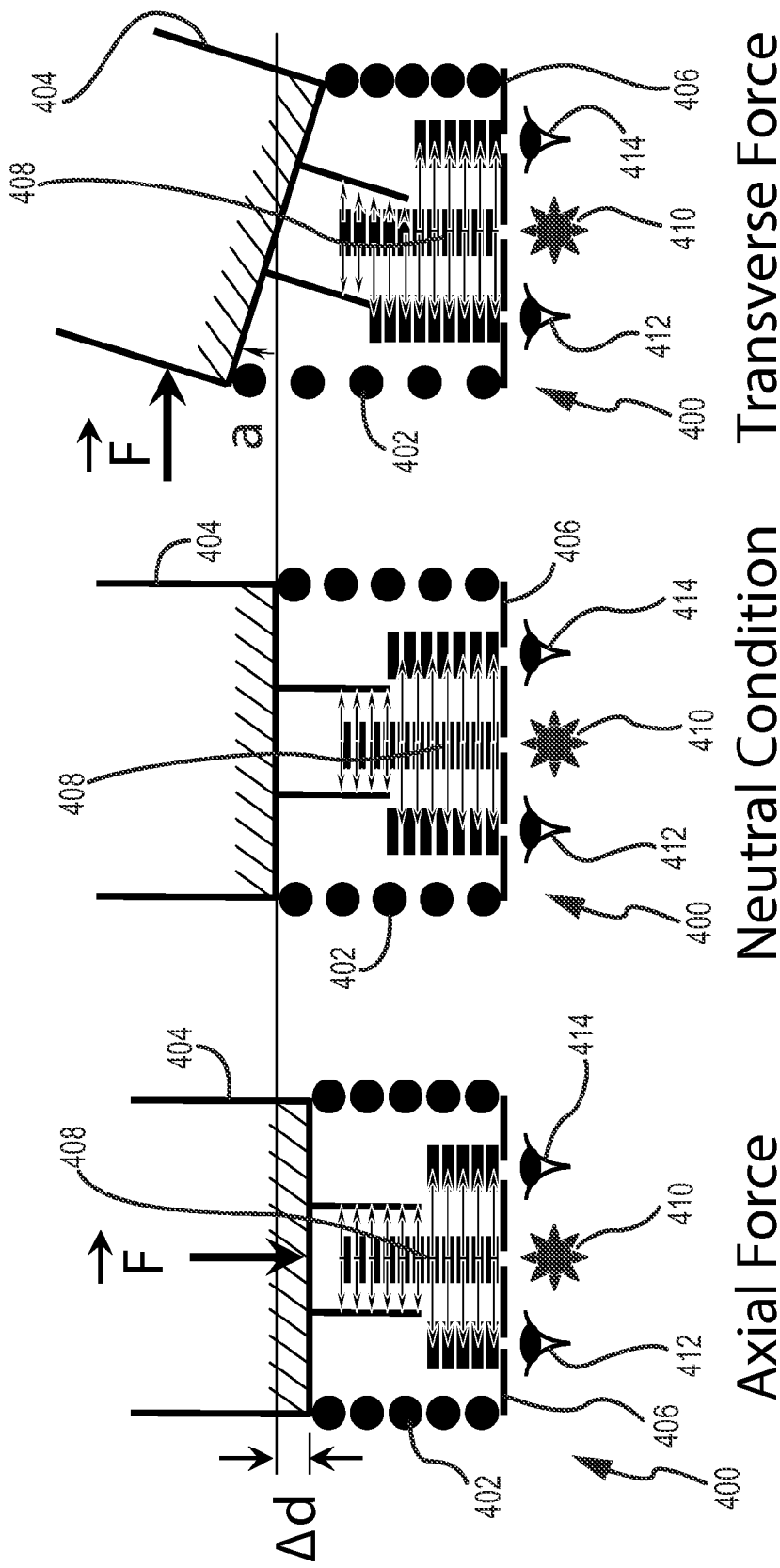

OPTIC-BASED CONTACT SENSING ASSEMBLY AND SYSTEM

CROSS-REFERENCE TO RELATED APPLICATIONS

This application claims priority to and the benefit of U.S. provisional application No. 61/142,079 filed 31 Dec. 2008 (the '079 application). For purposes of U.S. patent prosecution, this application is also a continuation-in-part of U.S. non-provisional application Ser. No. 11/941,073, filed 15 Nov. 2007 now U.S. Pat. No. 8,577,447 (the '073 application), which in turn claims the benefit of U.S. provisional application No. 60/915,387, filed 1 May 2007 (the '387 application). The entire contents of each of the '079, the '073, and the '387 applications are hereby incorporated by reference as though fully set forth herein.

BACKGROUND OF THE INVENTION a. Field of the Invention

The instant invention relates to an optic-based sensing assembly. The instant invention includes an optic-based catheter assembly and related system used to monitor or determine contact between a catheter and the surrounding proximate environment, such as tissue. Such a system may be used for visualization, mapping, ablation, and/or other methods of diagnosis and treatment of tissue. The instant invention also relates to a method for sensing and calculating contact force exerted by an electrode on a tissue.

b. Background Art

The visualization and treatment of organs and tissues has been advanced through the increasing use of catheter systems. Catheter systems have been designed for the incorporation of various components to treat and diagnose ailments, as accomplished through the mapping of organs, sensing of thermal and electrical changes exhibited by a tissue (e.g., heart), as well as the application of energizing sources (such as radiofrequency (RF), cryogenics, laser, and high frequency ultrasound) to tissue. Moreover, catheter systems may be further modified to include irrigation channels that enable cooling of the electrode tip during ablation procedures.

Catheter systems generally include a portion that contacts the tissue or organ, or is inserted in an environment (e.g., heart chamber or vessel) to detect a number of parameters, such as for example, location of the tissue, contact or pressure exerted on the tissue, electrophysiological attributes of the tissue, or other type of parameters that aid in the evaluation or treatment of the organ or tissue.

It is known that sufficient contact between a catheter, in particular an electrode provided in connection with a catheter, and tissue during a procedure is generally necessary to ensure that the procedure is effective and safe. Current techniques of mapping, visualization and treatment using energizing sources, such as the use of radiofrequency energy during ablation, rely on placing of the electrode of a catheter system in consistent mechanical contact with targeted tissue. Perforation of the cardiac wall as well as lesion formation (such as lesions created by exposure to radiofrequency) partially depends upon the direction of contact between the electrode and tissue. In particular, for endocardial catheter applications, the point of electrode-tissue contact is typically 150 cm away from the point of application of force applied by the operator (whether manual or automated) of the catheter outside of the body. Coupled with the fact that a beating heart has dynamically moving walls, this gives rise to some functional and theoretical challenges such as ensuring that the electrode is in sufficiently constant mechanical contact with the myocardial wall.

Catheter systems having sensor assemblies, such as those mounted on the catheter shaft proximal to the electrode or remotely in the handle set, leave the possibility, however small, of obtaining false positive outcomes when detecting contact between the electrode and the tissue. False positive outcomes may occur, for example, when a nonconductive portion of the catheter wall, and not the electrode, is in contact with the tissue. Such condition may arise during the catheter manipulation in the heart when, for instance, the distal portion of the catheter is curled inward so much as to lose electrode contact with the tissue, while the distal portion of the catheter is in contact with the tissue. When that happens, remotely placed sensors can generate signals due to the deflection of the catheter shaft, thereby falsely indicating contact between the electrode and tissue. Accordingly, optic-based contact sensors coupled to the electrode can, among other things, help reduce the possibility of obtaining false positive outcomes when detecting contact between the electrode and the tissue.

As previously suggested, there are a number of methods used for ablation of desired areas, including, for example, radio frequency (RF) ablation. RF ablation is accomplished by transmission of radio frequency energy to a desired target area through an electrode assembly to ablate tissue at the target site. Because RF ablation may generate significant heat, which if not controlled can result in undesired or excessive tissue damage, such as steam pop, tissue pop, and the like, it is commonly desirable to include a mechanism to irrigate the target area and the device with biocompatible fluids, such as a saline solution. The use of irrigated ablation catheters can also prevent the formation of soft thrombus and/or blood coagulation.

Irrigated catheters may be used to ensure an increase in ablation efficiency, while at the same time increasing the cooling efficiency of the electrode. Moreover, irrigated ablation electrodes may be used to further enhance the performance of the catheter system. Nonetheless, in the use of an irrigated catheter in endocardial ablation applications, there remains the continued challenge in ensuring the directionality of the irrigation such that the irrigation ablation portion of the electrode faces the tissue.

BRIEF SUMMARY OF INVENTION

For some applications, it is desirable to have an optic-based catheter system that includes an optical sensor that detects changes in reflected energy, such as light, from an optically interactive surface provided by an electrode. It is also desirable to provide a system which is insensitive to an RF field, electromagnetic interference (EMI), and thermal effects. Furthermore, it is also desirable to have a system which seeks to minimize false positives, is robust in construction and has a wide dynamic range. In an embodiment, the electrode may be subjected to a compressive force due to mechanical contact of the electrode surface with another body or surface. The optical sensor of the invention can be used to measure contact of an electrode with a dynamically moving wall, such as a beating heart.

In another embodiment, a contact sensing assembly for sensing contact with a target (e.g., a tissue or other organ surface) is provided. The assembly may include an elongated body having a distal section and a sensor connected to the distal section. The sensor may include a segment with a first interactive component, a tip positioned distally from the segment, and a flexible coupling member separating the segment from the tip. The tip may include an external surface and is positioned distally from the segment, the tip further including a second interactive component that is adapted to interact with the first interactive component. The flexible coupling member may separate the segment from the tip, such that the second interactive component can move relative to the first interactive component when the external surface of the tip contacts the target.

In another embodiment, a contact sensing assembly may include a catheter including a body having a proximal end and a distal end, and an electrode including a tip portion and a base portion, and a generally central axis, with a portion of the electrode being connected to the distal end of the catheter. One or more optical sensors may be provided for emitting and/or receiving an optical signal, with a part of the optical signal being transverse to the central axis. The optical sensor may be operatively connected to the electrode or the catheter body. One or more optical interference members may be operatively connected to the electrode or the catheter body for interfering with the optical signal.

In another embodiment, an irrigated contact sensing assembly may include a catheter including a body having a proximal end and a distal end, and an electrode including a tip portion and a base portion, wherein a plurality of irrigation ports are positioned on the tip portion of the electrode. Moreover, the tip portion of the electrode may be configured with a predefined length, such that the irrigation ports are disposed along the length of the tip portion of the electrode. The irrigation ports may be provided in various numbers, shapes, sizes and orientations to provide a irrigated catheter. The irrigation ports may be adapted to transport cooling fluid from a lumen to the surface of the electrode.

For the contact sensing assembly described above, in an embodiment, the optical sensor may be configured to send and receive light energy or a light-based signal. In an embodiment, the distal end of the catheter may include a coupling member having a neck portion. The neck portion of the coupling member, in an embodiment, may move relative to an external force exerted on the electrode. In an embodiment, the neck portion of the coupling member may include a twist, torsion bar, alpha, dove-tail or spring shaped elastic portion for enabling external axial and transverse forces and torques exerted on the electrode to be sensed by the optical sensor. The coupling member, in an embodiment, may include a mounting shaft that defines an internal recessed groove for receiving at least a portion of the optical sensor. In an embodiment, the tip portion of the electrode may include an irrigation port. The electrode, in an embodiment, may include a lumen provided within an internal cavity of the electrode, with the lumen being positioned adjacent to the base and tip portions of the electrode.

For the contact sensing assembly described above, in an embodiment, the optical sensor may include an emitter and a receiver for respectively emitting and receiving the optical signal. The emitter and receiver, in an embodiment, may be provided with a single optic fiber. In an embodiment, the emitter and/or receiver may be positioned to respectively emit or receive the optical signal, a part of which may be substantially parallel to the central axis. In an embodiment, a reflective surface may be provided for altering an angle of the optical signal substantially towards the optical interference member. The reflective surface may be disposed on the emitter or on a fiber mirror arrangement. The emitter and/or receiver, in an embodiment, may be positioned to respectively emit or receive the optical signal, with the optical signal being substantially transverse to the central axis.

For the contact sensing assembly described above, in an embodiment, the optical sensor may include one or more emitters and radially positioned receivers for respectively emitting and receiving the optical signal. In an embodiment, at least a part of the optical signal may be substantially parallel to the central axis. The distal end of the catheter, in an embodiment, may include a coupling member having an elastic neck portion. In an embodiment, the optical signal may be substantially transverse to the central axis. In an embodiment, the emitter and receiver may be provided with a single optic fiber. The optical interference member, in an embodiment, may be an appendage formed on the electrode base portion, and the single optic fiber may be disposed radially outboard of the appendage relative to the central axis. In an embodiment, the optical interference member may be an appendage formed on the electrode base portion, with the single optic fiber disposed radially inboard of the appendage relative to the central axis.

For the contact sensing assembly described above, in an embodiment, the optical interference member may be a structure formed on the electrode base portion or the catheter distal end (or both). In an embodiment, the optical interference member may be an appendage formed on the electrode base portion. The appendage, in an embodiment, may include a cutout for allowing passage of a predetermined amount of the optical signal.

For the contact sensing assembly described above, in an embodiment, the optical interference member may be configured to interfere with the optical signal by respectively first and second predetermined amounts related to first and second predetermined positions of the electrode relative to the catheter body. In an embodiment, the first predetermined amount of optical signal interference may be zero interference. Alternatively, the first predetermined amount of optical signal interference may be greater then zero interference. In an embodiment, the optical sensor may include a fiber optic cable including one or more lumens, and a peripheral wall surrounding the lumen, with the optical sensor connected to the peripheral wall. A plurality of optical sensors, in an embodiment, may be disposed within the body of the catheter, with each optical sensor having a means for emitting and receiving light energy. In an embodiment, the optical sensors may be circumferentially disposed within the body of the catheter. The optical sensor, in an embodiment, may include an emitter and a receiver for respectively emitting and receiving the optical signal, with the emitter and receiver being adjacent to one another and being paired. In an embodiment, the optical sensor may include an emitter and a receiver for respectively emitting and receiving the optical signal, with a plurality of emitters and a plurality of receivers being distributed about a peripheral wall of a fiber optic cable such that each emitter operatively interacts with one or more receivers.

For the contact sensing assembly described above, in an embodiment, a lumen may be disposed within the body of the catheter, with at least a portion of the lumen extending into the electrode for slidably receiving one or more sensing components. In an embodiment, a lumen may be disposed within the body of the catheter, with at least a portion of the lumen extending into the electrode for slidably receiving one or more energizing components. The energizing component may be a radiofrequency current, direct current, high-intensity ultrasound, laser, cryogenic, and combinations thereof. In an embodiment, the tip portion of the electrode may include a portion configured to perform ablation. The optical sensor, in an embodiment, may be adapted to measure a parameter, such as, intensity, wavelength, phase, spectrum, speed, optical path, interference, transmission, absorption, reflection, refraction, diffraction, polarization, and/or scattering.

In another embodiment, a lumen may be disposed within the body of the catheter and extending into the electrode, in particular, the tip portion of the electrode. The lumen may be provided to allow fluid to flow within the catheter to the electrode, thereby enabling irrigation of the electrode and surrounding tissue once contact is determined by the feedback from the optical sensors of the catheter system.

In another embodiment, an optical-based catheter system may include a catheter including a body having a proximal end and a distal end. An electrode may include a tip portion and a base portion, and a generally central axis, with a portion of the electrode being connected to the distal end of the catheter. One or more optical sensors may be provided for emitting and/or receiving an optical signal, with at least a part of the optical signal being transverse to the central axis, and the optical sensor being operatively connected to one of the electrode and the catheter body. One or more optical interference members may be operatively connected to the electrode or the catheter body (or both) for interfering with the optical signal. The system may further include a light energy source, a processor, and a catheter mapping unit for use in mapping or visualizing the catheter location.

For the system described above, in an embodiment, the system may determine a displacement associated with the electrode tip portion using sensed changes in intensity of the optical signal. The optical sensor may be adapted to measure a parameter, such as, intensity, wavelength, phase, spectrum, speed, optical path, interference, transmission, absorption, reflection, refraction, diffraction, polarization, and/or scattering.

In another embodiment, a method for sensing contact force exerted by an electrode on a tissue may include directing an optical signal along at least a portion of a tubular body of a catheter having a proximal end and a distal end, and connecting an electrode including a tip portion and a base portion to the distal end of the catheter. The method may further include emitting and/or receiving an optical signal, with at least a part of the optical signal being at a predetermined angle relative to the central axis, and sensing changes in intensity of the optical signal responsive to displacement associated with the electrode tip portion based on the contact force exerted by the electrode on the tissue.

For the method described above, in an embodiment, the predetermined angle may be approximately 0°. In an embodiment, alternatively, the predetermined angle may be greater than approximately 0°. In an embodiment, the method may further include determining corresponding contact force vectors between the electrode and the tissue in contact with the electrode by evaluating the sensed changes in intensity. The contact force vectors, in an embodiment, may include an axial component of the contact force and a transverse component of the contact force. The method, in an embodiment, may further include calibrating an optical sensor that emits and receives the optical signal.

For the method described above, in an embodiment, the method may include calibrating a plurality of optical sensors that emit and receive respective optical signals. In an embodiment, the method may further include calibrating the optical sensors by measuring an intensity of the respective optical signal for each optical sensor at zero-force ($I_{0x}$), measuring an intensity of the respective optical signal for each optical sensor at a force greater than zero ($I_x$), and determining the relative intensity ($I_{rx}$) between $I_x$ and $I_{0x}$ for each optical sensor as follows: $I_{rx}=I_x-I_{0x}$. The method may, in an embodiment, include determining the axial and transverse components of contact force as a function of an angle of attack of the electrode relative to the tissue. In an embodiment, the method may include determining regression curves for the axial and transverse components of the contact force for a predetermined contact force range.

For the method described above, in an embodiment, the method may further include using the calibrated optical sensor(s) to determine the axial and transverse components of the contact force. In an embodiment, the method may further include determining the contact force magnitude as a function of the axial and transverse components of the contact force. The method may, in an embodiment, include determining an angle of attack of the electrode relative to the tissue as a function of the axial and transverse components of the contact force. In an embodiment, the method may include determining an angle of rotation of the electrode relative to the tissue as a function of the change in intensity and phase angle of the optical sensor.

For the method described above, in an embodiment, the electrode may perform RF ablation, HIFU ablation, laser ablation, cryo ablation, ultrasonic imaging, electrical pacing, EP pacing, electrical sensing, and/or EP sensing. In an embodiment, the sensed contact force may be utilized for automatically limiting a maximum contact force, warning of a high or unacceptable contact force, giving visual or audible feedback to a practitioner regarding a tissue contact force, warning of a loss of contact force or contact, and/or warning of a contact force which may be too low.

In another embodiment, a method of manufacturing an optical sensing assembly, in accordance with the present invention, may further include providing an optical sensor having a proximal end and distal end, including an emitter and a receiver, each having a distal end and a proximal end, for respectively emitting and receiving an optical signal. The method further includes advancing the distal end of the optical sensor towards a proximal end of an electrode. The method includes retracting the optical sensor from the proximal end of the electrode to dispose the distal end portion of the optical sensor within a base portion of the electrode. Moreover, the method includes coupling the proximal end of the optical sensor to an amplifier, and positioning the optical sensor within the base portion of the electrode by utilizing optical signals processed by the amplifier. The method further includes securing the optical sensor relative to the base portion of the electrode.

The foregoing and other aspects, features, details, utilities, and advantages of the invention will be apparent from reading the following description and claims, and from reviewing the accompanying drawings.

BRIEF DESCRIPTION OF THE DRAWINGS

FIGS. 17A-17C, 18A-18C, and 19-23 are each respectively exemplary views of embodiments of transverse transmission based contact sensing assemblies according to the invention.

DETAILED DESCRIPTION OF THE INVENTION

Figure 1:
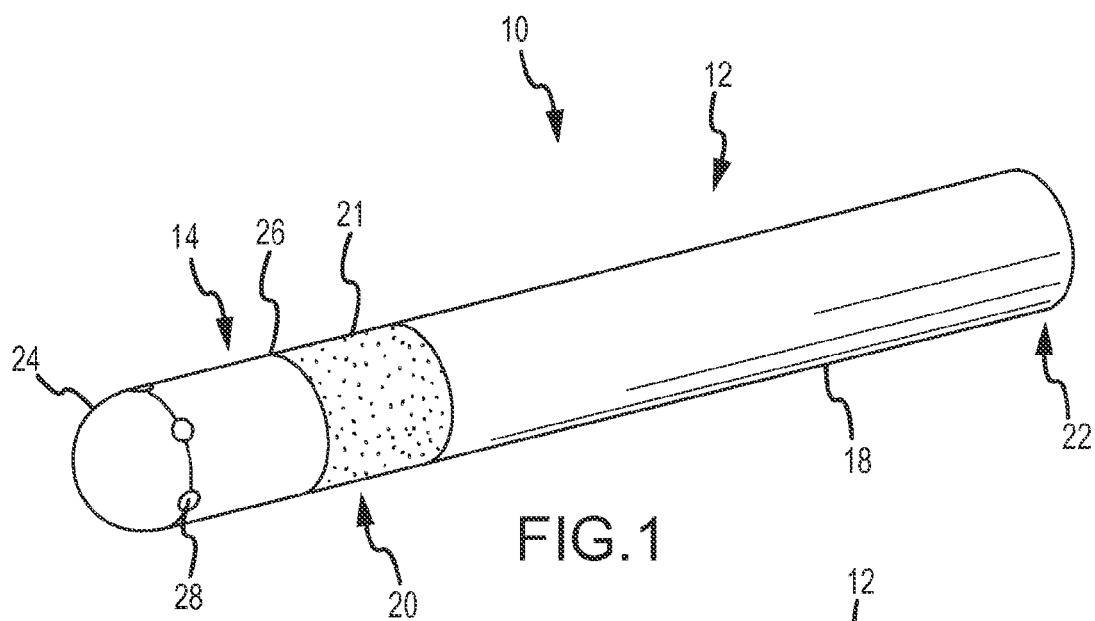
FIG. 1 is a partial isometric view of a catheter assembly in accordance with an embodiment of the invention.
Figure 2:
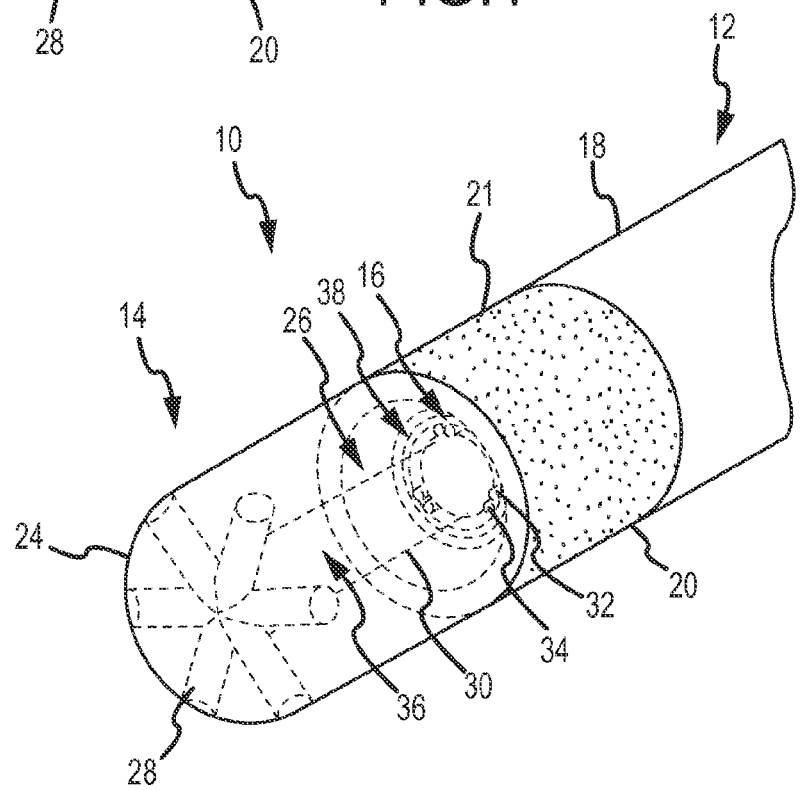
FIG. 2 is an enlarged partial isometric view of the catheter assembly shown in FIG. 1, wherein the electrode and portion of the optic-based sensing assembly is shown in phantom.

Referring now to the drawings wherein like reference numerals are used to identify like components in the various views, FIGS. 1 and 2 illustrate an exemplary embodiment of a contact sensing assembly 10 (also referred to as a catheter assembly) as provided by the invention. In a general form, the contact sensing assembly 10 includes a catheter shaft 12, an electrode 14 connected to the catheter shaft, and an optical sensor 16 for optically interacting with a portion of electrode 14.

The contact sensing assembly 10 may be used in the diagnosis, visualization, and/or treatment of tissue (such as endocardial tissue) in a body. Contact sensing assembly 10 may be used in a number of diagnostic and therapeutic applications, such as for example, the recording of electrograms in the heart, the performance of cardiac ablation procedures, and/or various other applications. The assembly may be used in connection with a number of applications that involve humans, or other mammals, for tissue observation, treatment, repair, or other procedures. Moreover, the invention is not limited to one particular application, but rather may be employed by those of ordinary skill in the art in any number of diagnostic and therapeutic applications. Throughout the disclosure, various embodiments of assembly 10 are disclosed, including alternate embodiments of catheter shaft 12, electrode 14, and optical sensor 16. Each of the components of the assemblies may be used interchangeably, as recognized by one of ordinary skill in the art.

The catheter shaft 12 of the assembly includes a body 18 having a distal end 20 and a proximal end 22. The body 18 of the catheter shaft 12 is generally tubular in shape, although other configurations of the catheter shaft may be used as known in the industry. The distal end 20 of catheter shaft 12 is connected to the electrode 14. The body 18 of shaft 12 may house the optical sensor 16, as well as other components used in the diagnosis and/or treatment of tissue. If desired, the outer portion of the catheter shaft 12 may have a braided outer covering thereby providing better torque transfer, and increased flexibility and strength. The catheters of the invention vary in length and are attached to a handle, handle assembly or any other type of control member that allows a surgeon, an electrophysiologist, or any other type of operator of the catheter assembly to manipulate the relative position of the assembly within the body from a remote location, as recognized by one of ordinary skill in the art. This type of manipulation and/or movement may be accomplished either manually (i.e., by a surgeon) or automatically (i.e., through the use of a robotically operated device).

In accordance with an embodiment of the assembly, as reflected in FIG. 1, the distal end 20 of the catheter shaft 12 includes at least a portion or segment 21 that exhibits increased flexibility relative to more proximal portions of the catheter shaft 12. The increased flexibility of at least the portion or segment 21 associated with the distal end 20 may be achieved through any number of methods, including but not limited to, the use of flexible materials, the formation of a spring-like coupling portion (as further discussed in more detail below), or any other type of connection that allows for increased flexibility at the portion or segment 21 of the distal end 20 of the catheter shaft 12. In an alternate embodiment, segment 21 may further include a compliant protective covering disposed around a coupling (as discussed in more detail below) to ensure that fluids do not enter the assembly and interfere with the operation of the assembly. The exertion of external contact force on the outer surface of the electrode 14, results in at least the portion 21 of the distal end 20 of the catheter shaft 12 flexing and/or bending relative to the electrode 14. The relative movement (e.g., displacement either axially, laterally, or a combination thereof) of the distal end 20 may be proportionate or correlated to the force exerted on electrode 14.

The electrode 14 includes a tip portion 24 and a base portion 26. In one embodiment, electrode 14 may be configured to include a means for irrigating. For example, without limitation, at least one irrigation port 28 may be incorporated within or through the electrode 14, thereby providing an irrigated electrode tip. An irrigated electrode tip allows for the cooling of the electrode 14, for instance, through the transporting of fluid through the electrode 14 and around the surface of the tissue. A number of different types of electrodes, irrigated and non-irrigated, may be connected and incorporated for use as the electrode 14 according to embodiments of the invention depending on the type of procedures being performed. Such irrigated electrodes include, but are not limited to, those disclosed in U.S. patent application Ser. No. 11/434,220 (filed 16 May 2006), Ser. No. 10/595,608 (filed 28 Apr. 2006), and Ser. No.11/646,270 (filed 28 Dec. 2006) Ser. No.11/647,346 (filed 29 Dec. 2006), and international patent application no. PCT/US2007/080920 (filed 10 Oct. 2007), each of which is hereby incorporated by reference as though fully set forth herein.

The electrode 14 may further include an optically interactive surface 30, 30' (see, e.g., FIGS. 2 and 5B), described further below, that may be provided in connection with a portion of the electrode 14 that interacts with the optical sensor 16 of the assembly 10. As shown in FIG. 2, the electrode 14 may further include an electrode cavity 36, as shown in phantom. The electrode cavity 36 may be used to house a number of different components and/or functions in connection with the electrode. In an embodiment, electrode cavity 36 may include the optically interactive surface 30 (see FIG. 2) that is designed to interact with the components of the optical sensor 16, such as a receiver 32 and an emitter 34. In alternate embodiments, the electrode cavity 36 may serve as a lumen for transferring components and/or materials, such as for example, irrigation fluid to at least one irrigation port 28, electrical components, or any other type assembly components that need to be transferred and/or disposed within the electrode 14.

As stated, the optically interactive surface 30 may be provided on or in connection with a surface associated with electrode 14. The relative position of the interactive surface 30 (which has a known position with respect to the electrode) allows sufficient interaction and/or functional communication with the optical sensor 16 such that a change in the communication (e.g., optical signal, light intensity) can provide a means for determining the contact force and/or orientation of the electrode with the tissue or surrounding area. In one embodiment, the electrode cavity 36 includes the optically interactive surface 30 (see, e.g., FIG. 2). In an alternate embodiment, the optically interactive surface 30' may be provided on or in connection with the base portion 26' of electrode 14' (see, e.g., FIG. 5B). The optically interactive surface may be comprised of any material suitable for the intended environment that reflects or refracts light energy. For example, without limitation, the interactive surface may comprise a reflective metal, such as a polished metal. Collectively, the interactive surface 30, 30' may also comprise prisms or other refractive media which may further include a reflective surface. Depending on the design of the optically interactive surface 30, 30', the surface may further include a mirrored surface, filters positioned relative to surface and/or other types of refractive media in combination with opaque segments, as discussed in more detail below.

The optical sensor 16 may be positioned within the distal end 20 of the catheter shaft 12. The optical sensor 16 may include at least one optic fiber that transmits and receives an optical signal, such as light energy. The optical sensor may also be manufactured to transmit and/or receive various types of signals including those associated with electromagnetic radiation, lasers, x-rays, radiofrequency, etc. In an embodiment, the optical sensor 16 may use light energy to determine the relative contact (e.g., force, stress, and/or orientation) between electrode 14 and an external surface in operational contact with the outer surface of the electrode— for example, tissues and surrounding environments, including organs, heart chambers, and the interior of vessels. Moreover, the optical sensor may be adapted to measure one or more parameters, including, for example, intensity, wavelength, phase, spectrum, speed, optical path, interference, transmission, absorption, reflection, refraction, diffraction, polarization, and scattering.

In an embodiment, one or more force vectors may be used to determine the contact force and/or orientation of the electrode in connection with the surrounding tissue or other external surfaces. In particular, the change of intensity of the optical signal received by at least one of the optical sensor 16 may be correlated to the contact force exerted on electrode 14 by an external surface. The intensity of the optical signals received by optical sensor 16 is proportional to the structural displacement of the distal end 20 of the catheter shaft 12. As discussed in more detail below, the displacement of the distal end 20 is governed by a factor (k) (such as a spring constant) exhibited by the material comprising the portion 21 of distal end 20. Accordingly, the factor (k) may be equated to the external force (F), either laterally or axially, exerted on electrode 14, divided by the unit displacement (d) (either axially or laterally) of electrode, which may be generally expressed as $k=F/d$. Since the change in intensity of the optical signals is proportional to the displacement of the electrode, the external force exerted on the electrode may be determined.

Figure 3A:
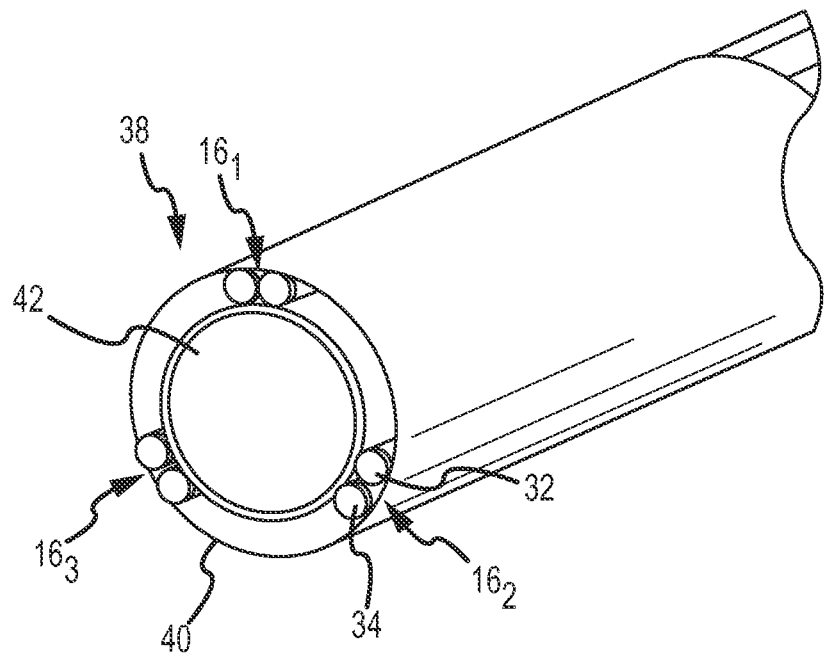
FIGS. 3A and 3B are partial isometric views of portions of an optic-based sensing assembly according to alternative embodiments of the invention.
Figure 3B:
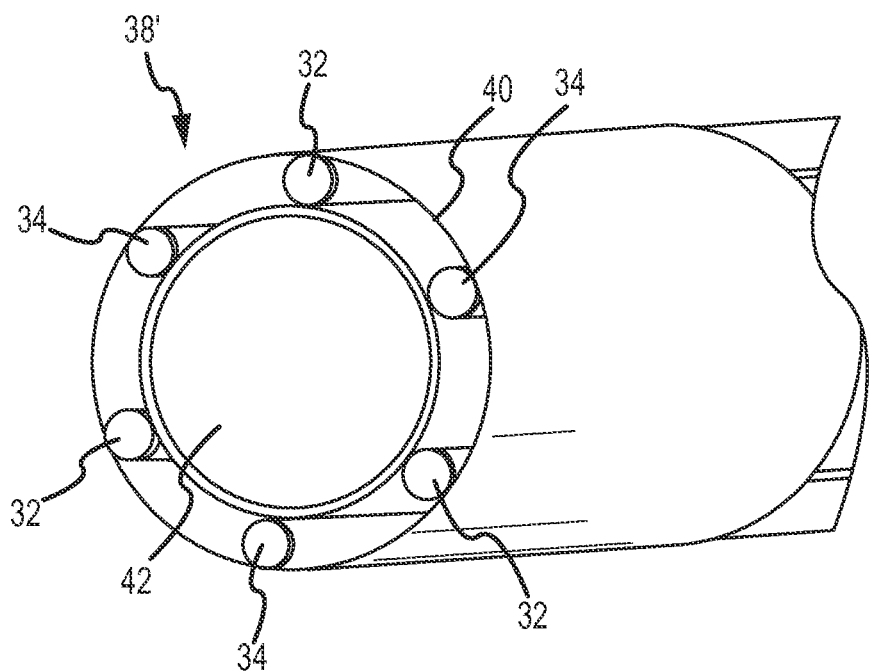

In order to determine light or optical intensity, optical sensor 16 may include at least one receiver 32 and at least one emitter 34 for receiving and emitting light energy, respectively. The receiver 32 and the emitter 34 may be included in a single fiber optic cable or in two separate fiber optic cables, as shown in FIG. 2. A number of the optical sensors 16 may be arranged within the distal end 20 of the catheter shaft 12 to operatively (e.g., optically) interact with the interactive surface 30 that is provided in connection with electrode 14. Moreover, a number of the receivers 32 and the emitters 34 may be disposed within the distal end 20 of the catheter shaft 12 in various configurations and combinations to assess contact and/or orientation readings. Such positioning and combinations can be configured and/or adapted to optimize their operation for an intended application or environment. For example, without limitation, as shown in FIGS. 3A and 3B an equal number of emitters and receivers may be provided in various configurations. In alternate embodiments, an unequal number of emitters and receivers may be provided in various combinations.

Referring to FIGS. 2-3B, various embodiments having alternate configurations of the optical sensors 16 are illustrated in connection with the catheter shaft 12. Each of the optical sensors 16 may further includes a receiver 32 and an emitter 34. In the illustrated embodiments, the optical sensors 16 comprise part of a fiber optic cable 38, 38'. As shown in, for example, FIGS. 3A and 3B, the fiber optic cable 38, 38' may comprise at least one optical sensor 16 captured between a peripheral wall 40 and an internal, tubular wall (not numbered) that forms a lumen 42. In this configuration, the optical sensors 16 are connected to the peripheral wall 40 surrounding the lumen 42. As shown, for example in FIG. 2, the fiber optic cable 38 is disposed within the body 18 of the catheter shaft 12. The lumen 42 may further be provided to carry various components, such as for example, thermal sensors, electrical components, or any other components known by one of ordinary skill in the art for incorporation within a catheter assembly. Alternately, the lumen 42 may be configured to provide a passageway for fluids, such as those needed for an irrigated electrode. FIG. 3A further illustrates three optical sensors $16_1$, $16_2$, and $16_3$ connected to the peripheral wall 40 in a paired configuration wherein the receiver 32 and the emitter 34 are provided adjacent to one another. Each of the optical sensors $16_1$, $16_2$, and $16_3$ may be positioned relative to one another circumferentially around the peripheral wall 40 adjacent to the lumen 42. In a particular embodiment, as generally shown in FIG. 3A, the optical sensors $16_1$, $16_2$, and $16_3$ may be provided in the paired configuration, wherein the pairs are separated about the peripheral wall 40 of the fiber optic cable 38. Each of the pairs may be separated by various degrees, such as 120 degrees, as shown. Alternatively, FIG. 3B illustrates an embodiment wherein a plurality of the receivers 32 and the emitters 34 are circumferentially disposed along the peripheral wall 40 and spaced from one another. The receivers 32 and the emitters 34 may be provided in various combinations, ratios, and relative positions to one another depending on the design of the sensing assembly 10.

FIGS. 4, 5, 6A, 6B and FIG. 7 illustrate various alternate embodiments of a contact sensing assembly 10' and 10". As previously suggested, each of the assemblies 10' and 10" include catheter shaft 12' coupled with alternate configurations of electrode 14' and 14". Collectively, the assemblies may further include a coupling member 50 for receiving a portion of electrode 14' and 14" for connection with a distal end 20' of the catheter shaft 12'. For all purposes, electrodes 14, 14', and 14" may be used interchangeably with the various embodiments of the disclosure.

Figure 4:
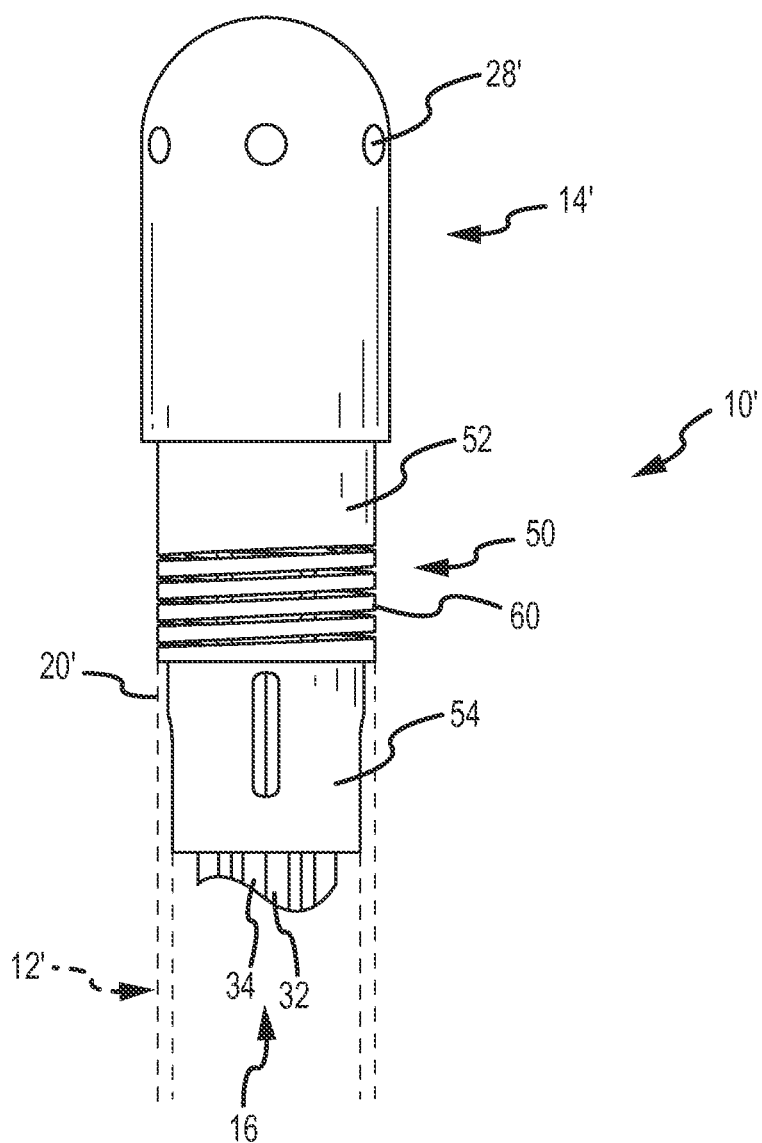
FIG. 4 is a side elevation view of an alternate embodiment of the invention.

In particular, FIG. 4 illustrates an electrode 14' connected to the coupling member 50. The coupling member 50 includes a neck portion 52 for receiving a portion of electrode 14' and a mounting shaft 54 which is received by the catheter shaft 12' (shown in phantom). The coupling member 50 further includes an elastic portion 60 disposed between neck portion 52 and mounting shaft 54. The elastic portion 60 facilitates the relative movement of the electrode to the mounting shaft 54 connected to catheter shaft 12'.

Figure 5A:
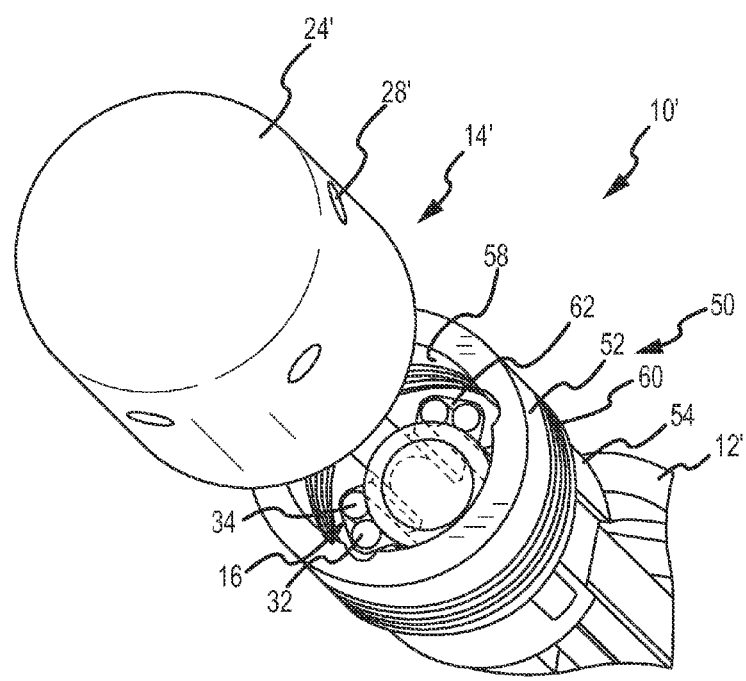
FIGS. 5A and 5B are exploded isometric views of an assembly of the type shown in FIG. 4.
Figure 5B:
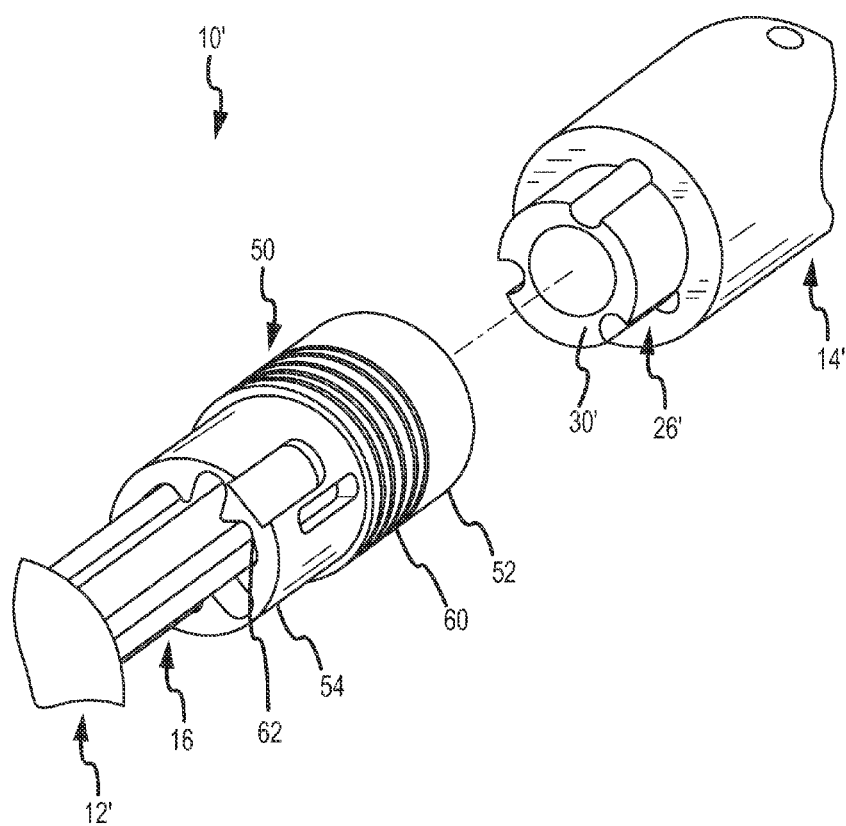

As further exemplified in the combination of FIGS. 5A and 5B, the neck portion 52 of the coupling member 50 may define a receptacle or receiving portion 58 for receiving a portion of the electrode 14' for connection with the catheter shaft 12'. In particular, the base portion 26', as seen in FIG. 5B, of the electrode 14' may be received by the electrode receptacle or receiving portion 58 for connecting the electrode 14' to coupling member 50. Neck portion 52 includes elastic portion 60 that provides increased flexibility. The elastic portion 60 may be configured to include a number of alternate embodiments, such as a spring. The elastic portion 60 of neck portion 52 facilitates relative movement between the tip portion 24' of the electrode 14' and the mounting shaft 54. In most embodiments, mounting shaft 54 is more rigid than neck portion 52 of coupling member 50 and provides secure engagement with the catheter shaft 12'. At least one pull wire (not shown) may be attached to mounting shaft 54 for movement and deflection of the distal portion of the catheter shaft 12'.

The mounting shaft 54 may further include at least one recessed groove 62 for receiving and mounting optical sensor 16. The recessed groove 62 may position optical sensor 16 so that the distal end of the optical sensor 16 is flush with the distal surface of the mounting shaft 54 (see, e.g., FIG. 5A). Alternate embodiments may provide for optical sensors that extend into the electrode. Overall, the optical sensors are positioned to interact with the optically interactive surface 30, 30' as provided by electrode 14, 14'. FIG. 5B provides an embodiment, wherein the optically interactive surface 30' is provided on or is a part of the base portion 26' of the electrode 14'. The optically interactive surface 30, 30' may, in another embodiment, be provided as a coating on or a formed surface in connection with the electrode 14, 14'.

Figure 6A:
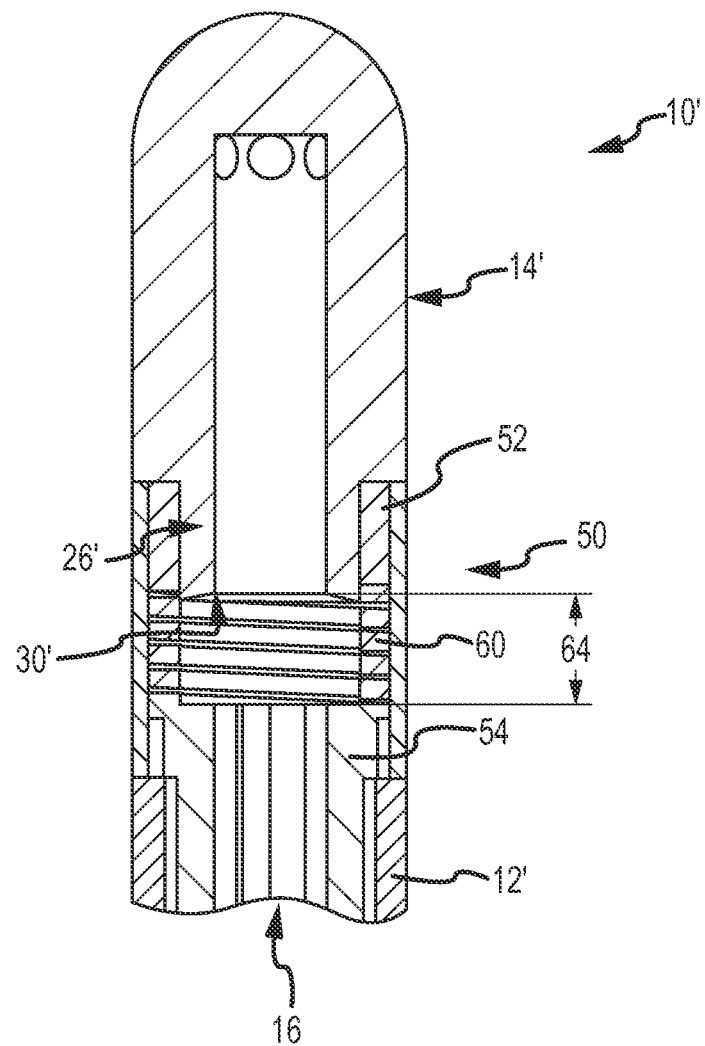
FIGS. 6A and 6B are side cross-sectional views of an assembly of the type shown in FIG. 4.
Figure 6B:
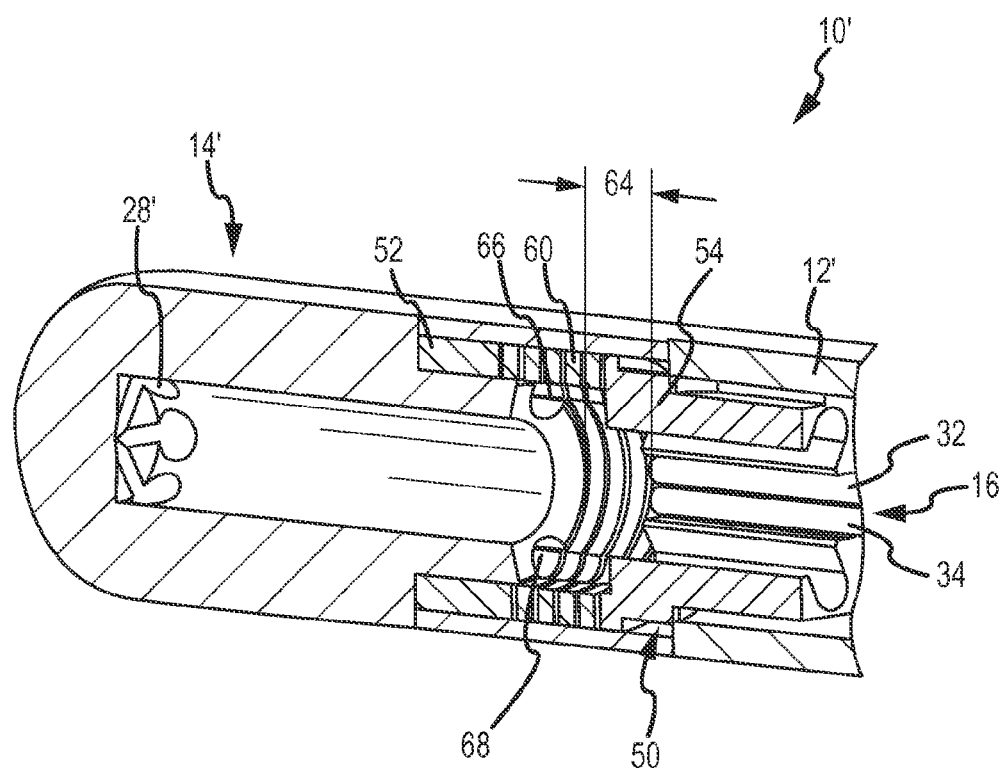

As further shown in FIGS. 6A and 6B, the electrode 14' having base portion 26', respectively, is positioned within the neck portion 52 of the coupling member 50 so that a gap and/or area 64 is provided between optical sensors 16 and optically interactive surface 30'. As tip portion 24' of electrode 14' is exposed to external force through contact with tissue, neck portion 52 of coupling member 50 moves relative to the mounting shaft 54. The relative movement of the neck portion 52 to mounting shaft 54 is facilitated by the elastic portion 60 of member 50. Gap 64 may vary in size depending on the size of the electrode, as well as the desired optical interaction between the electrode and the optical sensor. The length of gap 64 correlates to the size of elastic coupling 60 as provided by neck portion 54 of coupling member 50.

FIG. 6B further includes at least one lumen 66 for receiving various energizing or sensing components. Lumen 66 is provided for receiving sensing components such as a thermal sensor, pressure sensor, tissue sensor, electrogram sensor, or other type of sensors and combinations thereof that are known by those of ordinary skill in the art. An additional lumen 68 may further extend from the catheter shaft 12' through coupling member 50 and into electrode 14', therein providing an energizing component, such as source for radiofrequency current, direct current, high-intensity ultrasound, laser, cryogenics, or other type of energizing component and combinations that are known by those of ordinary skill in the art. Additional lumens may be provided in or through the contact sensing assembly 10' for communication with additional components, such as electrical components or fluid (e.g., saline or medicament) passageways.

Figure 7:
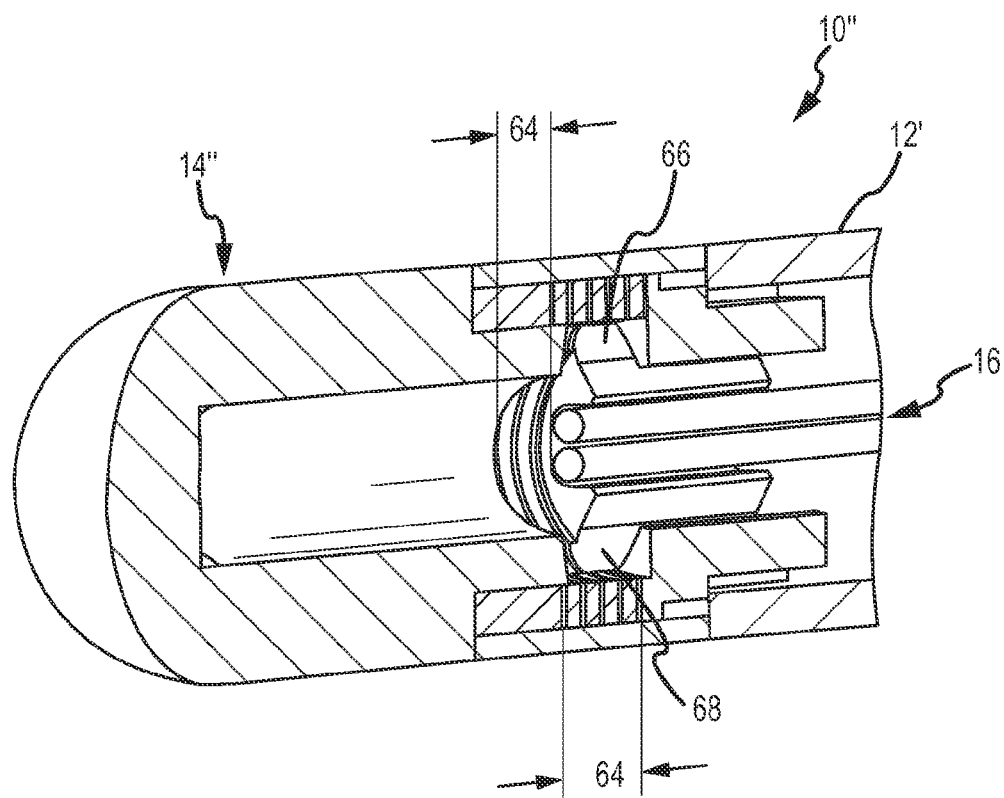
FIG. 7 is a cross-sectional view of an assembly in accordance with another embodiment of the invention.

As can be seen in FIG. 7, an alternate electrode 14" may be provided depending on the type of procedure or use of the catheter assembly, in particular, a non-irrigated electrode. As previously suggested, various electrode configurations may be used in connection with the present invention either having an irrigated electrode tip or a non-irrigated electrode tip. Collectively, electrode 14 (including 14' and 14") may be used in connection with the various embodiments of the invention disclosed. Moreover, alternate additional features may be included in various embodiments, such as the inclusion of lumens 66, 68 and area 64. Each of these components and additional features may be used interchangeably throughout various embodiments of the present disclosure.

Figure 8A:
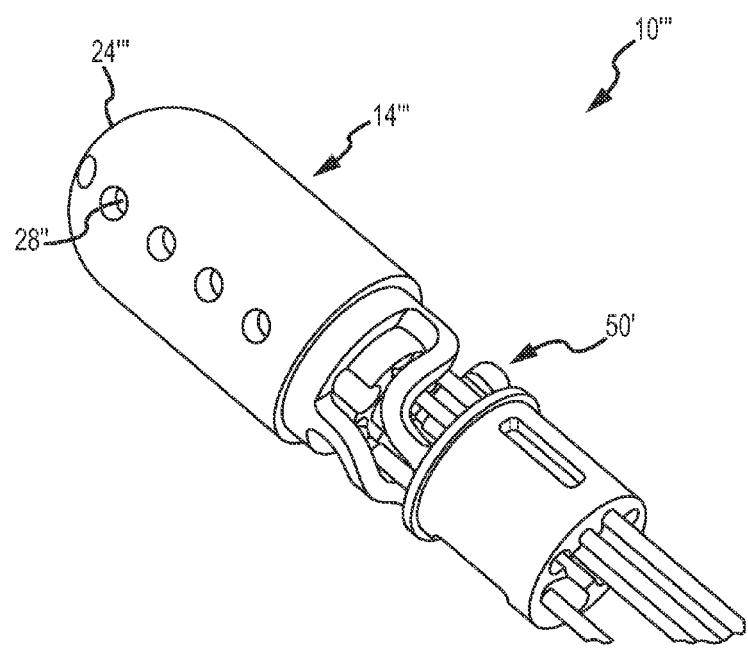
FIG. 8A is a perspective view of an assembly in accordance with an alternate embodiment of the present invention.
Figure 8B:
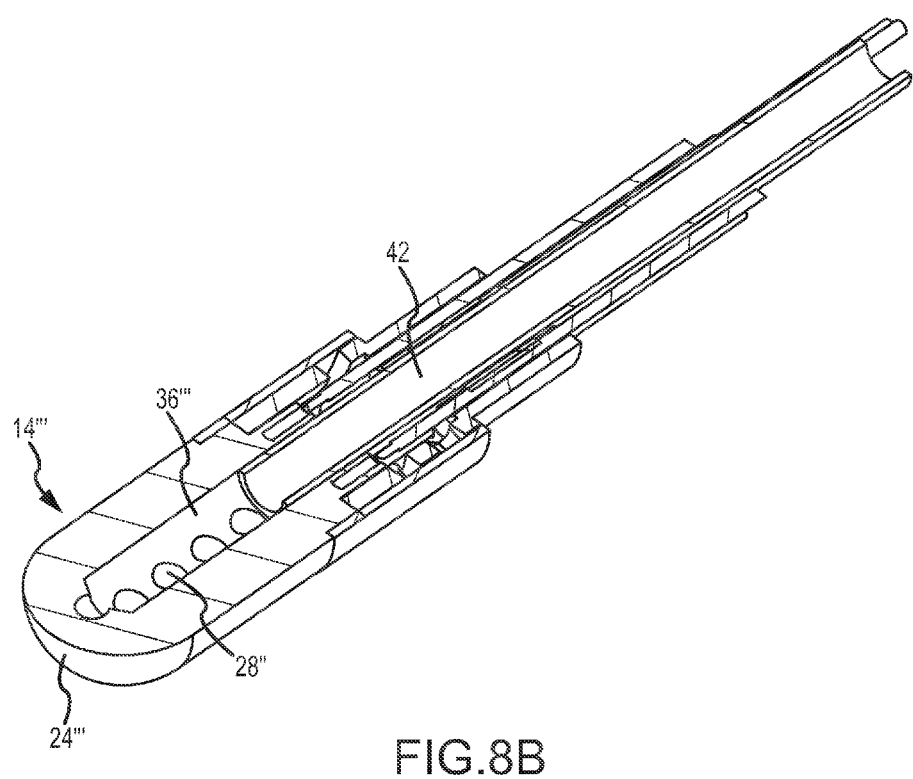
FIGS. 8B and 8C are side cross-sectional views of the assembly of the type shown in FIG. 8A.
Figure 8C:
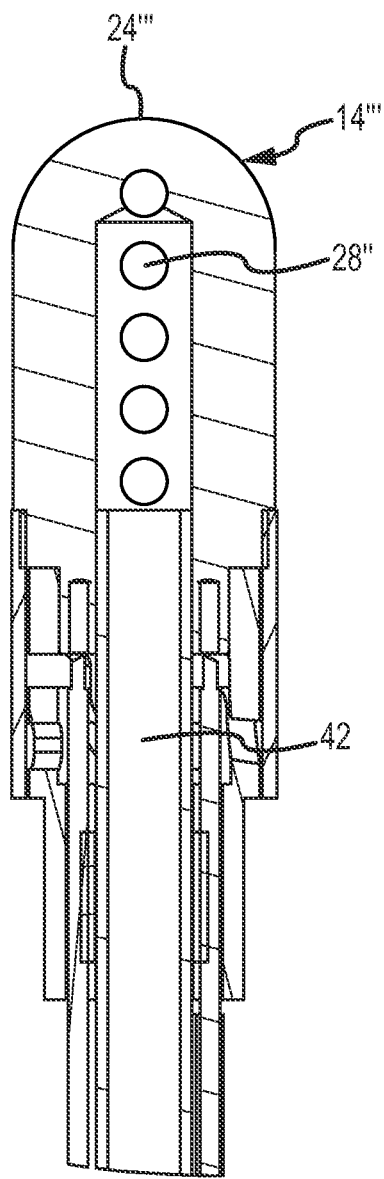

An alternate embodiment of assembly 10''' is shown in FIGS. 8A-8C, wherein an irrigated electrode 14''' is provided in connection with an alternate embodiment of coupling member 50'. Among other things, FIG. 8A illustrates an alternate configuration of irrigation ports 28" provided by electrode 14'''. As previously described, irrigation ports 28" may be incorporated within the electrode to irrigate the surrounding tissue and surface relative to the electrode during the application of RF energy, or whenever desired by the operator. The irrigation ports 28''' may be provided in various configurations, such as aligned along the length of the electrode (for example, as shown in FIGS. 8A-8C), or dispersed about the electrode to irrigate the tissue in various ways. The irrigation ports 28" may be paired or offset from a common axis and may further be provided in a pattern about the electrode. At least one distal port may further be provided in an alternate embodiment, such that the distal tip or end portion 24''' may be irrigated. Moreover, irrigation ports 28" may be designed to have a circular opening (as shown) or alternate configurations, such as conical, arcuate, rectangular, square, oval or any other type of configuration that would be considered by one of ordinary skill in the art and would facilitate the irrigation of the electrode. The number of irrigation ports 28" provided within an electrode may further vary depending on the design and size of the electrode used in connection with the teachings of the present disclosure. In addition, the size of the irrigation ports 28" may vary depending on the design of the electrode, such that the ports may have a uniform diameter or may have alternate diameters depending on the desired irrigation of the electrode. Accordingly, as shown in FIGS. 8A-8C, an exemplary total of five (5) irrigation ports 28", having uniform diameters, are disposed along one side of the electrode 14'''. The irrigation ports 28" are aligned together to provide a directional irrigation pattern of fluid to the surrounding tissue. The irrigation ports 28" shown in FIGS. 8A-8C are merely exemplary and only provide an alternate embodiment of an irrigated electrode used in connection with the assembly of the present disclosure. Similarly, irrigated electrodes 14 and 14', as previously shown, illustrate alternate embodiments that may be used in connection with the teachings of the present disclosure.

FIGS. 8B and 8C provide cross-sectional views of the assembly 10''' shown in FIG. 8A. As seen, electrode 14''' further includes the electrode cavity 36''' that transports fluid from lumen 42 to the irrigation ports 28". Alternatively, different lumens may be provided in connection with each of the irrigation ports 28", therein providing each port with their own lumen for fluid transfer. This type of configuration may be used to further facilitate directed irrigation relative to the tissue.

During operation, once or after the electrode is placed in contact with tissue targeted for ablation and the relative orientation of the electrode is detected, the directional irrigation ports 28" may be targeted toward the tissue. Subsequently, upon energizing the electrode, such as through the application of RF power, the directional irrigation ports 28" may provide directed cooling of the electrode-tissue interface.

Figure 9A:
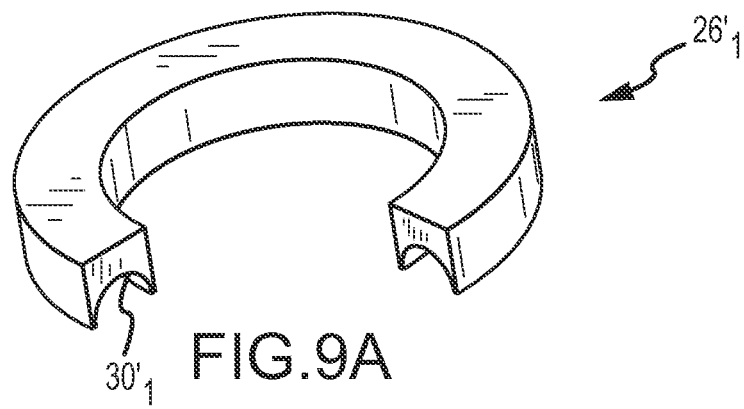
FIGS. 9A-9F are alternate embodiments of a portion of the assembly in accordance with the invention.
Figure 9B:
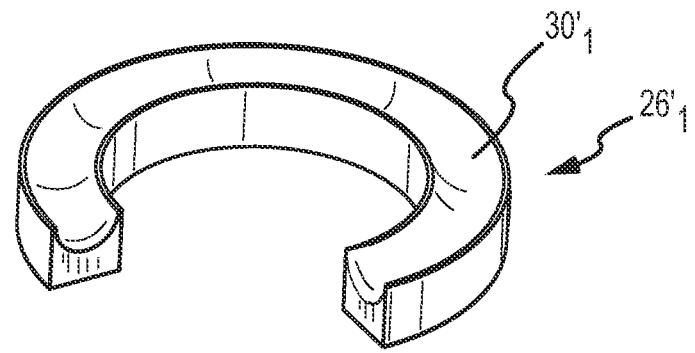
Figure 9C:
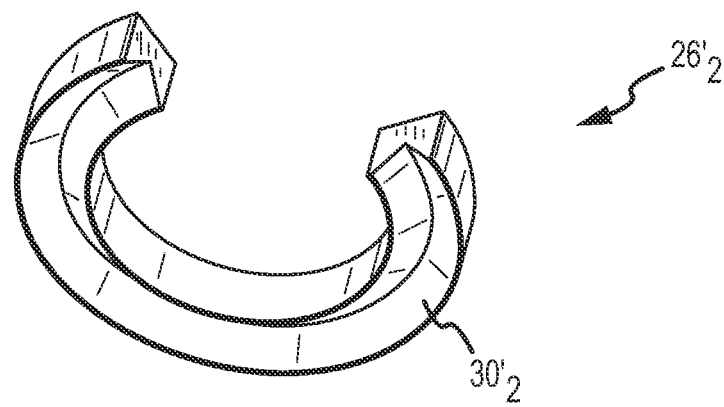
Figure 9D:
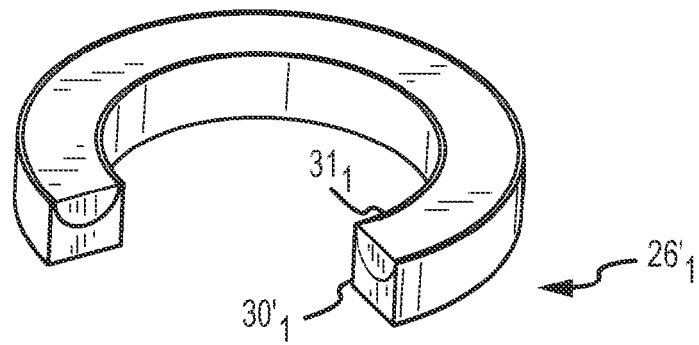
Figure 9E:
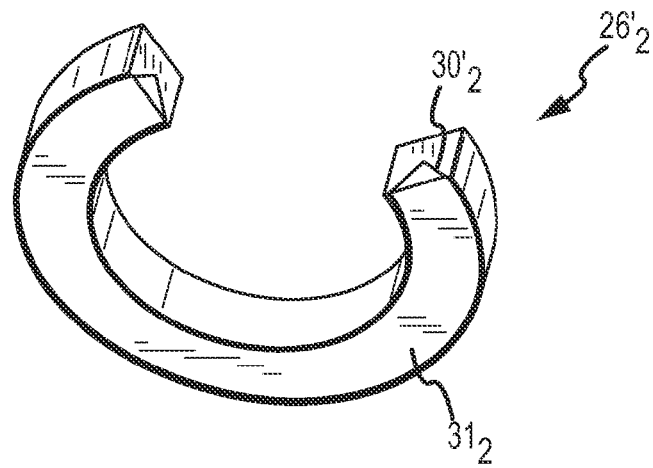
Figure 9F:
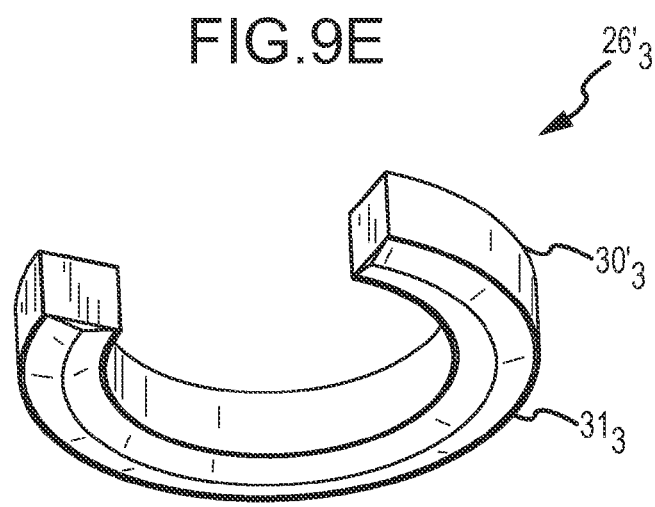

FIGS. 9A-9F generally illustrate alternate configurations of the base portion 26' in accordance with alternate embodiments of the invention. Although not shown, in the provided figures, the base portion 26' can be connected to and/or may be an integrated part of the electrode 14', for example, as shown in FIG. 5B. FIGS. 9A-9C depict alternate embodiments of optically interactive surface 30'$_1$, 30'$_2$ comprising part of base portion 26'$_1$, 26'$_2$ wherein optically interactive surface 30'$_1$ may be hemispherical in shape, alternatively, surface 30'$_2$ may be provided in a more angular/planar design. The design of the optically interactive surface may vary depending on the physical requirements of the optical system and the desired interaction with the optical signal emitted and reflected by the associated optical sensor or sensors. In alternate embodiments, as shown in FIGS. 9D-9F, various embodiments of refractive media 31 (31$_1$, 31$_2$, 31$_3$) may be provided in connection with base portion 26'$_1$, 26'$_2$ and 26'$_3$ to optically interact with the signal (e.g., light) generated by optical sensor 16 of the invention. As shown, the media 31 (31$_1$, 31$_2$, 31$_3$) may be prismatic or plano-convex. Moreover, optically interactive surface 30'$_1$, 30'$_2$, 30'$_3$ may further be provided in connection with the media 31 (31$_1$, 31$_2$, 31$_3$). Media 31 may further include various lens, filters or other types of structures generally know to interact with electromagnetic signals (e.g., light).

As previously suggested, various embodiments of the present invention further define a gap/area 64. In general, the volume of the area generally defined by the gap/area 64 may also be filled, in whole or in part, with a medium 33 (see, e.g., FIGS. 10A and 10B) that transmits/transfers light. The medium 33 may further allow for the optical interaction of optical sensor 16 with surface 30 associated with electrode 14. Accordingly, the optical signal emitted from optical sensor 16 may be transmitted through medium 33 or it may directly interact with the optically interactive surface 30 depending on the position and/or orientation of the catheter shaft 12 and the overall design of the contact sensing assembly 10. The interaction and orientation of the signal may be correlated to determine an associated amount of external force exerted on electrode 14 disposed on the catheter shaft 12, and may provide information concerning the orientation of the electrode 14. Moreover, the assembly may be calibrated to better ensure appropriate correlation. The optical signal is then reflected or refracted after interacting with the optically interactive surface 30 and received by the optical sensor 16. In an embodiment, the optical signal (e.g., light energy) is emitted by the emitter 34 and received by the receiver 32 of optical sensor 16.

Figure 10A:
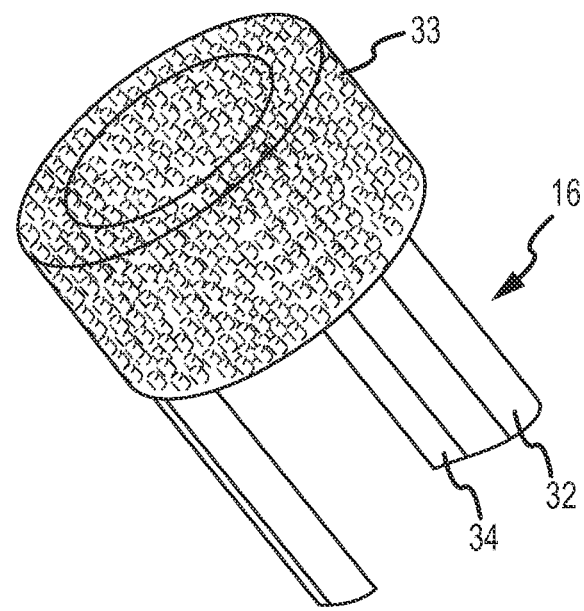
FIGS. 10A and 10B are alternate embodiments of a portion of the assembly for incorporation with the invention.
Figure 10B:
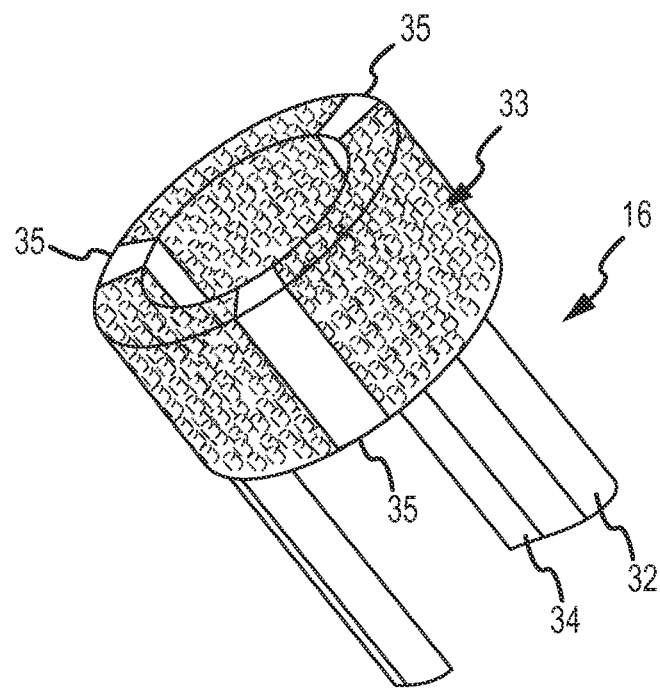

As can be seen in FIGS. 10A and 10B, alternate configurations of the medium 33 are shown. In particular, medium 33 may be positioned within the optical assembly such that the proximal surface of the medium 33 may be coupled to or in proximity with optical sensor 16, while the distal surface of medium 33 may be position in proximity to base portion 26 of electrode 14. As previously discussed, the base portion 26 of electrode 14 may further include the optically interactive surface 30 in various configurations. In an alternate configuration, medium 33 is provided to optically interact with the optical signal generated by the optical sensor 16, in particular, the emitter 34, therein refracting the optical signal for transmitting to the receiver 32. The medium 33 may include air, gel, liquid or other types of compliant materials known in the industry that would optimize performance in accordance with the desired functionality of the assembly 10. In an embodiment, the medium 33 may further be encapsulated within a compliant retaining structure. The medium 33 may be compressible such that the material is responsive to external force exerted on the electrode 14. In an alternate embodiment, the medium 33 may comprise a gel or liquid like material dispersed with a solid or solid particulate such that light is dispersed or refracted (i.e. scattered) by the particulate. An alternate embodiment may provide a liquid or gel-like material that further includes suspended particles (e.g., air or liquid bubbles) that would refract the optical signal provided by emitter 34 to receiver 32. FIG. 10B illustrates another embodiment, wherein opaque partitions 35 are positioned among medium 33, such that the optical signals emitted by one optical sensor 16 may be inhibited from interfering with the signals emitted by another optical sensor 16. Such a configuration can aid in reducing "cross-talk" and/or interference among the optical sensors 16.

A fiber assembly may be further provided by the invention. The fiber assembly includes a supply fiber and a return fiber. The supply fiber (not shown) is connected to emitter 34 and carries light energy from a light source to emitter 34. The return fiber (not shown) carries reflected light from receiver 32 back to a processor and display unit. The light energy emitted by the optical sensor 16 is compared to the light received by the optical sensor 16 and used to determine the relative force exerted on the electrode 14.

In another embodiment, the assembly 10 further provides a first interactive component and a second interactive component, such interactive components may include optical sensors and optically interactive surfaces in various combinations. For example, in an embodiment, that assembly does not necessarily include an electrode, but may provide a sensor that includes a segment with an interactive component and a tip with another interactive component adapted to interact with one another when an external surface of the tip contacts a target.

Figure 12A:
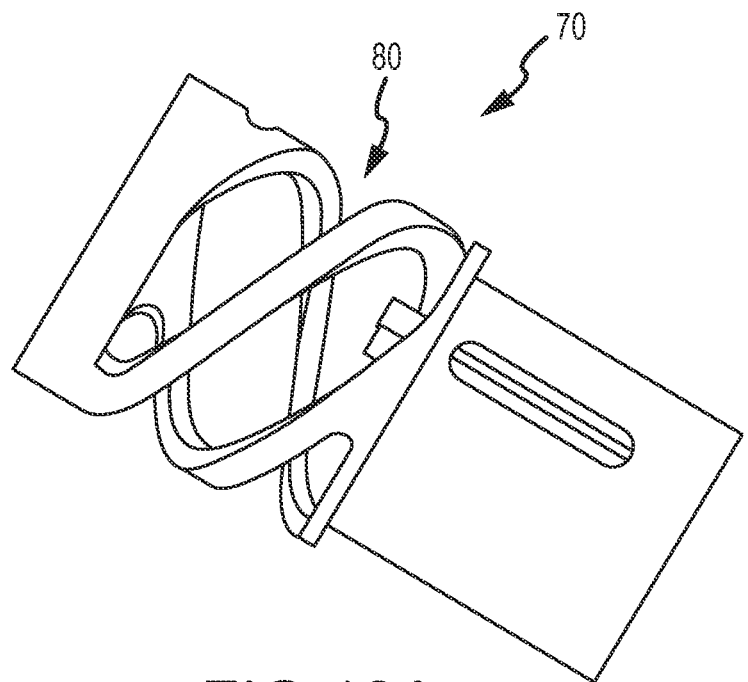
FIGS. 12A-12E are alternate embodiments of a coupling member according to the invention.
Figure 12B:
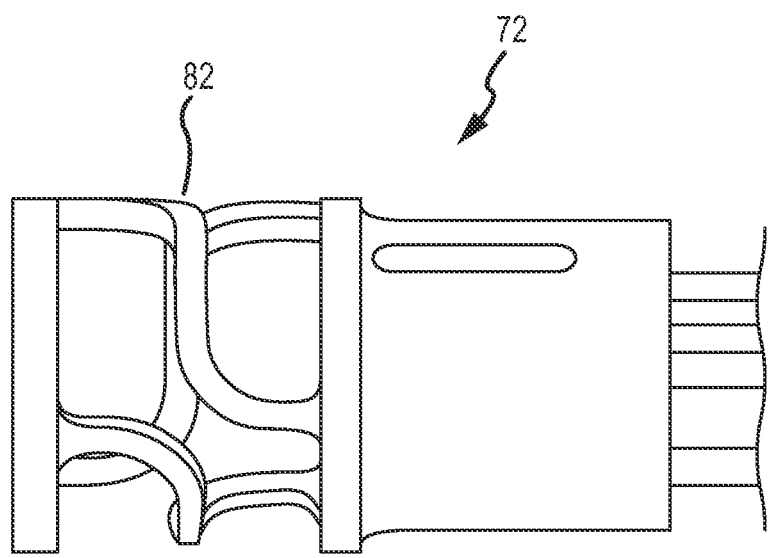
Figure 12C:
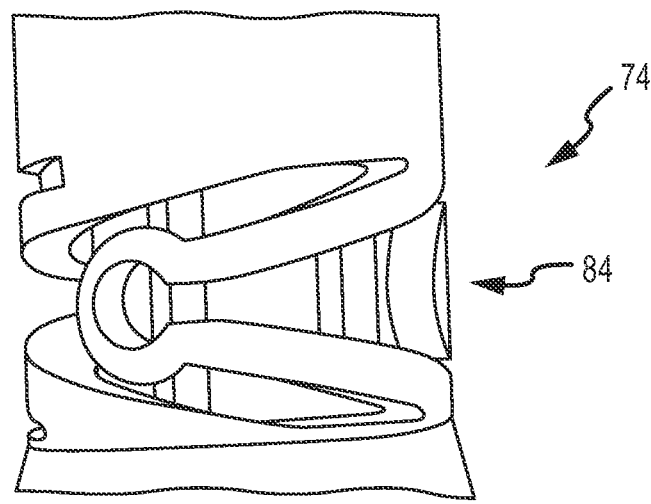
Figure 12D:
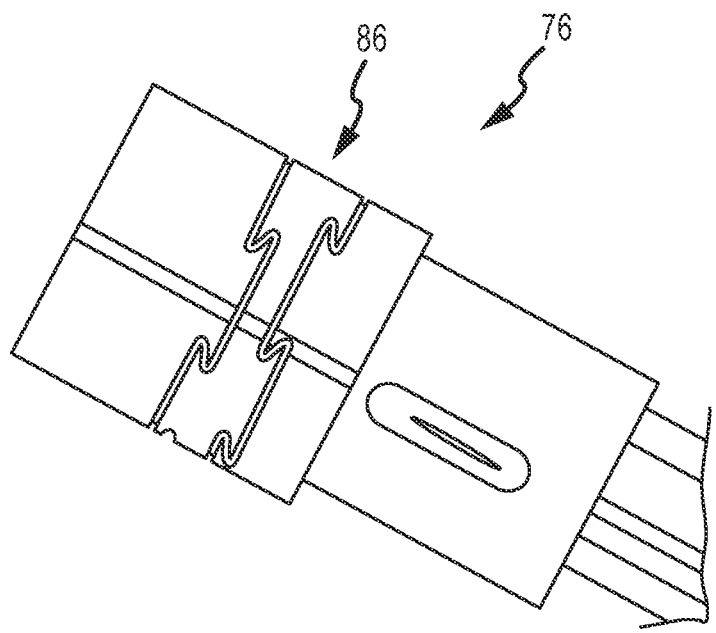
Figure 12E:
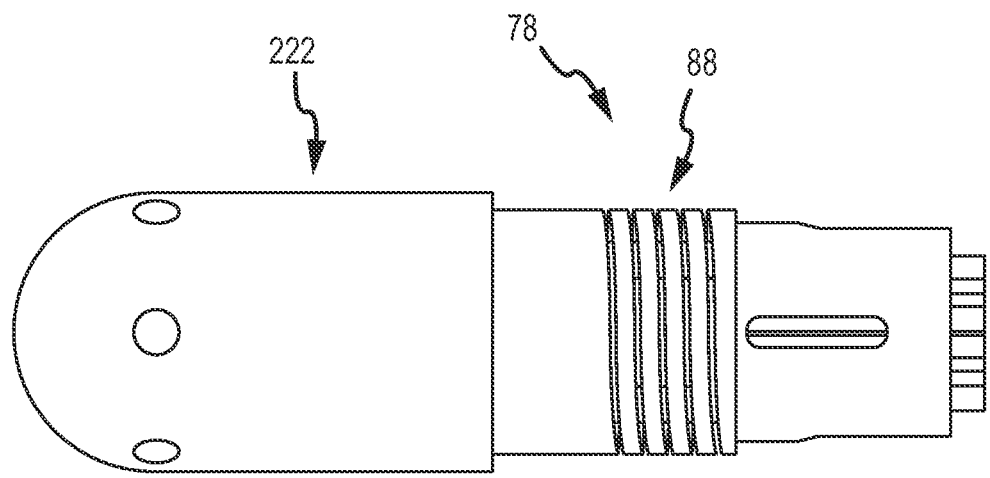

Referring to FIGS. 12A-12E, alternate embodiments of coupling member 50 are illustrated. As shown in FIG. 12A, coupling member 70 may include a twisted configuration for elastic portion 80. As shown in FIG. 12A, the twisted configuration may comprise three interwoven helical torsion bars or arms. Other alternative embodiments of coupling member 50 include a serpentine or sinuous torsion bar coupling member 72 (FIG. 12B); an "alpha" torsion bar coupling member 74 (FIG. 12C); a dovetail, zigzag, or puzzle-piece coupling member 76 (FIG. 12D); and a spring-type or spiral grove or helical groove coupling member 78 (FIG. 12E), respectively, for elastic portions 82, 84, 86, and 88. The coupling member may have other configurations, providing different elastic properties based on specific catheter uses. Each of the coupling members may be designed so that the movement of an electrode 14 or 222 (see discussion below with reference to FIGS. 14A-14D) has a uniform response in the generally x, y, and z directions of a force and/or torque applied to the electrode for measurement by the contact sensing assemblies disclosed herein.

Referring to FIGS. 13A-23 generally, contact sensing based on transverse transmission based emitters and receivers will be described in detail.

Figures 13A, 13B:
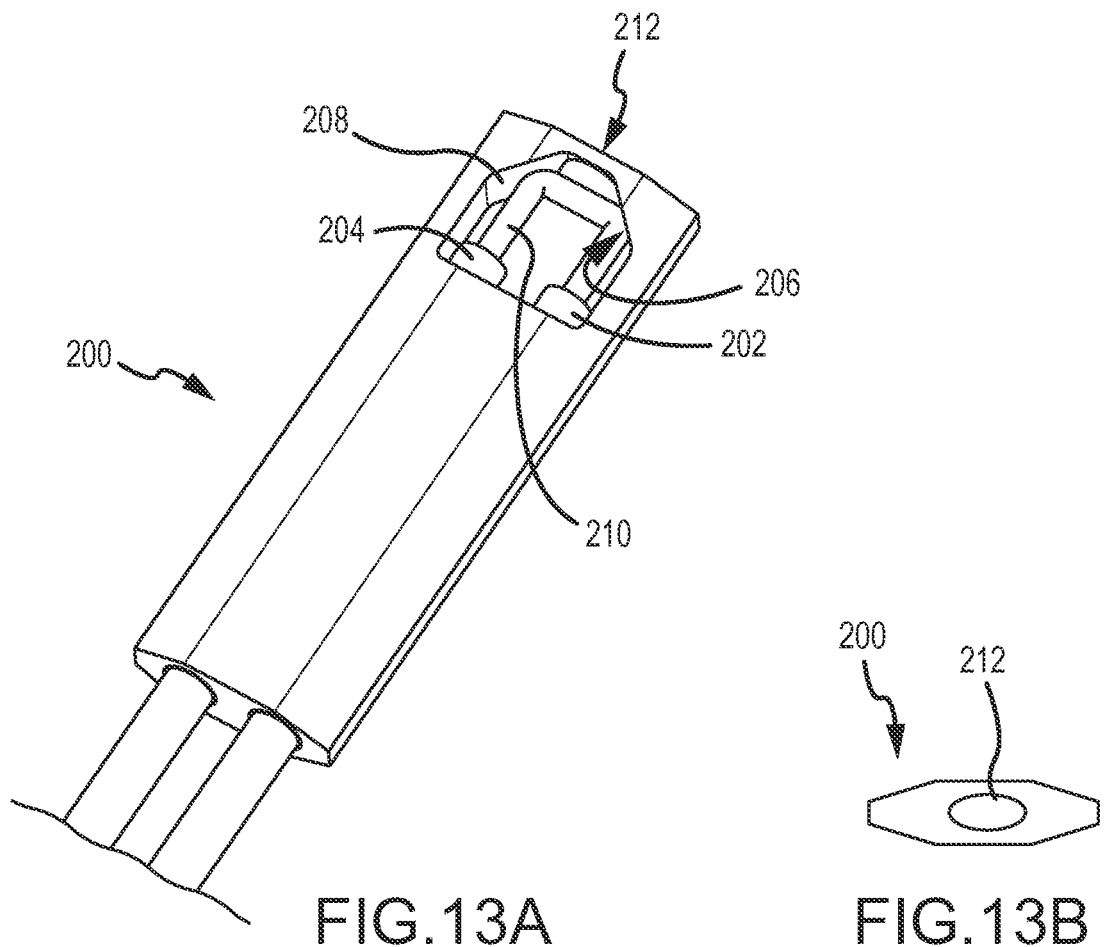
FIGS. 13A and 13B are exemplary isometric and top views of a fiber mirror arrangement for a transverse transmission based emitter and receiver according to the invention.

Specifically, referring to FIGS. 13A and 13B, generally a fiber mirror arrangement 200 may include an emitter 202, receiver 204, and reflective surfaces 206, 208 disposed generally at about a 45° angle relative to the longitudinal axis of, for example, the emitter. A substantially constant intensity optical signal 210 transmitted via the distal portion of emitter 202 may be reflected from reflective surface 206 onto surface 208 and sensed by receiver 204. Absent a full or partial break in the amplitude or intensity of optical signal 210, the signal received at receiver 204 is a substantial and constant portion of the signal emitted from emitter 202. Such a break or disturbance may occur, as discussed below, by an appendage (not shown in FIG. 13) insertable in a hole or other opening 212 in fiber mirror arrangement 200. The degree of such a break or disturbance, which may reduce or increase (see discussion below) the intensity of signal 210 received at receiver 204, may directly correlate to the amount of force on an electrode tip, as discussed below with reference to FIGS. 14A-34. It should be noted that, whereas fiber minor arrangement 200 provides a structure for anchoring emitter/receiver fibers that may be used in an existing or new catheter/electrode assembly as shown in FIG. 1 with minimal modifications, other arrangements of emitters/receivers will be described in detail with reference to FIGS. 14A-23.

Figure 14A:
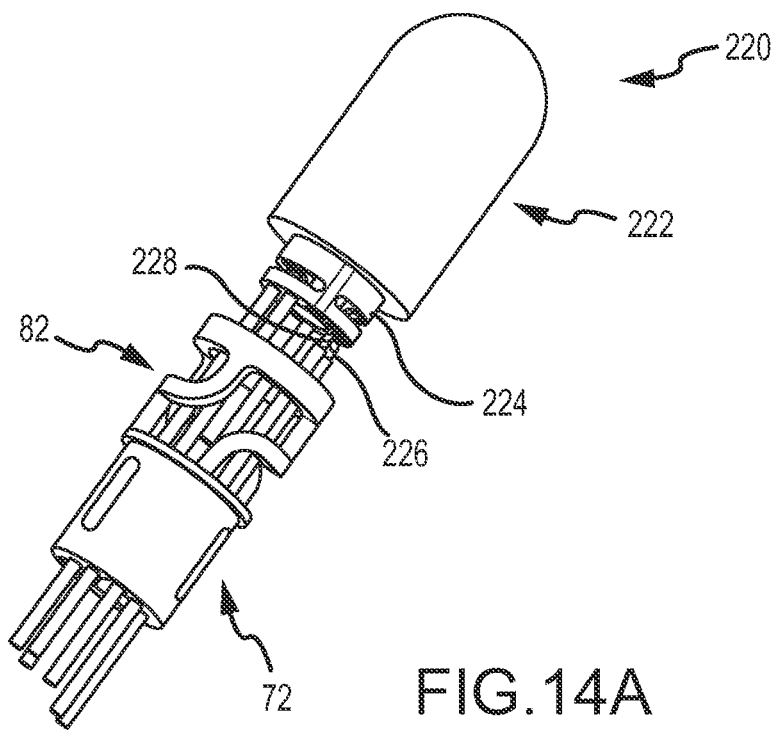
FIGS. 14A-14D are exemplary views of an embodiment of a transverse transmission based contact sensing assembly according to the invention.
Figure 14B:
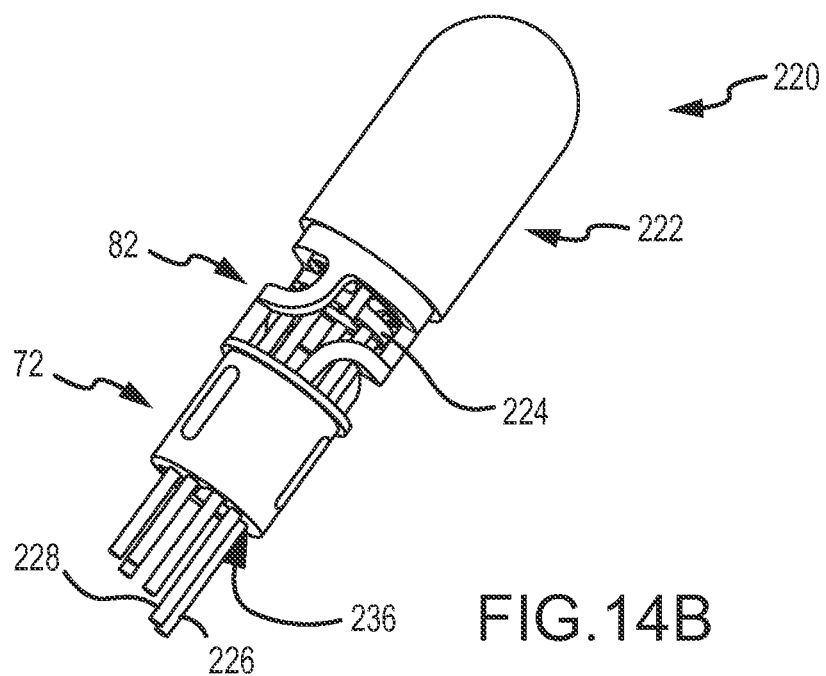
Figure 14C:
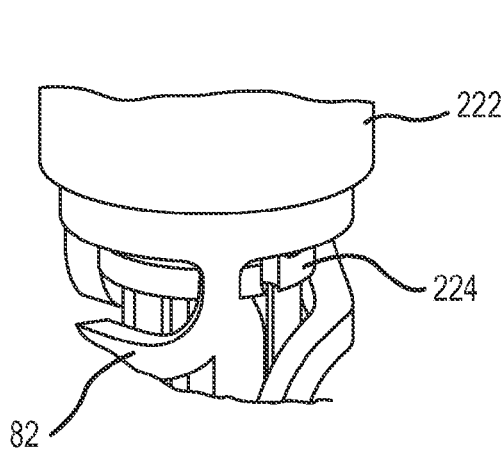
Figure 14D:
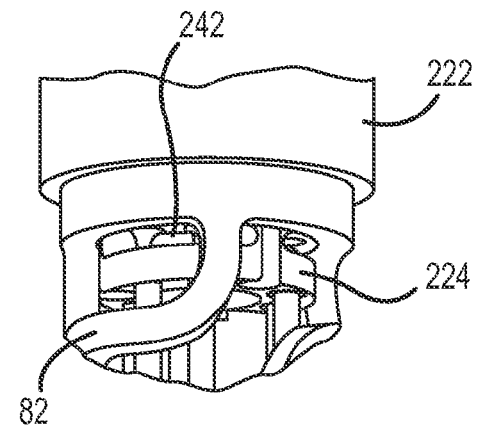
Figure 15A:
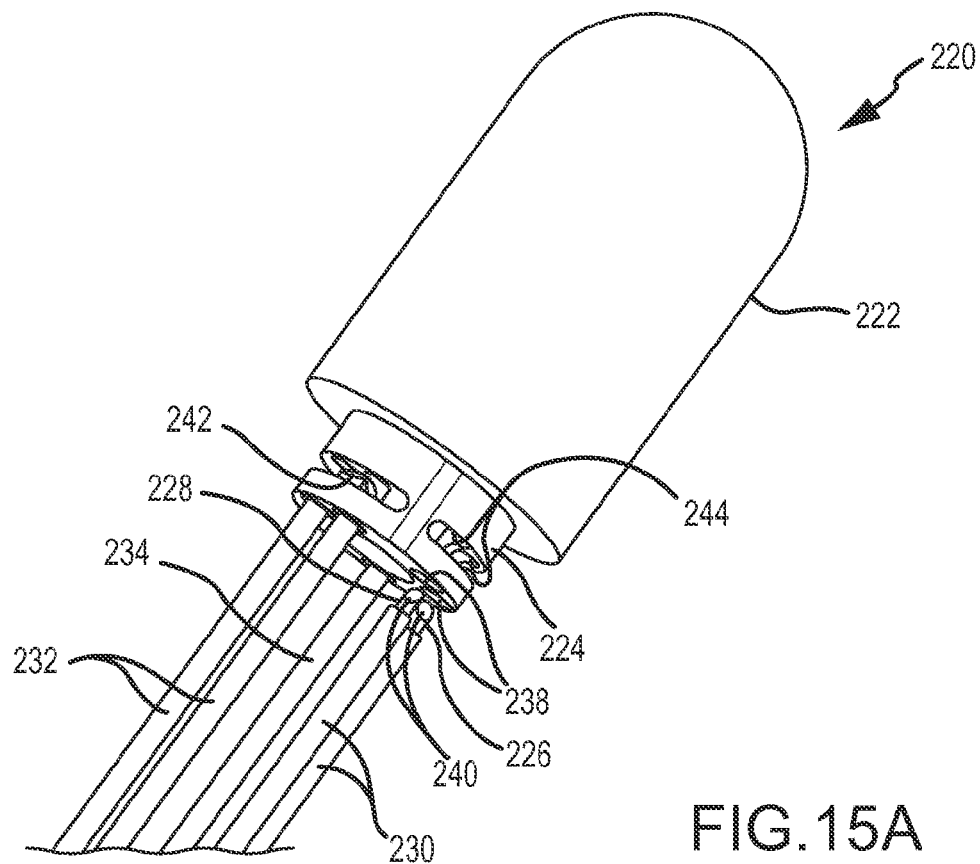
FIGS. 15A-15D are exemplary close-up views of the transverse transmission based contact sensing assembly of FIGS. 14A-14D, with a coupling member removed.

Referring to FIGS. 14A-14D and 15A-15D, an embodiment of a transverse transmission based contact sensing assembly 220 will be described in detail. Contact sensing assembly 220 may generally include electrode 222 disposed at a distal end of a catheter, similar to FIG. 1, and include, for example, torsion bar type coupling member 72 including elastic portion 82. Coupling member 72 may include an electrode receptacle or receiving portion (similar to portion 58 of FIG. 5A) for receiving base portion 224 of electrode 222. As shown in FIGS. 14A and 15A, assembly 220 may include emitter and receiver fibers 226, 228, with the embodiment as illustrated including three sets of emitter/receiver fibers 230, 232, 234. As shown in FIGS. 14B and 15A, emitter/receiver fibers 226, 228 may extend through adequate passages 236 in coupling member 72 and through first sets of passages 238 in base portion 224 (it should be noted that whereas emitter/receiver fiber set 232 is illustrated in the correct configuration in FIG. 15A, set 230 is illustrated prior to insertion into passages 238 in base portion 224; set 230 is illustrated in the correct configuration in FIG. 15B after insertion into passages 238). Referring still to FIG. 15A, emitter/receiver fibers 230, 232 and 234 may include surfaces 240 provided at about a 45° angle relative to the fibers' longitudinal axes so that the substantially transverse optical signal 242 is respectively emitted and received by fibers 226, 228. Alternatively, the emitter/receiver fibers may be cleaved to approximately a 45° angle relative to the fibers' longitudinal axes, or any other optimal angle as required by the invention. Moreover, the cleaved end portions of the emitter/receive may be partially or fully metalized, such as with a reflection enhancing material. Moreover, fiber-cladding may be applied to the optic fibers, in particular, outer surface of the emitter/receiver to further enhance the performance of the fiber.

In operation, with coupling member 72 installed onto base portion 224 of electrode 222 (see FIGS. 14B-14D), any axial, transverse, or rotational forces applied to electrode 222 when contacting tissue, a membrane, or some other surface may result in controlled deformation of elastic portion 82. The resulting deformation may cause the common wall between second sets of passages 244 (see FIG. 15A) in base portion 224 to act as an appendage to partially break the path of optical signal 242. The amount of break, as discussed below, may directly correlate to the axial, transverse, or rotational forces applied to electrode 222, with the forces and angle of rotation being calculated below with reference to FIGS. 24-34. While the path of optical signal 242 in a neutral state of electrode 222 may be unobstructed, optionally, the path of optical signal 242 may be obstructed to a predetermined extent to permit proper calibration of contact sensing assembly 220, as also discussed below.

Referring to FIGS. 16A-16E, an embodiment of a transverse transmission based contact sensing assembly 300 will be described in detail.

Figure 16A:
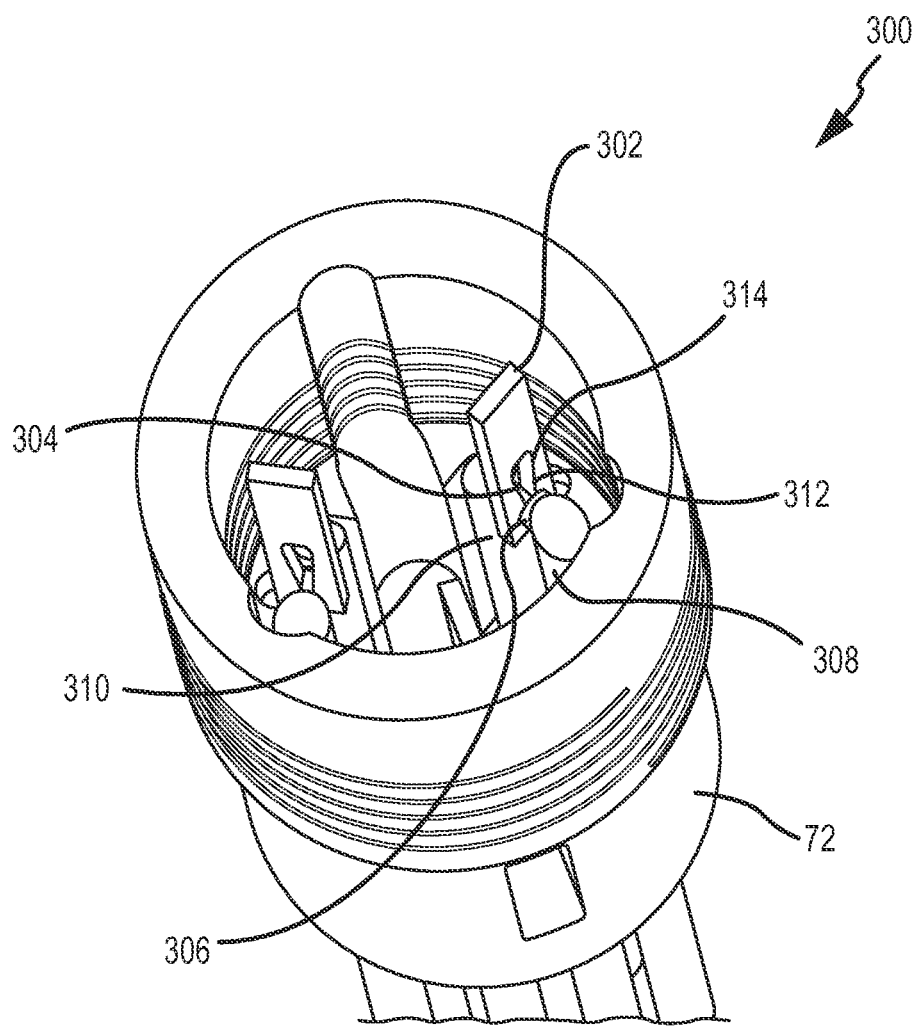
FIGS. 16A-16E are exemplary views of an embodiment of a transverse transmission based contact sensing assembly according to the invention.
Figure 16B:
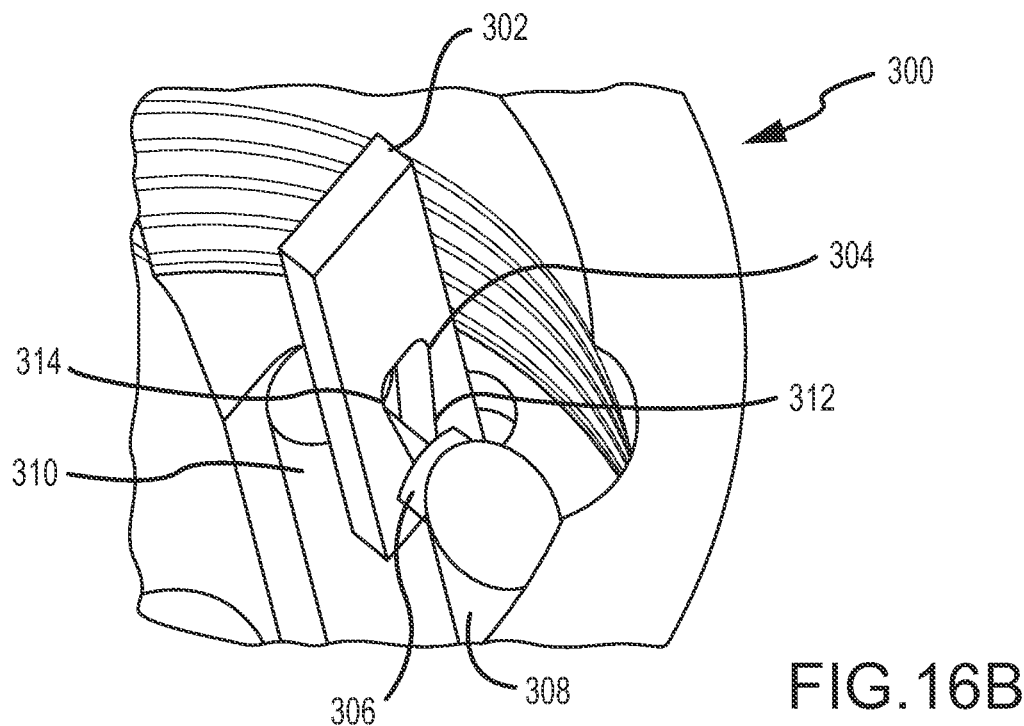
Figure 16C:
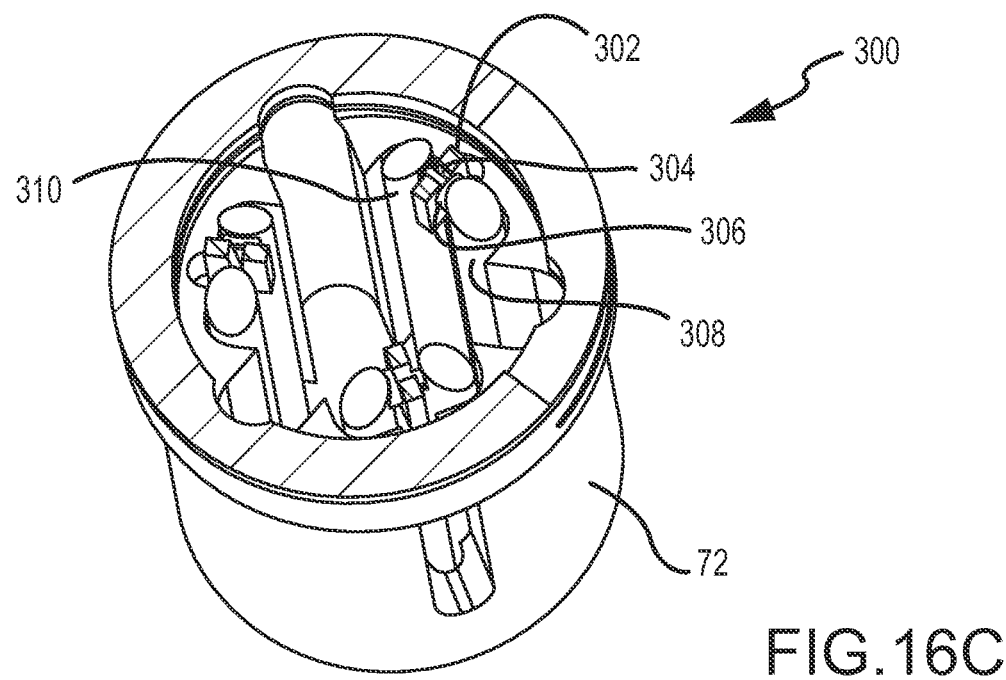
Figure 16D:
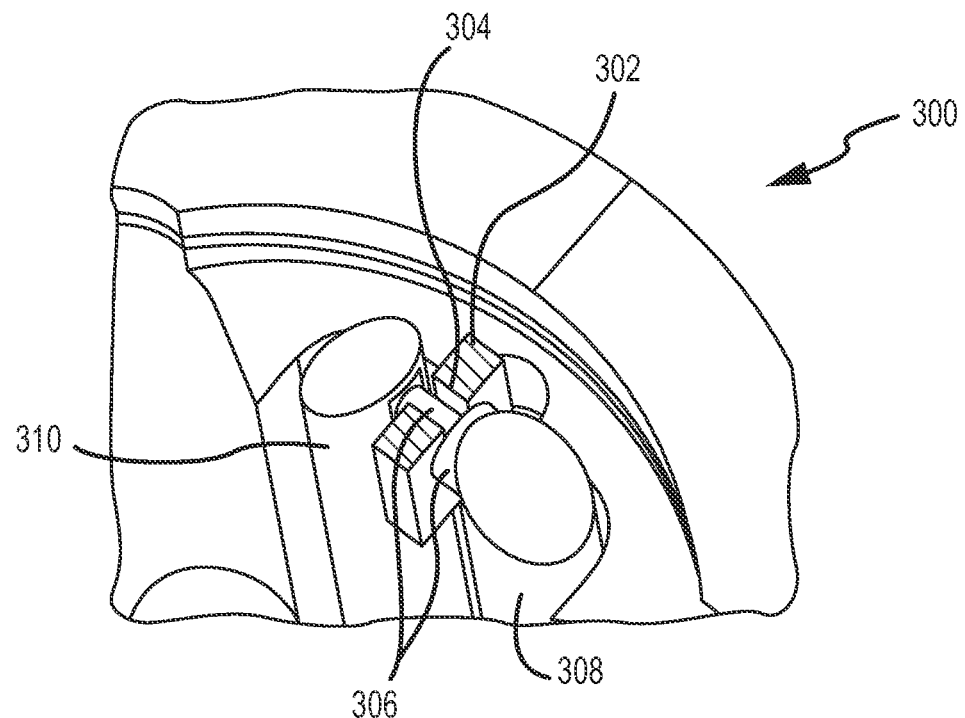
Figure 16E:
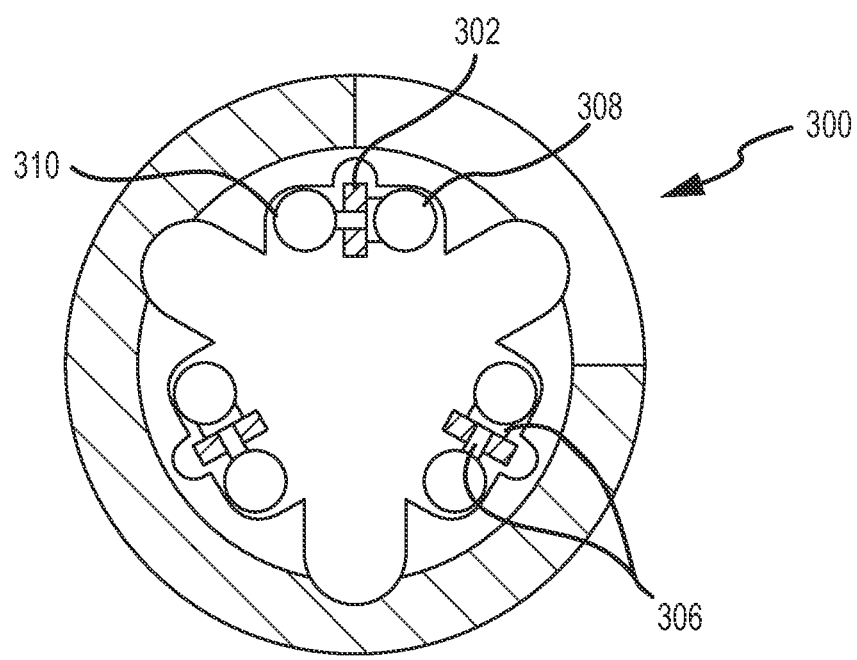

As shown in FIG. 16A, assembly 300 may include an electrode (not shown but similar to electrode 14 or 222) including an appendage 302 affixed to base portion 224. Appendage 302, may include a slit 304 including a pre-defined shape as shown so that axial (any direction) or rotational movement of electrode 222 in the proximal direction under the action of a force causes the intensity of optical signal 306 generated by emitter 308 and received by receiver 310 to increase. As also shown in FIGS. 16A-16D, in the neutral state of electrode 222, the amplitude or intensity of optical signal 306 may be partially reduced by the reduced cross-section bottom area 312 of slit 304 (see illustrative reduced section area of optical signal 306). With electrode 222 moving in a proximal direction as discussed above, the amplitude or intensity of optical signal 306 may increase in the increased cross-section upper area 314 of slit 304. The configuration of FIGS. 16A-16E thus permits proper calibration of contact sensing assembly 300 based on the reduction in intensity of optical signal 306 in reduced cross-section bottom area 312 of slit 304 when electrode 222 is in a neutral state of no force application to the electrode tip. As discussed herein, once properly calibrated, any proximal or other movement of electrode 222 would change the intensity of the optical signal at slit 304, and a further comparison of the optical signal at the other appendages/slits for contact sensing assembly 300 could be used to determine the force and torque applied to the electrode tip.

Referring to FIGS. 17A-23, various embodiments of transverse transmission based contact sensing assemblies will be described in detail.

As shown in FIGS. 17A-17C, contact sensing assembly 350 may generally include an electrode 352 including a base 354 forming or separately including appendages 356. A central emitter 358 may emit a transverse optical signal 360 sensed by radial receivers 362, 364. As shown in FIG. 17A, under the application of an axial force 366, electrode 352 may move in a proximal direction toward the emitter/receivers by an amount Δd. With assembly 350 being calibrated based on the neutral condition of FIG. 17B, the magnitude of force $\vec{F}$ may be calculated as a function of axial displacement Δd, or as a function of change in the intensity of received light based on the amount of blockage of transversely transmitted optical signal 360 (see FIG. 17C). Referring to FIG. 17C, for a transverse force 368 applied to electrode 352, as discussed above and with reference to FIGS. 24-34, the magnitude of force $\vec{F}$ may be calculated as a function of the change and relative comparison in intensity values of optical signal 360 received by receivers 362, 364 based again on the amount of blockage of transversely transmitted optical signal 360. Thus the magnitude of force $\vec{F}$, whether axial or transverse, may be calculated as a function of the amount of blockage of transversely transmitted optical signal 360.

Referring to FIGS. 18A-18C, compared to the embodiment of FIGS. 17A-17C, contact sensing assembly 400 may include an elastic component 402 between electrode 404 and plane 406. For assembly 400, the force $\vec{F}$ acting on electrode 404 may likewise be proportional to the change in light intensity. For example, the force F may be a function of kΔd (e.g. $\vec{F}$~kΔd), where k is the spring constant for the elastic component 402. Since ΔI~Δd, $\vec{F}$~ΔI, where I is the intensity of optical signal 408 transmitted by emitter 410 and received by radial receivers 412, 414, and ΔI is the change in the intensity of the optical signal.

Figure 19:
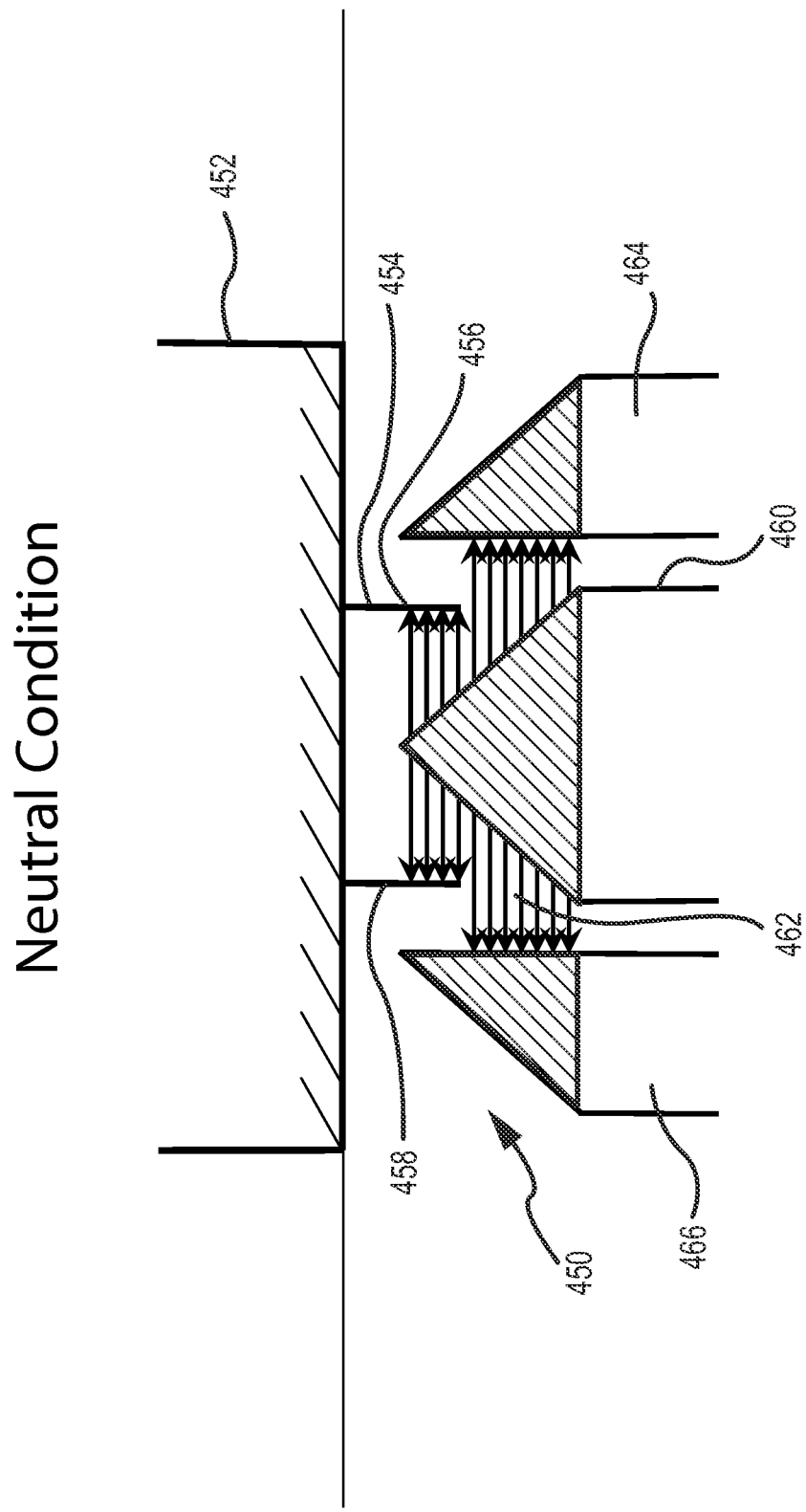

Referring next to FIG. 19, a contact sensing assembly 450 may generally include an electrode 452 including a base 454 forming or separately including appendages 456, 458, and a central emitter 460 transversely transmitting optical signal 462 to peripheral receivers 464, 466. In order to determine the force $\vec{F}$ acting on electrode 452, change in the intensity (I) of optical signal 462 may likewise be determined based on the degree of blockage of signal 462 as discussed below with reference to FIGS. 24-34.

Figure 20:
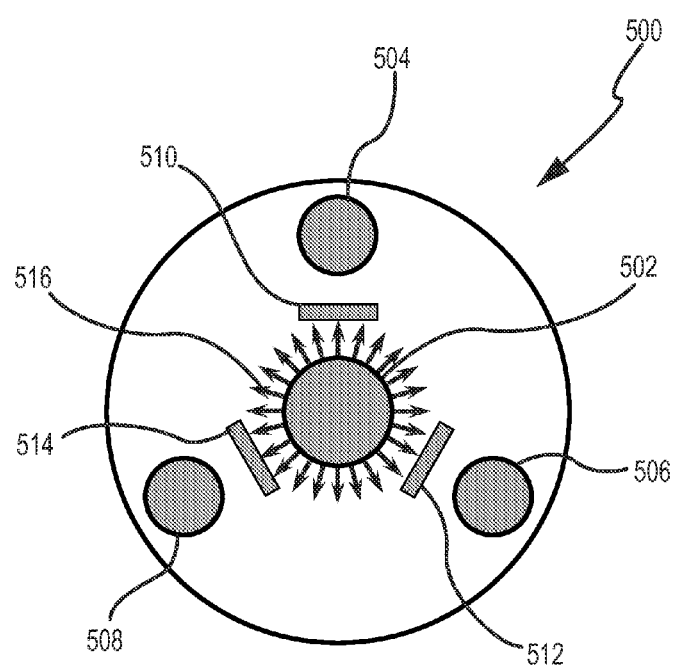

Referring to FIG. 20, a contact sensing assembly 500 including a central emitter 502 and a plurality of peripheral receives 504, 506, 508 with corresponding appendages 510, 512, 514 is illustrated for emitting/receiving optical signal 516. As discussed above for contact sensing assembly 450, in order to determine the force $\vec{F}$ acting on an electrode including appendages 510, 512, 514 mounted thereon, change in the intensity (I) of optical signal 516 may likewise be determined based on the degree of blockage of signal 516 as discussed below with reference to FIGS. 24-34.

Figure 21:
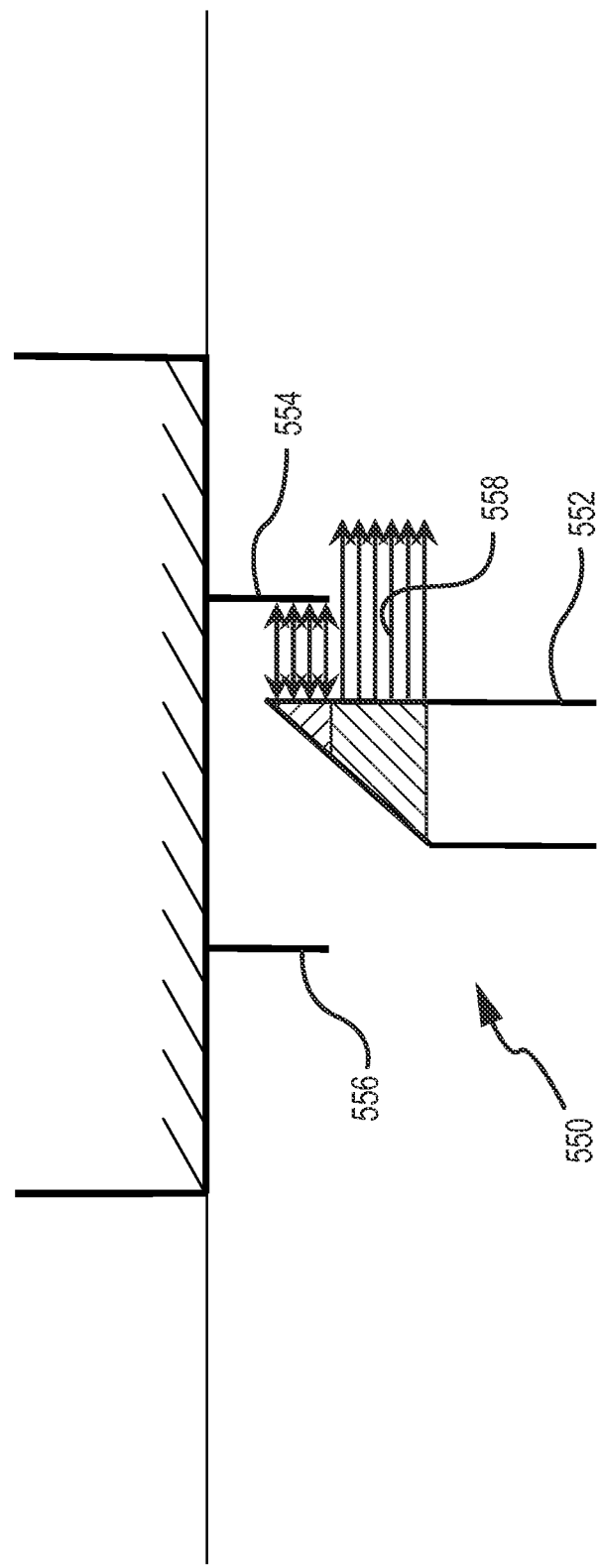

Referring next to FIG. 21, a contact sensing assembly 550 including a dual-function emitter/receiver 552 is illustrated. Assembly 550 may generally include one or more appendages 554, 556 for blocking a transversely transmitted optical signal 558 from emitter/receiver 552. In order to determine the force $\vec{F}$ acting on an electrode including appendages 554, 556 mounted thereon, change in the intensity (I) of optical signal 558 may likewise be determined based on the degree of blockage of signal 558 as discussed below with reference to FIGS. 24-34.

Figure 22:
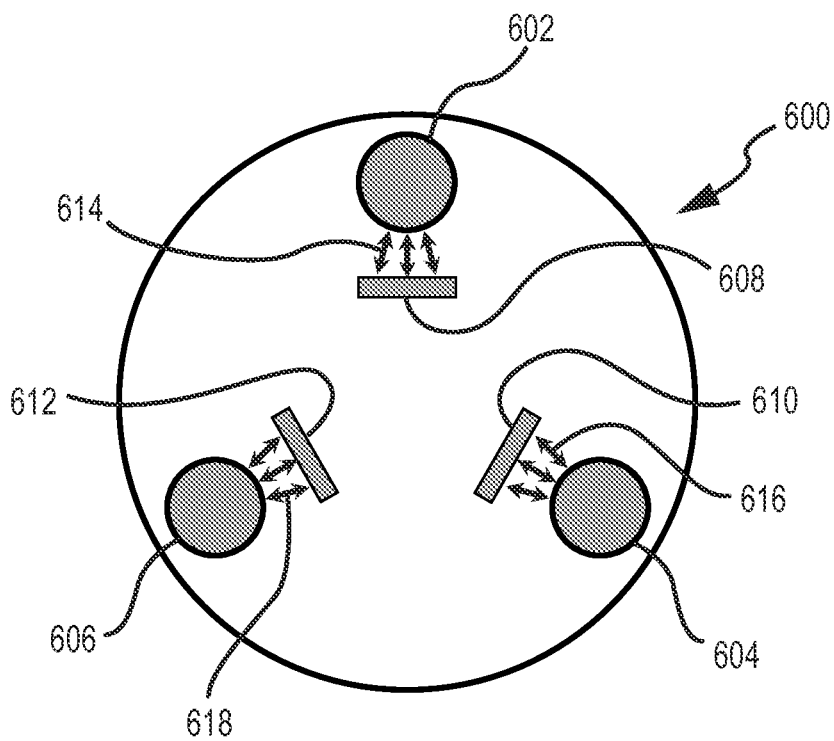

Referring to FIG. 22, an alternate embodiment of a contact sensing assembly 600 including dual-function emitters/receivers 602, 604, 606, and corresponding appendages 608, 610, 612 is illustrated. In a similar manner as assembly 550, appendages 608, 610, 612 may block transversely transmitted optical signals 614, 616, 618 from emitters/receivers 602, 604, 606. In order to determine the force $\vec{F}$ acting on an electrode including appendages 608, 610, 612 mounted thereon, change in the intensity (I) of optical signals 614, 616, 618 may likewise be determined based on the degree of blockage of signals 614, 616, 618 as discussed below with reference to FIGS. 24-34.

Figure 23:
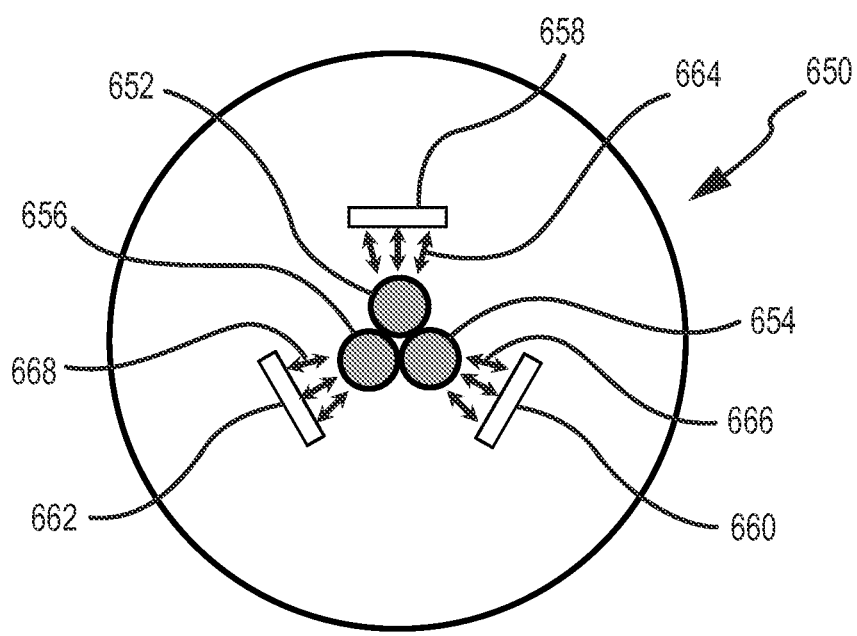

Referring to FIG. 23, another alternate embodiment of a contact sensing assembly 650 including dual-function emitters/receivers 652, 654, 656, and appendages 658, 660, 662 is illustrated. In a similar manner as assembly 550, appendages 658, 660, 662 may block transversely transmitted optical signals 664, 666, 668 from emitters/receivers 652, 654, 656. In order to determine the force $\vec{F}$ acting on an electrode including appendages 658, 660, 662 mounted thereon, change in the intensity (I) of optical signals 664, 666, 668 may likewise be determined based on the degree of blockage of signals 664, 666, 668 as discussed below with reference to FIGS. 24-34.

Referring to FIGS. 24-34, the algorithm, rationale and test results for determination of contact force and angle of rotation of an electrode will be described. It should be noted that the algorithm and methods discussed herein are applicable to all embodiments of contact sensing assemblies disclosed herein with reference to FIGS. 1-23.

Figure 24:
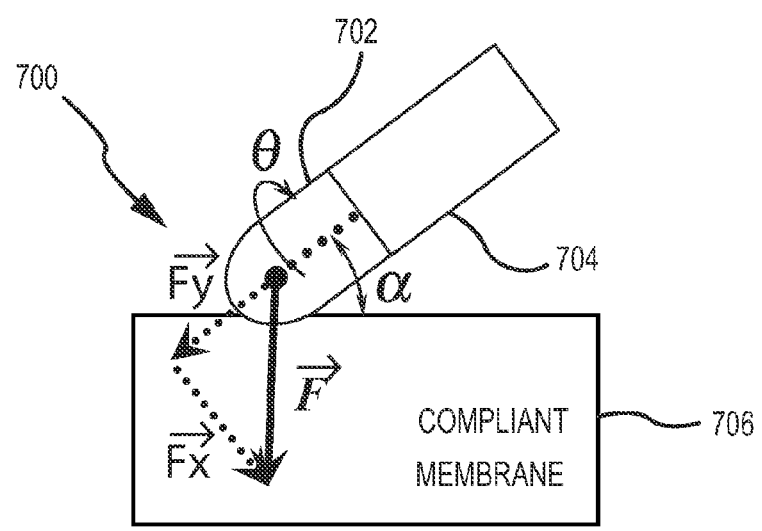
FIGS. 24-27 are respectively an exemplary view of the basis for determining force and torque applied to an electrode, a graph of sensor response to force (axial force $F_y$), an alternate graph of sensor response to force (axial force $F_y$), and a graph of sensor response to force (transverse force $F_x$).

As shown in FIG. 24, a three-dimensional force vector contact sensing assembly 700 (generally representative of the contact sensing assemblies disclosed with reference to FIGS. 1-23) according to the invention may generally include an electrode 702 mounted to an elastic coupling member 704, which is further mounted to a catheter body as discussed above. When contact sensing assembly 700 contacts a surface, such as compliant membrane 706, the resulting contact may occur at an angle α (e.g. angle of attack), with the electrode tip rotating at an angle of rotation θ. The contact force vector $\vec{F}$ may be a function of the axial component of force $\vec{F}y$ and the transverse component of force $\vec{F}x$.

In order to determine the magnitude |F| of force and angle of attack α, contact sensing assembly may first be calibrated to obtain a priori calibration curves for $\vec{F}x$ and $\vec{F}y$. In order to do so, for an exemplary contact sensing assembly 700 including three sets of emitters/receivers (e.g. sensors) such as those illustrated in FIGS. 14A-15D (and generally FIGS. 1-23), first the intensity I01, I02, I03 (e.g. intensity at a Sensor 1, Sensor 2, Sensor 3) at zero-force (e.g. force $\vec{F}$=0) may be measured at the receiver (e.g. for calibrating each Sensor). Thereafter, the intensity I1, I2, I3 at force $\vec{F}$>0 at any angle of attack, i.e. α=0° to 90° may be measured at the receiver. It should be noted that for measurement purposes, the intensity values may be read as voltages. From these values, the intensity change relative to zero-force may be calculated as follows (where "r" stands for relative intensity):

$$I_{1,r} = I_1 - I_{01}$$

$$I_{2,r} = I_2 - I_{02}$$

$$I_{3,r} = I_3 - I_{03}$$

The force $\vec{F}$ may then be resolved at any angle of attack a into axial component $\vec{F}y$ and transverse component $\vec{F}x$ as follows:

$$\vec{F}y = \vec{F} \sin \alpha$$

$$\vec{F}x = \vec{F} \cos \alpha$$

Figure 25:
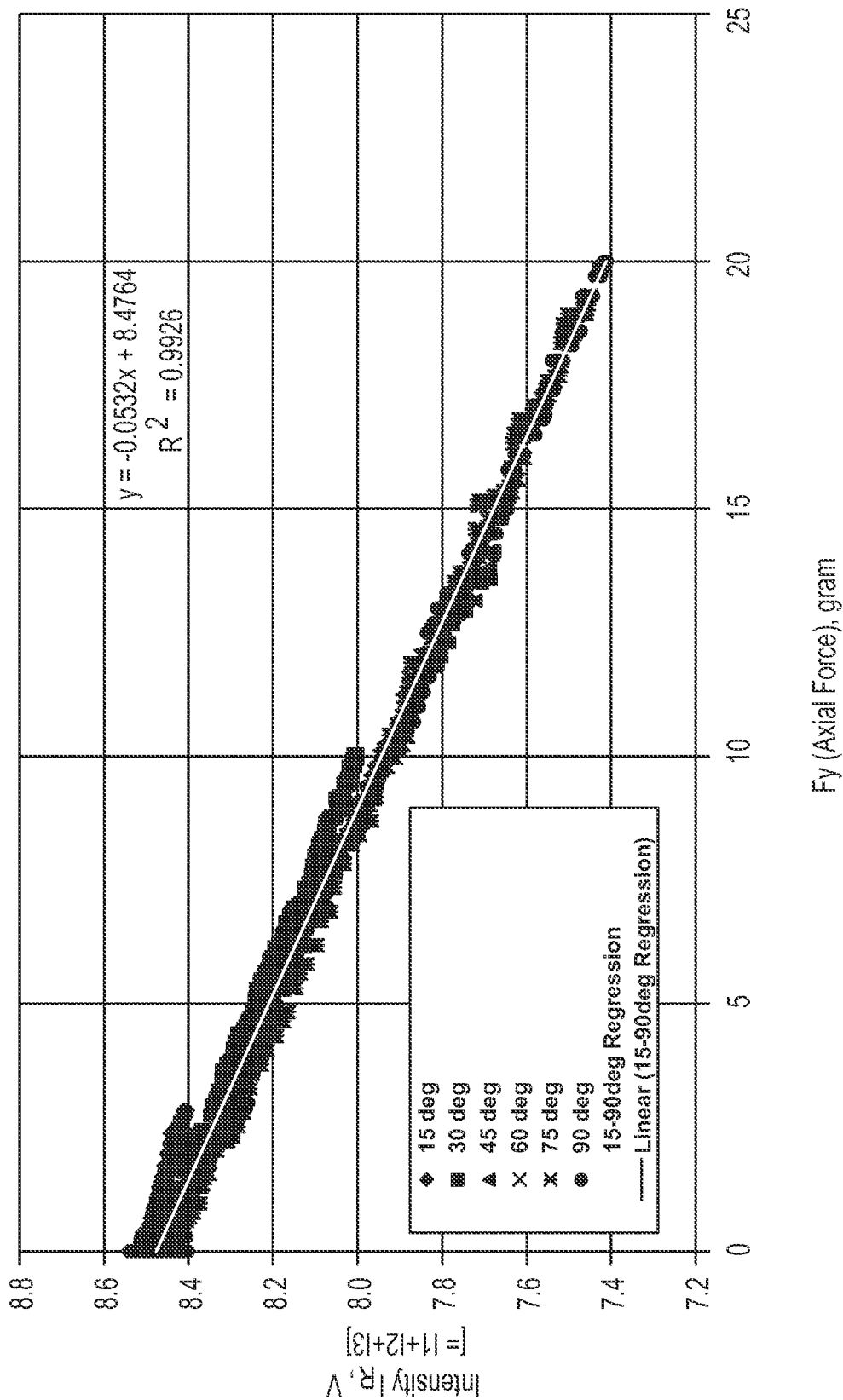
Figure 26:
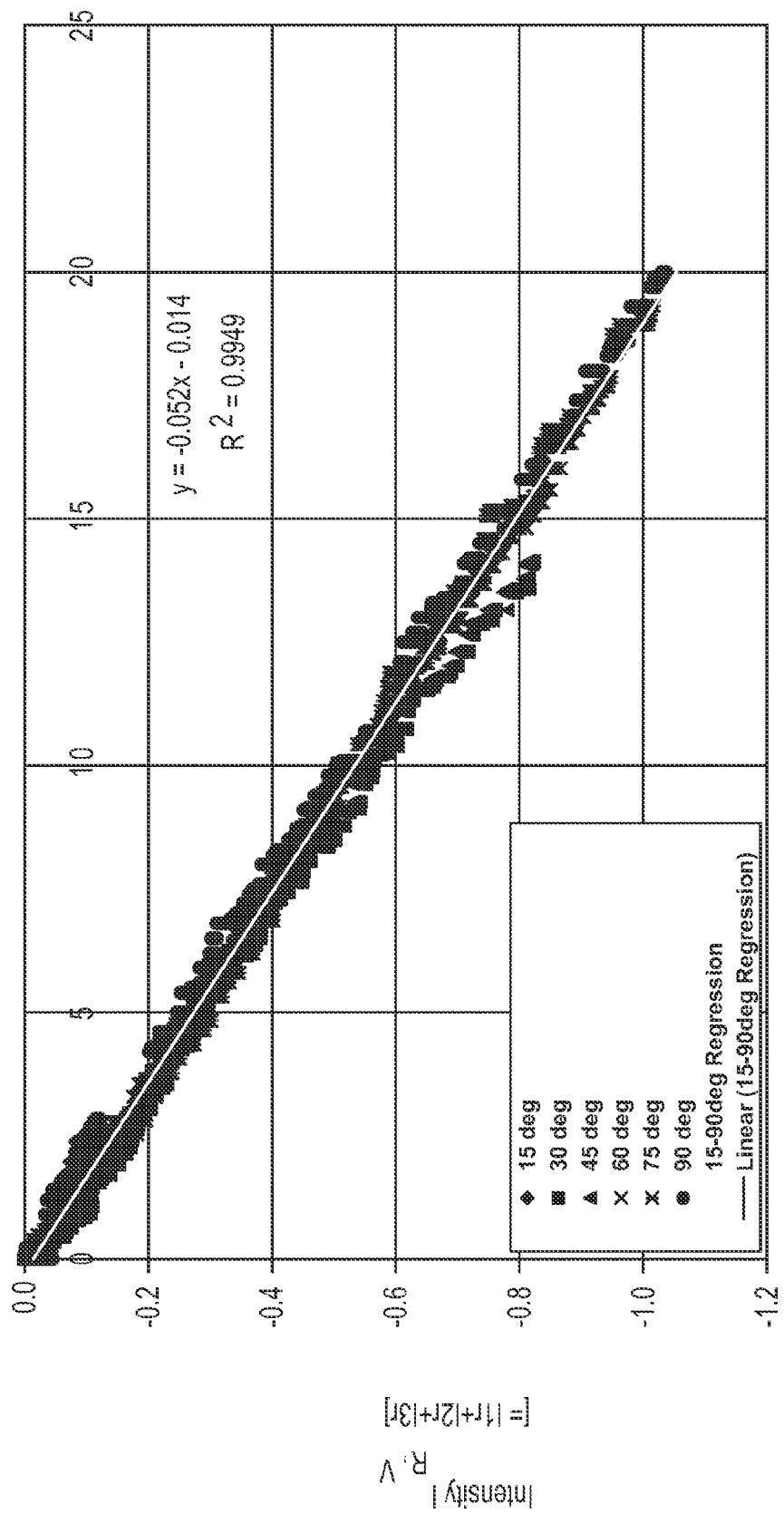

Referring to FIGS. 25 and 26, a regression curve of $\vec{F}y$ may then be obtained as a function of Rickshaw Transformation defined as follows:

Either $I_R=(I_1+I_2+I_3)$, as shown in FIG. 25, or $I_R=(I_{1r}+I_{2r}+I_{3r})$, as shown in FIG. 26 (where "R" stands for resultant intensity) may be used. In the case where $I_R=(I_{1r}+I_{2r}+I_{3r})$, the variations in intensities at zero-force are eliminated which lead to more accurate results. Thus, for more accurate results, $I_R$ calculated as a function of $I_{1r}$, $I_{2r}$, $I_{3r}$, may be used. For FIGS. 25 and 26 (which again show the axial component of force $\vec{F}y$ for Sensor response to force), the test range may be 0-40 grams (with 40 grams being the total force), with an exemplary contact sensing assembly 700 having an accuracy of 0.892 grams, and a standard error of 0.008 grams.

Thus, $I_R=a_{y1}\vec{F}y+a_{y0}$, where $a_{y1}$ is a slope of a linear curve and $a_{y0}$ is the offset.

In the particular examples of FIGS. 25 and 26, $I_R=a_{y1}$ (e.g. −0.0532) $\vec{F}y+a_{y0}$ (e.g. 8.4764), and $I_R=a_{y1}$ (e.g. −0.052) $\vec{F}y+a_{y0}$ (e.g. −0.014). Thus for the example provided, $I_R=(I_{1r}+I_{2r}+I_{3r})$, with the exemplary curve as shown in FIG. 26, may provide a more accurate result.

Figure 27:
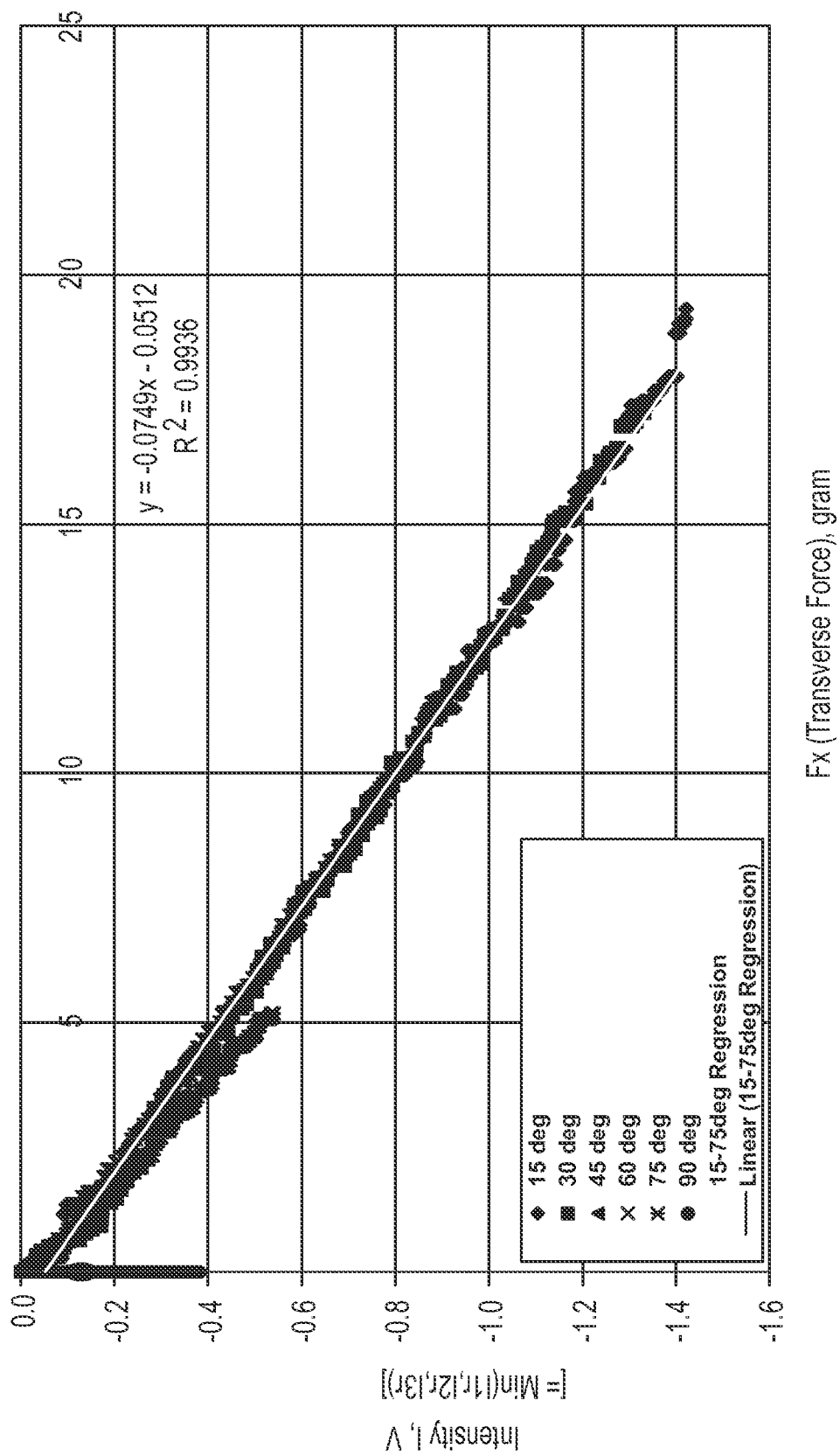

A regression curve of $\vec{F}x$ may then be obtained as a function of $Min(I_{1r},I_{2r},I_{3r})$, e.g. the minimum value between $I_{1r}$, $I_{2r}$, and $I_{3r}$, as shown in FIG. 27 (the transverse component of force $\vec{F}x$ for Sensor response to force) as follows:

$$Min(I_{1r},I_{2r},I_{3r})=a_{x1}\vec{F}x+a_{x0}$$

Referring to FIGS. 29-34, the bench and dynamic test results for exemplary contact sensing assembly 700, discussed also with reference to FIGS. 25-27, will be briefly discussed.

Figure 29:
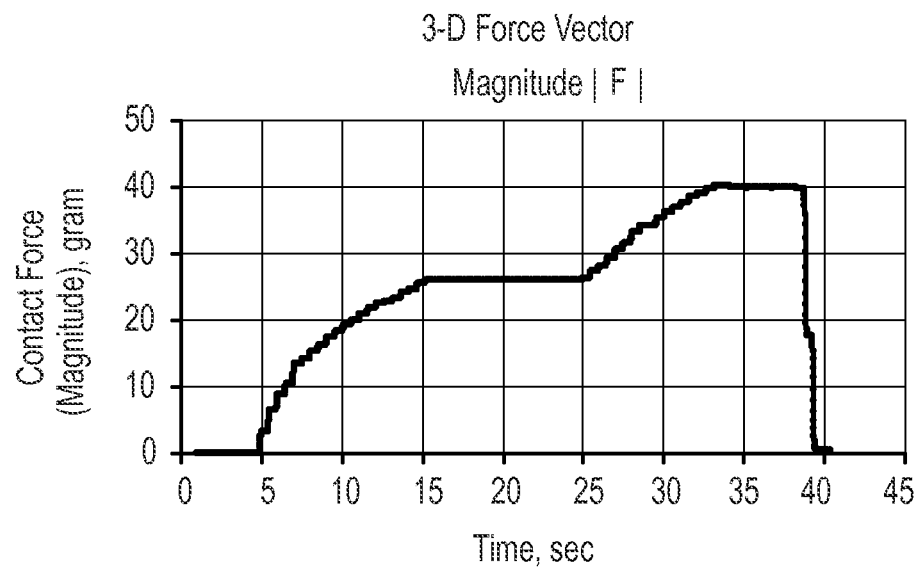
FIGS. 29-31 and 32-34 are, respectively, various graphs of 3-D force vector bench test and dynamic test results for the sensor test results of FIGS. 25-27.
Figure 30:
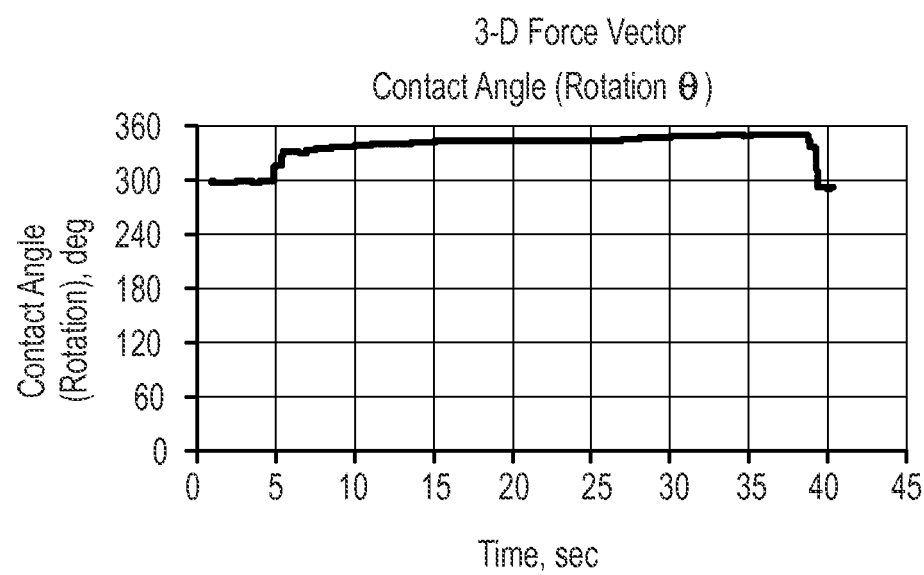
Figure 31:
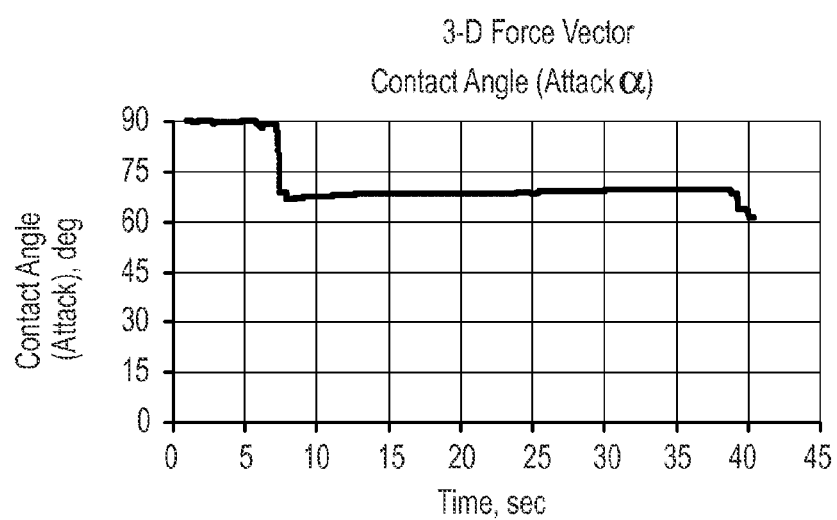
Figure 32:
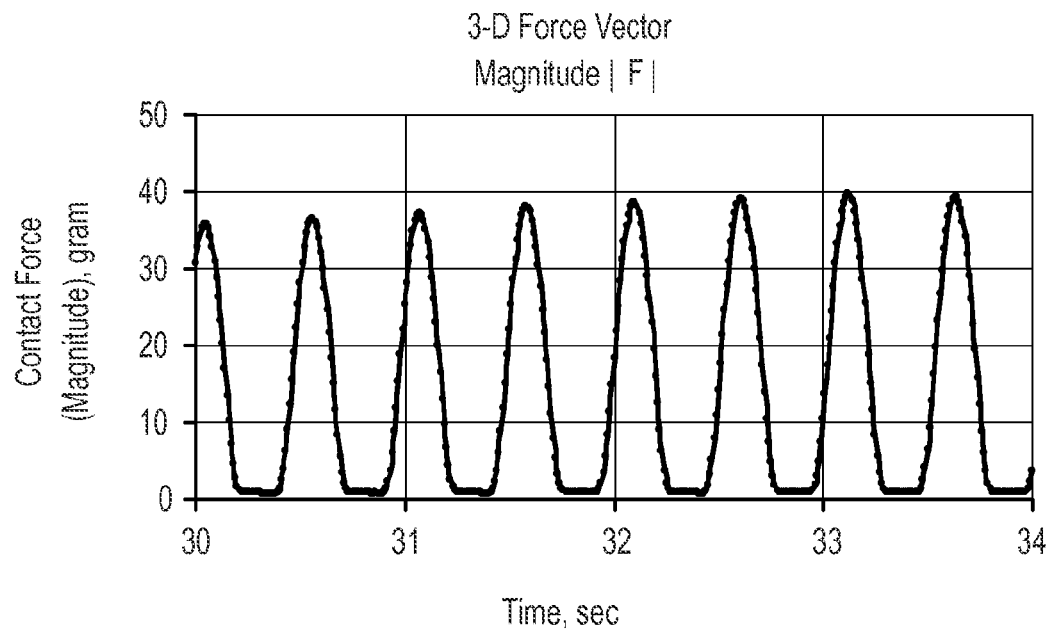
Figure 33:
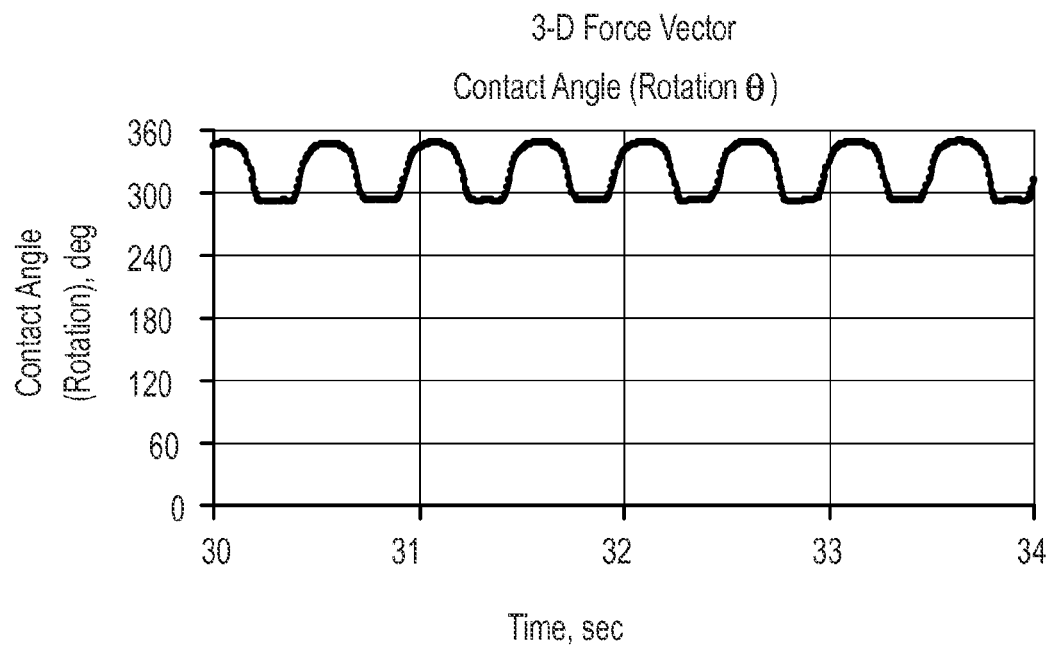
Figure 34:
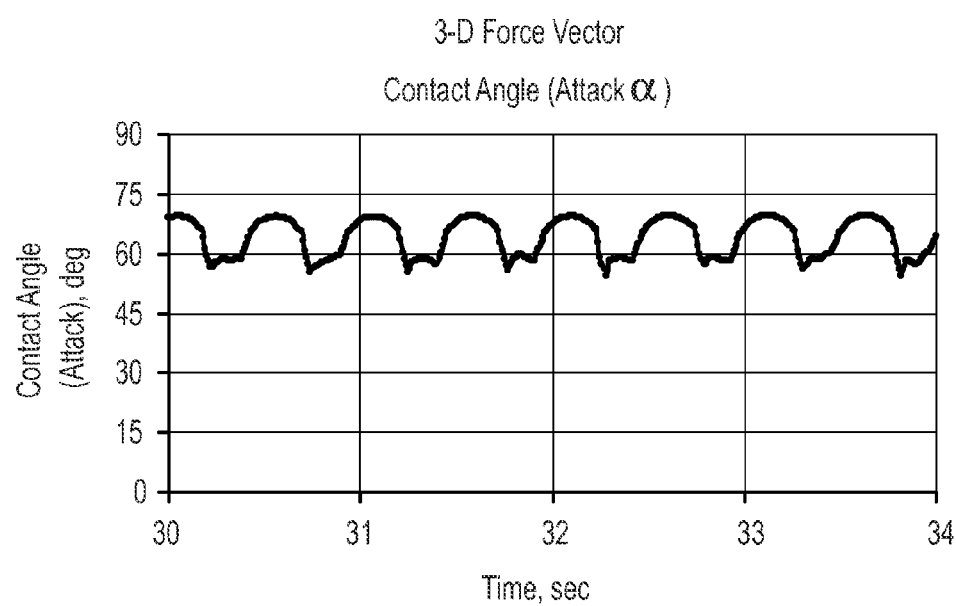

Referring to FIG. 29, the high-points of force |F| for a time interval over 40 seconds are plotted for a bench test, with the sample of FIGS. 25-27 being taken when the force |F| is approximately 40 grams. In a similar manner, FIGS. 30 and 31 respectively show the contact angles (angle of rotation θ and angle of attack α) over a period of 40 seconds for a bench test. FIGS. 32-34 respectively show the results for force |F|, angle of rotation θ, and angle of attack α for a dynamic test for an exemplary contact sensing assembly 700.

After obtaining the a priori calibration curves for $\vec{F}x$ and $\vec{F}y$ as discussed above with particular reference to FIGS. 25-27, the magnitude |F| of force and angle of attack α may then be determined for exemplary contact sensing assembly 700.

Specifically, first the intensity $I_{01}$, $I_{02}$, $I_{03}$ at zero-force (e.g. force $\vec{F}=0$) may be measured. Thereafter, the intensity $I_1$, $I_2$, $I_3$ at force $\vec{F}>0$ at any angle of attack, e.g. α=0° to 90° may be measured. From these values, the Intensity change relative to zero-force may be calculated as follows:

$$I_{1r}=I_1-I_{01}$$

$$I_{2r}=I_2-I_{02}$$

$$I_{3r}=I_3-I_{03}$$

Thereafter, the resultant intensity $I_R$ may be calculated as follows: $I_R=(I_1+I_2+I_3)$, or $I_R=(I_{1r}+I_{2r}+I_{3r})$. The axial force $\vec{F}y$ may be obtained from the a priori regression curve of $\vec{F}y$ as a function of either $I_R=(I_1+I_2+I_3)$ or $I_R=(I_{1r}+I_{2r}+I_{3r})$. Thus axial force $\vec{F}y$ is:

$\vec{F}y=(I_R-a_{y0})/a_{y1}$, with $a_{y0}$ and $a_{y1}$ previously obtained as discussed above.

The minimum value between $I_{1r}$, $I_{2r}$, and $I_{3r}$ may then be calculated (e.g. $Min(I_{1r},I_{2r},I_{3r})$).

The transverse force $\vec{F}x$ may also be obtained from the a priori regression curve of $\vec{F}x$ as a function of $Min(I_{1r},I_{2r},I_{3r})$. Thus transverse force $\vec{F}x$ is:

$\vec{F}x=[Min(I_{1r},I_{2r},I_{3r})-a_{x0}]/a_{x1}$, with $a_{x0}$ and $a_{x1}$ previously obtained as discussed above From the axial and transverse components of force, the force |F| may be calculated as follows:

$$|F|=[\vec{F}x^2+\vec{F}y^2]^{1/2}$$

The angle of attack α may be calculated as follows:

$$\alpha=\arctan(\vec{F}y/\vec{F}x)$$

With the magnitude of force |F| and angle of attack α calculated as discussed above, the algorithm for calculating the angle of rotation θ will be discussed.

Figure 28:
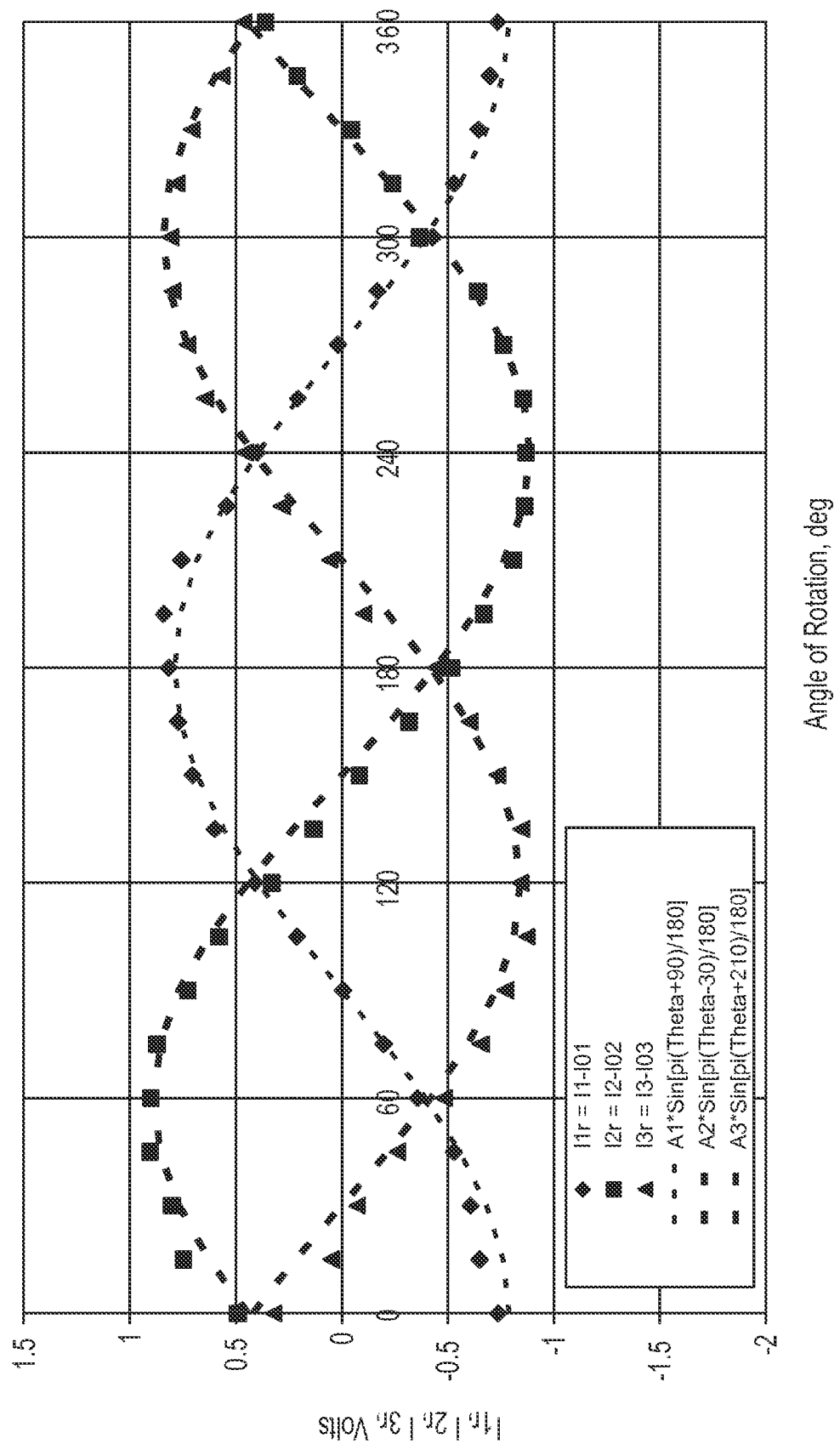
FIG. 28 is a graph of intensity variation with angle of rotation.

At any Force $\vec{F}$, and at any angle of attack α, the intensity values for the three Sensors (e.g. Sensor 1, Sensor 2 and Sensor 3, as discussed above), $I_1$, $I_2$, and $I_3$ as well as $I_{1r}$, $I_{2r}$, and $I_{3r}$, undergo sinusoidal variations with the rotation of a catheter around its own axis as shown in FIG. 28. Note, for the example given, each Sensor (e.g. Sensor 1, Sensor 2 and Sensor 3) may be disposed 120° apart.

Thus:

$$I_1=I_{01}+A_1\sin(\theta+\Phi_1), \text{ or } I_{1r}=A_1\sin(\theta+\Phi_1)$$

$$I_2=I_{02}+A_2\sin(\theta+\Phi_1+\Phi_{12}), \text{ or } I_{2r}=A_2\sin(\theta+\Phi_1+\Phi_{12})$$

$$I_3=I_{03}+A_3\sin(\theta+\Phi_1+\Phi_{13}), \text{ or } I_{3r}=A_3\sin(\theta+\Phi_1+\Phi_{13})$$

$\Phi_1$ is the phase angle of Sensor 1 at angle of rotation θ=0 ($\Phi_1$=90° in FIG. 28).

$\Phi_{12}$ is the phase angle difference between Sensor 1 and Sensor 2 ($\Phi_{12}$=−120° in FIG. 28).

$\Phi_{13}$ is the phase angle difference between Sensor 1 and Sensor 3 ($\Phi_{13}$=120° in FIG. 28).

For the above equations, $A_1$, $A_2$, and $A_3$ depend on the sensitivity of the Sensors (e.g. Sensor 1, Sensor 2 and Sensor 3), in that when the sensitivity of the Sensors are matched such that $A_1=A_2=A_3$, then $I_{1r}$, $I_{2r}$, and $I_{3r}$ are related as follows:

$$I_{1r}+I_{2r}+I_{3r}=0, \text{ and}$$

Angle of rotation θ may be determined from $I_{1r}$, $I_{2r}$, and $I_{3r}$ as follows:

$$\theta=\arctan[(2I_{2r}+I_{1r})/(\sqrt{3}I_{1r})], \text{ or}$$

$$\theta=\arctan[(I_{3r}-I_{2r})/\{\sqrt{3}(I_{3r}+I_{2r})\}], \text{ or}$$

$$\theta=\arctan[-(2I_{3r}+I_{1r})/(\sqrt{3}I_{1r})]$$

Based on the discussion above, referring to FIG. 24, when contact sensing assembly 700 contacts a surface, such as compliant membrane 706, the resulting contact angle α (e.g. angle of attack), with the electrode tip rotating at an angle of rotation θ may be calculated as discussed above after a sensor is calibrated as also discussed above. Likewise, the contact force vector $\vec{F}$ may be determined as a function of the axial component of force $\vec{F}y$ and the transverse component of force $\vec{F}x$ as also discussed above.

Figure 11A:
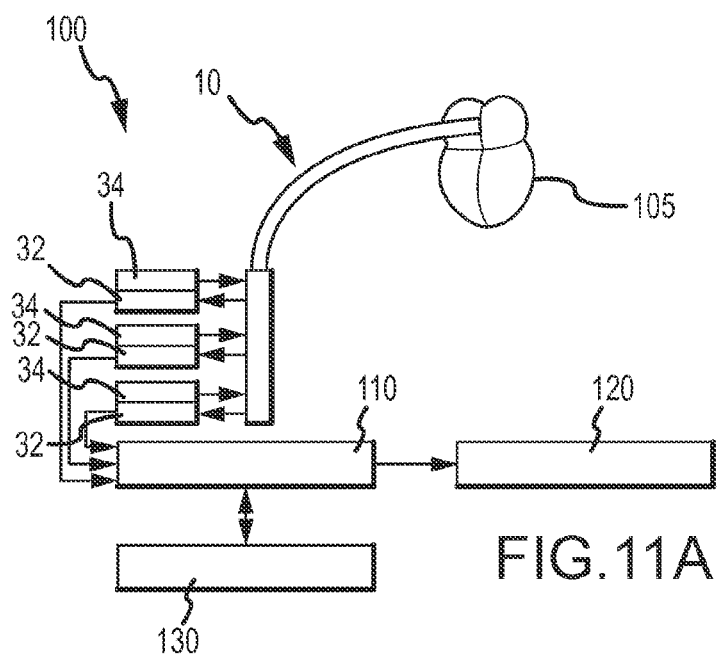
FIGS. 11A-11I are schematic overviews of the system in accordance with alternate embodiments of the invention.
Figure 11B:
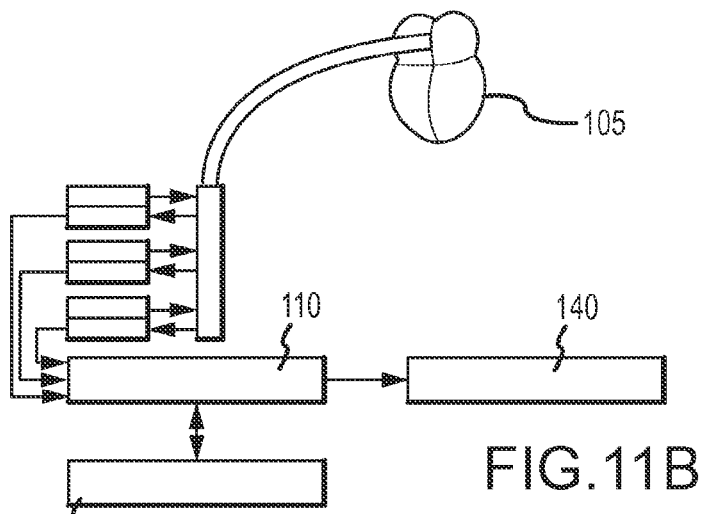
Figure 11C:
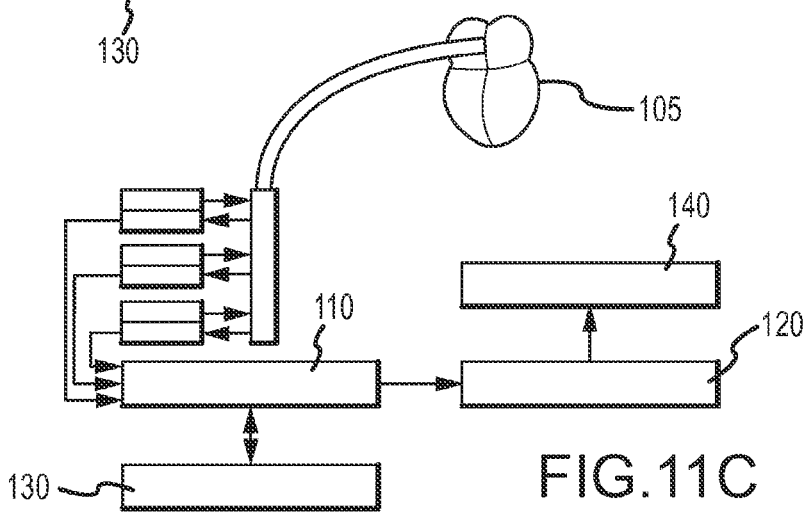
Figure 11D:
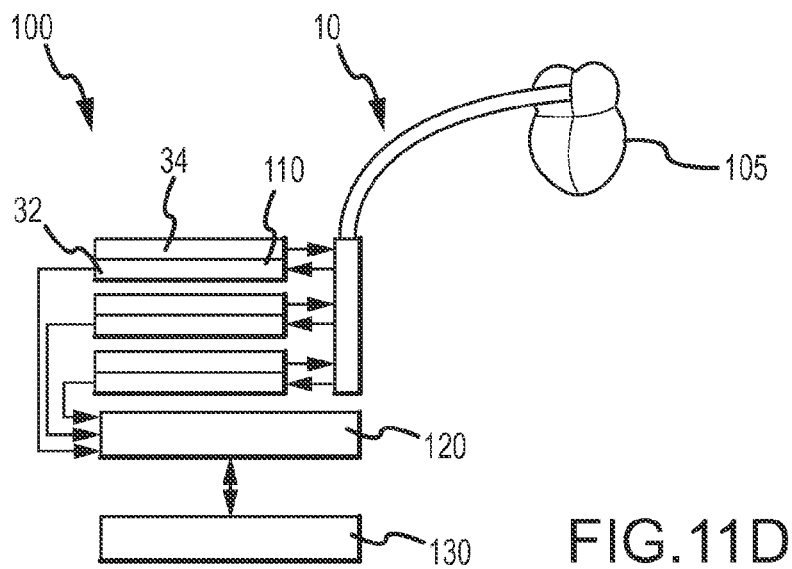
Figure 11E:
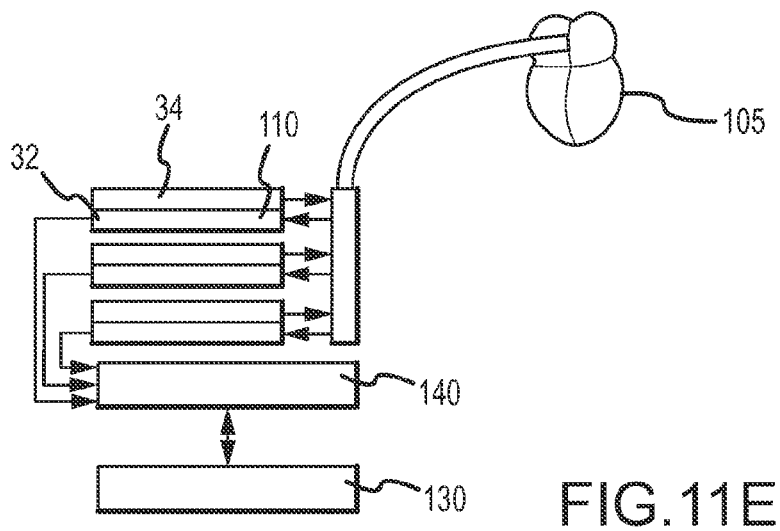
Figure 11F:
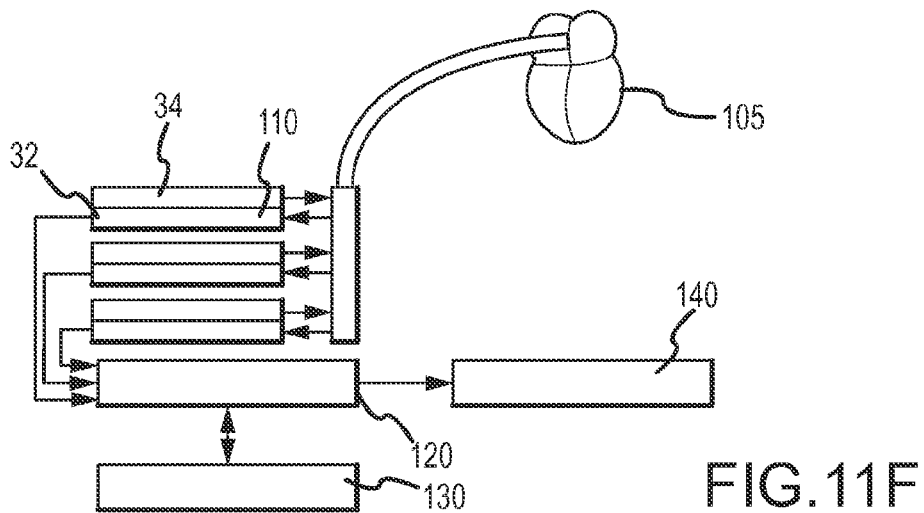
Figure 11G:
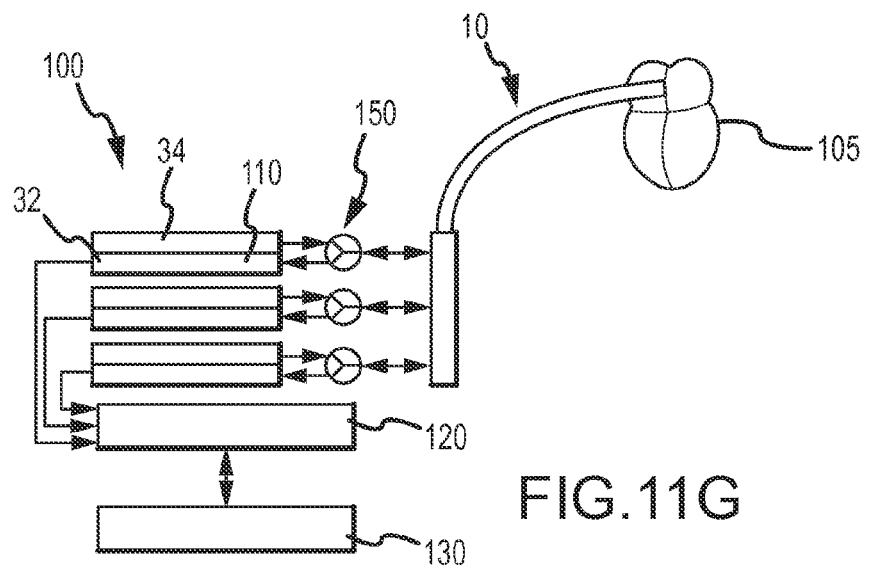
Figure 11H:
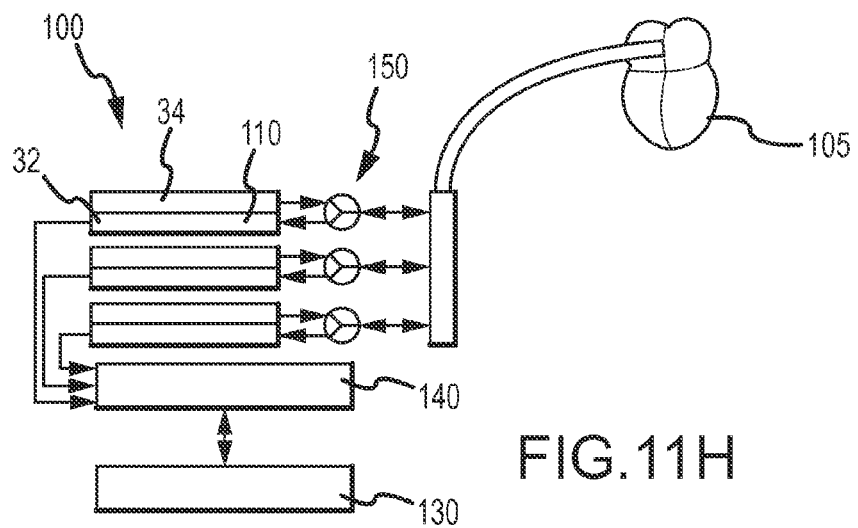
Figure 11I:
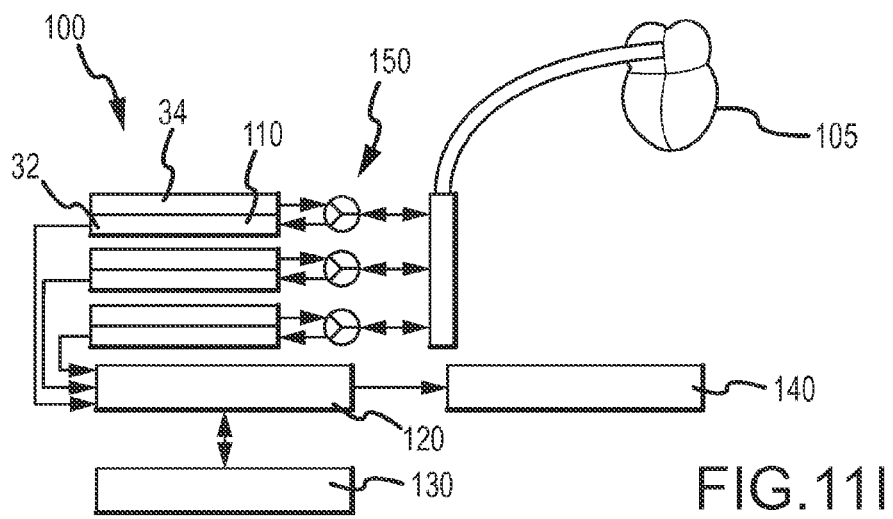

The invention further discloses an optic-based catheter system 100, as shown in FIGS. 11A-11F, that includes assembly 10 (and similarly assemblies of FIGS. 13A-23) of the invention connected to a signal converter 110 (such as an analog to digital converter) and an operator interface 120, which may further include a computer and display, for processing the optical signals received from assembly 10 in connection with positioning and contact with tissue, such as myocardial tissue 105. This optic-based information is processed to determine the contact force exerted on electrode 14 of assembly 10. A calibration system 130 (e.g., calibration software) may be further provided to readily correlate the amplitude or intensity of the received signal to the external force on the electrode. A mapping system 140, such as the system having the model name EnSite NavX™ and commercially available from St. Jude Medical, Inc., may be integrated with system 100 to provide a visualization and mapping system for use in connection with assembly 10 of the invention. In an alternate embodiment, as shown in FIGS. 11D-11F, the signal processor may be integrated with each of the receivers provided by optical sensor 16, such that the optical signal is directly processed and provided on the operator interface. Moreover, in another alternate embodiment, as shown in FIGS. 11G-11I, the emitter and receiver may use the same optical fiber for transmitting and receiving the optical signal. Accordingly a splitter 150, as known by one of ordinary skill in the art, may be used to manage the transmission and receiving of the optical signal for processing. Overall, each of these components may be modified and/or integrated with one another depending on the design of the optical system as recognized by one of ordinary skill in the art.

As previously described, the invention provides a method of sensing contact force and/or orientation as provided by the contact sensing assembly and system. The inventive method includes directing light or energy from a source through an optical sensor within a catheter; emitting light or energy from the optical sensor across a spaced gap for interacting with an optically-interactive surface provided in connection with an electrode; and receiving reflected light or energy by the optical sensor. The reflected light or energy may be processed by a processor to determine a change between the light or energy emitted from the optical sensor and the reflected light energy correspondingly received by the optical sensor. The changes may be correlated to, among other things, force vectors exerted by the electrode on a adjacent tissue.

In particular, under normal conditions of zero-contact force (e.g. when the electrode is not subjected to external forces), the plane of reflection as provided by either optically interactive surface 30, media 31 or medium 33, alone or in combination with one another as the case may be, is generally parallel to the plane of emitters 34 as previously described. Accordingly, the amplitude or intensity of the optical signal (e.g., light) received by receivers 32 is substantially the same or proportionally constant depending on the properties of the interactive surface. When the electrode contacts a surface, the contact force modifies the plane of reflection provided by the respective interactive surface (30, 31, or 33). In particular, upon the exertion of axial force ($F_a$) on the electrode, the plane of reflection is pushed closer to the place of emitters due to the spring-like configuration and/or flexibility exhibited by distal end 20 of catheter 12. Similarly, upon the exertion of lateral force ($F_1$), the plane of reflection is tilted with respect to the plane of emitters. The change in amplitude or intensity of the reflected optical signal (e.g. light) received by each of the receivers relative to one another results in the calculation of the lateral force exerted on the external surface of the electrode. The change in amplitude or intensity of the reflected light relative to the zero-axial-force condition can be used to determine the axial force being exerted on the electrode. As a result, the net contact force is given by the vector sum of the axial and lateral force, and the direction relative to the axis may be calculated. Overall, the force, either axial, lateral or a combination of both, is determined based on the change of intensity of the optical signal received by the receivers which is proportional to the displacement and/or movement of the distal end 20 of catheter 12.

The invention also provides a contact sensing assembly (see FIGS. 13A-23 and general discussion above) including a catheter including a body having a proximal end and a distal end, and an electrode including a tip portion and a base portion, and a generally central axis, with a portion of the electrode being connected to the distal end of the catheter. One or more optical sensors may be provided for emitting and/or receiving an optical signal, with a part of the optical signal being transverse to the central axis. The optical sensor may be operatively connected to the electrode or the catheter body. One or more optical interference members may be operatively connected to the electrode or the catheter body for interfering with the optical signal.

During manufacturing or fabrication of the contact sensing assemblies, such as those various embodiments described above, optic fibers may be positioned in connection within the base portion of the electrode and coupled to the coupling member for connection to a catheter shaft. One particular method of fabrication and aligning of the optical fibers, may include positioning the emitter/receiver into an assembly fixture such that the angle of the end portions of the fibers may be cleaved or cut to the desired angled (such as, for example, approximately 45 degrees). As previously suggested, the end portions of the emitter/receiver may further be partially or fully metalized, such as with a reflection-enhancing material, as recognized by those of ordinary skill in the art. Alternatively, the end portions of the optical fibers may be polished, such that an angle of approximately 45 degrees is obtained.

Figure 15B:
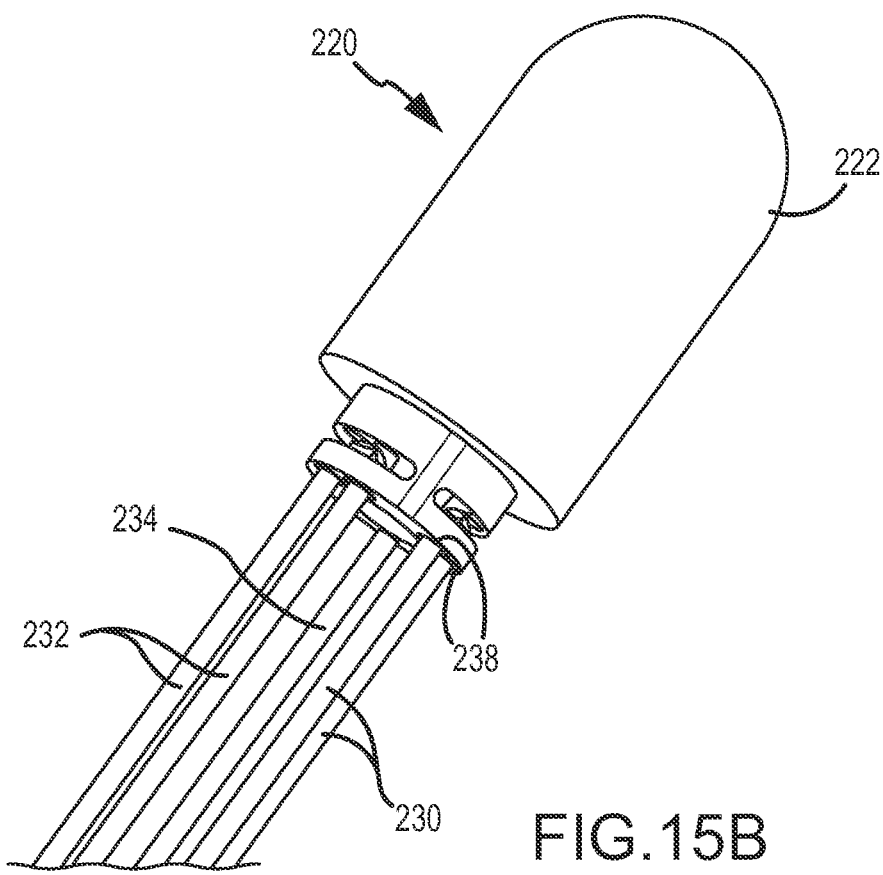
Figure 15C:
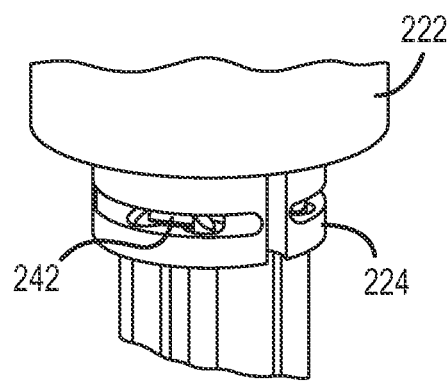
Figure 15D:
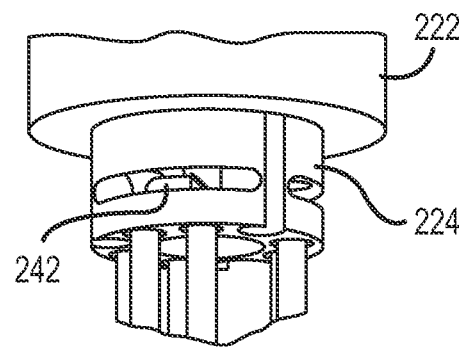

A number of various manufacturing or fabrication methods may be utilized in preparing the embodiments of the optical contact sensing assemblies of the present disclosure. With regards to one method of manufacturing, as previously discussed, the optical sensor having a proximal end and distal end is provided for incorporated within the contact assembly. As previously suggested, the optical sensor, includes an emitter and a receiver each having a distal and a proximal end, for emitting and receiving an optical signal. The end portions of the emitter and receiver may be provided at a desirable angle, such as, for example, approximately 45 degrees. In general, the distal end of the optical sensor is advanced towards the proximal end of an electrode. More specifically, the end portions of the emitter and receiver may be placed through the base portion of the electrode (such as seen in FIGS. 15A and 15B) through passages (i.e., 238) provided by the base portion of the electrode. The fibers may be advanced through the passages into the interior portion of the electrode tip towards the proximal end of the electrode. Once the optical sensor (i.e., emitter and receiver) is positioned within the electrode tip, the optical sensor is retracted from the proximal end of the electrode, such that the angled end portions of the optical sensor may be seen through an opening provided within the base portion of the electrode. In accordance with one embodiment, the emitter may be retracted and positioned relative to the base portion of the electrode and the receiver may be retracted and positioned relative to the base portion of the electrode. Specifically, the distal end of the emitter may be retracted from the proximal end of the electrode until at least the distal end is visible relative to the opening within the base portion of the electrode. Similarly, the distal end of the receiver may be retracted from the proximal end of the electrode until at least the distal end is visible relative to the opening within the base portion of the electrode. The angled end portions of the emitter and receiver may be aligned, such as for example, through the use of a scope or microscope. Following alignment of the distal end portions of the emitter and receiver, the proximal ends of the emitter and/or receiver may be covered through the use of a heat shrink material, such as, for example, a polymer based or polymer-like material. The material may be applied at a temperature of approximately 600° F. The heat shrink material may be positioned flush to the proximal end of the emitter and receiver through the use of a heat shrink type application. Once the material has cooled, the proximal ends of the emitter and receiver may be coupled to the amplifier. In particular, the emitter can be secured within a recess provided by the amplifier to perform the transmitting of signals. Similarly, the receiver may be secured within a recess provided by the amplifier for receiving signals. Upon connection of the emitter and/or receiver with the amplifier, the amplifier may be set to an initial power setting for preparing the alignment of the emitter and receiver in connection with one another vis-à-vis optical signals.

The alignment of the emitter and receiver in connection with one another may further include positioning the optical sensor within the base portion of the electrode by utilizing optical signals. In particular, the distal end of the emitter may be rotated until an optical signal is in contact with the receiver (such as, for example, a visible light is shinning at the receiver thereby indicating alignment). The receiver may then be rotated until a peak voltage is obtained from the amplifier. The peak voltage may be measured by a digital voltage meter, such that the receiver is rotated until a highest voltage meter reading is detected, such as for example, at least 3 Vdc. Once a peak voltage is obtained, the receiver may be secured in position, such as for example, by tightening a set screw or any other securing mechanism known by one of ordinary skill in the art. Similarly, the emitter may be rotated until a peak voltage is obtained, such that the digital voltage meter reading reaches its highest voltage level, such as for example, at least 3 Vdc. The emitter and receiver may then be advanced proximally and distally in relation to one another to detect a sensed voltage obtained by the amplifier. Furthermore, the emitter and receiver may be moved proximally or distally uniformally in relation to the base portion of the electrode to obtain a sensed voltage. The sensed voltage is preferably in the range of approximately 5.1 Vdc to approximately 5.2 Vdc. Once the sensed voltage is obtained and the approximately 50% of the angled end portions of the emitter and receiver are within the base portion of the electrode, the emitter and receiver (i.e., optical sensor) may be secured relative to the base portion of the electrode. In particular, an adhesive may be disposed within the opening of the base of the electrode for securing the optical sensor within the electrode. The adhesive may comprise an ultraviolet adhesive. Ultraviolet light may be provided to cure the adhesive. Alternately, other types of methods may be used to harden the adhesive. Once the emitter and receiver are secured within the base portion of the electrode, various distinguishing markings may be provided on the proximal ends of the receiver and emitter to distinguish the two. The optical sensor may then be released from any sort of assembly used during the process and the electrode may be rotated to another position for an additional optical sensor to be coupled to the electrode. In one embodiment, the process may be continued for a total of three optical sensors. The alignment of each of the fibers may be continued for each of the other pairs of the fibers for the contact sensing assembly, such as for example, fibers 230, 232, and 234, as shown in FIG. 15A. Alternatively, depending on the design of the optical assembly, various configurations and numbers of optical sensors may be provided in connection with the electrode.

The assembly may further be configured to include a reference structure. The reference structure may comprise acoustic, electromagnetic, optical, or any other type of structural elements capable of detecting and localizing the structure within the body, and hence the orientation of the catheter electrode relative to the body. One particular example of a reference structure, may include a fluoro-opaque marker. The fluoro-opaque marker may be provided as a coating on the surface of the assembly or integrated within the assembly (such as, for example, a coating or thin wire) having a known relationship to the optical sensors of the assembly and optionally to the directional irrigation ports. The reference marker may, in general, allow for visual rendering of the assembly through the use of a machine. Moreover, the sensor assembly may include other structural components and materials such as a magnetic material to enable sensing of the assembly through use in connection with various systems, such as, for example, and without limitation, the Carto™ System available from Biosense Webster, and as generally shown with reference to U.S. Pat. No. 6,498,944 entitled "Intrabody Measurement" and U.S. Pat. No. 6,788,967 entitled "Medical Diagnosis, Treatment and Imaging Systems," both of which are incorporated herein by reference in their entireties; commonly available fluoroscopy systems; or a magnetic location system, such as, for example, the gMPS system from MediGuide Ltd., and as generally shown with reference to U.S. Pat. No. 7,386,339 entitled "Medical Imaging and Navigation System," the disclosure of which is incorporated herein by reference in its entirety.

In another embodiment, the invention provides a method for sensing contact force exerted by an electrode on a tissue. The method may include directing an optical signal along at least a portion of a tubular body of a catheter having a proximal end and a distal end (see FIGS. 1-23 and general discussion above), and connecting an electrode including a tip portion and a base portion, and a generally central axis, to the distal end of the catheter. The method may further include emitting and/or receiving an optical signal, with at least a part of the optical signal being at a predetermined angle relative to the central axis, and sensing changes in intensity of the optical signal based on displacement associated with the electrode tip portion based on the contact force exerted by the electrode on the tissue.

An optical contact sensor assembly as disclosed may be further adapted to detect and quantify events that may occur either during or as a result of ablating tissue. Moreover, such an assembly may be adapted to detect and quantify, or sample, events (such as, for example, physiological events) at or during a discrete time interval, such as, for example a temporal duration ranging from approximately a few hundredths of a second to approximately sub-millisecond intervals. The events may be further detected within the frequency domain in a range from approximately 10 Hz to approximately 10 kHz. In general, many events may occur during the ablation of tissue. However, with some traditional systems and methods, such events may go undetected by an operator. In contrast, such events may be detected by manipulating the sensitivity of the sensor assembly. For instance, the sensitivity of the sensor assembly may be adjusted by manipulating at least one of the stiffness of the coupling member, the interference of the optical signal, the gain of the amplifiers, and the frequency of the acquired signal. Thus, due to the increased sensitivity of a sensor assembly of the type disclosed in connection with the present teachings, various sub-millisecond events may be recorded and identified. These events may include, but are not limited to, tissue pop, steam pop, identification of regions impacted by either tissue or steam pop, and any other type of event that may generate either an electrical or surface change in the region of interest as detected by the sensor assembly. For instance, changes in optical intensity associated with the contact of the sensor assembly, or the force readings recorded by the assembly, may be used as a basis for identifying events at a discrete level. These types of events, and all associated parameters (e.g., for example, power settings, irrigation levels, ablation settings, force, time/date, and relative location (3D or 4D location)) may be recorded and stored in the connection with known systems, such as the system having the model name EnSite NavX™ and commercially available from St. Jude Medical, Inc., or any other mapping and/or navigational system. Moreover, a robotic surgical system may collectively store the event information, as well as the associated parameters, and use such information to modifying the surgical procedure or relevant operational settings. Accordingly, the assembly may be coupled or integrated with a processor for processing the collected physiological signals. Moreover, the signals may be stored in a memory structure for further processing, reference, or collecting of the physiological signals. As suggested, various physiological signals may be processed and/or stored and collected, including but not limited to, the occurrence of, the spatial co-ordinates for, the ablation generator settings for, and the magnitude of the physiological signals.

Figure 35:
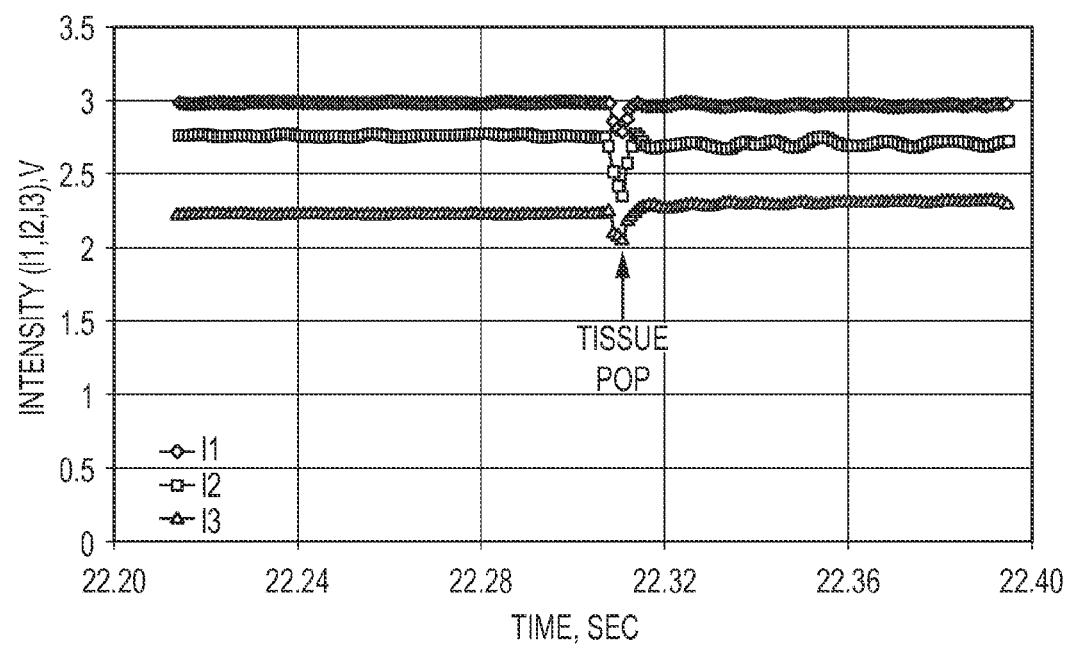
FIGS. 35-37 are graphs of 3-D force vector bench test and dynamic test results for the sensor test indicating tissue pop detection during operation of the assembly.
Figure 36:
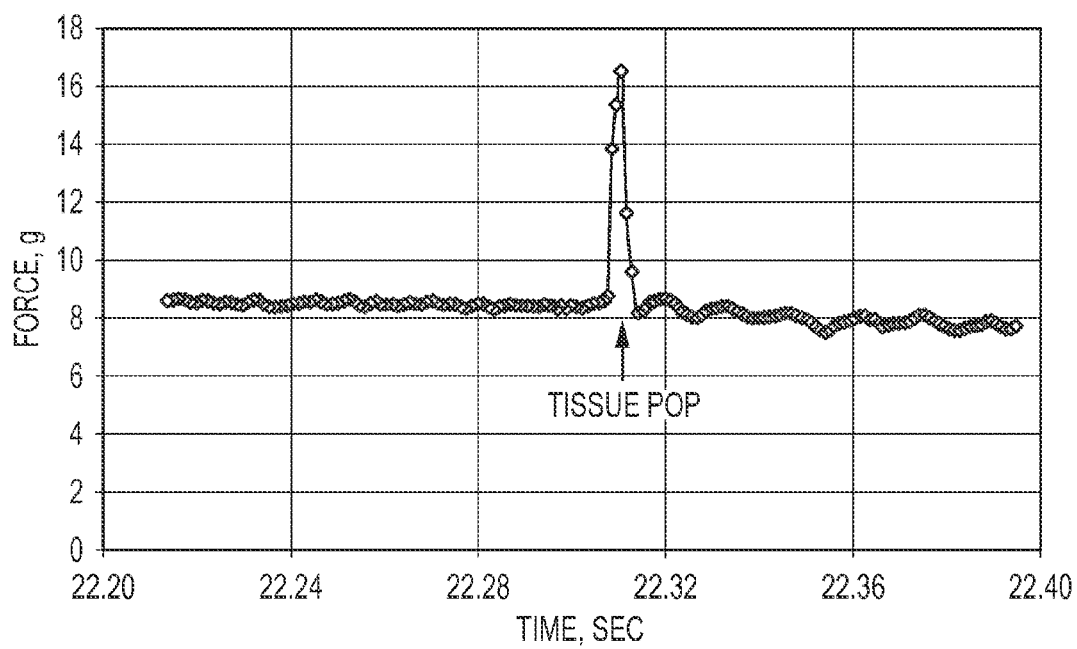
Figure 37:
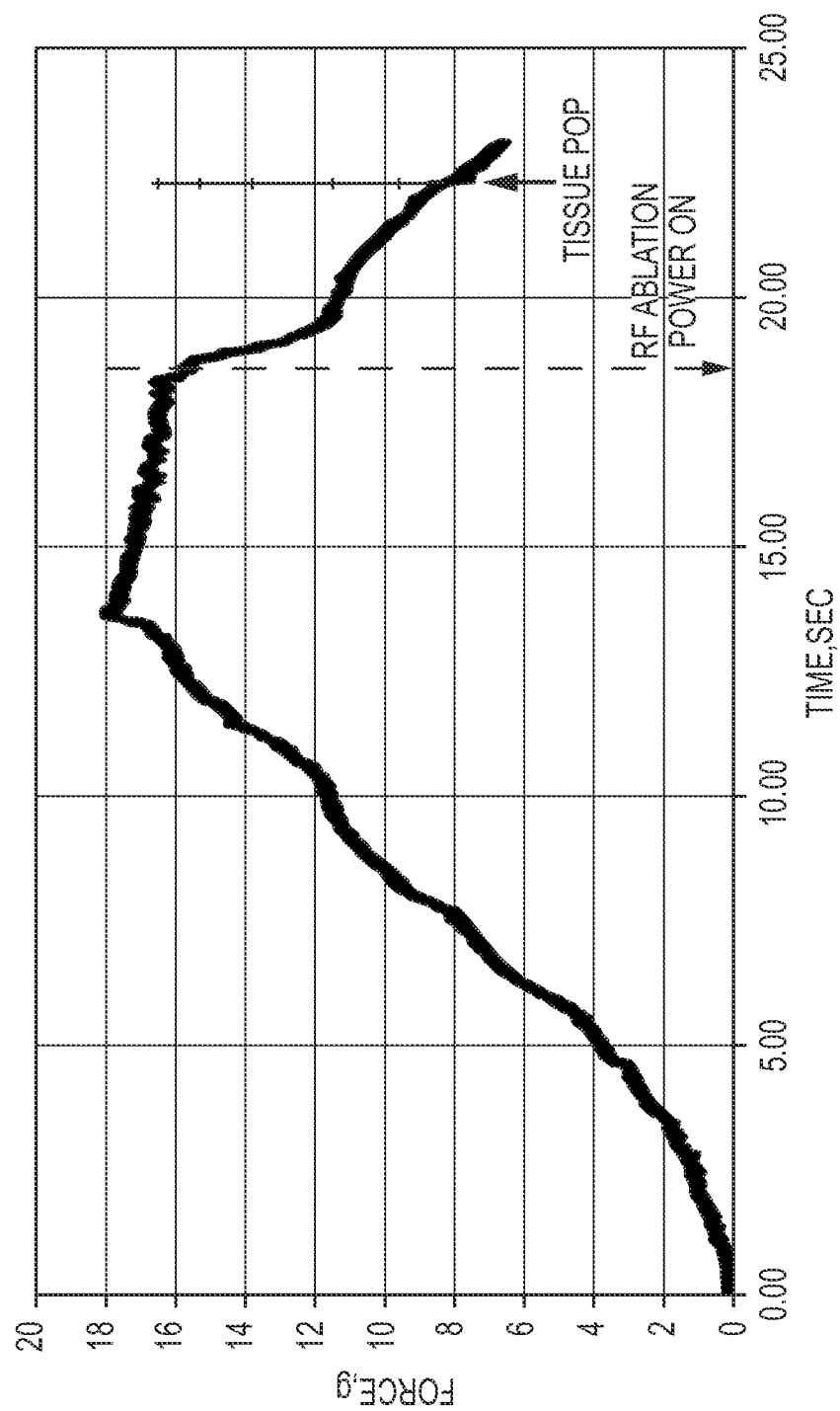

One particular event that may be detected at a sub-millisecond level is the instance of tissue pop during an ablation procedure, such as shown in FIGS. 35-37. In general, the event known as "tissue pop" more commonly occurs in RF and ultrasound ablation when the maximum temperature of the lesion occurs within the tissue. Accordingly, it may be desirable to configure the contact sensor assembly of the present disclosure to readily detect tissue that has been impacted by tissue pop, either during the actual ablation procedure or subsequent to the ablation procedure.

As shown in FIG. 35, the optical sensor assembly of the present invention provides three discrete intensity signals (I1, I2, and I3), each associated with the individual optical sensors provided by the assembly (such as, for example, 230, 232, and 234, as shown in FIG. 15A). Upon the occurrence of an event, such as tissue pop, intensity signals (I1, I2, and I3), may be recorded and a decrease in intensity, during a sub-millisecond interval, may be recorded in connection with each of the optical sensors. This uniform decrease in intensity can be reflective of tissue pop and, if desired, registered by the system. Moreover, as shown in FIG. 36, a corresponding change in force (g), such as a peak in the force readings, may be detected at the same time interval and is reflective of a tissue pop. Such a change a in peak force, with a subsequent return to baseline, may be reflective of an event (i.e., tissue pop) recorded by the optical sensor assembly.

Another embodiment, as shown in FIG. 37, further reflects a recording or logging of data generated by the optical sensor assembly, such as the force (g) resulting from the contact of the assembly with the tissue. The overall peak in force (as seen for example between 13-14 sec) may be generally reflective of the assembly coming in contact with the tissue. Following the initial contact of the assembly with tissue, a general decrease in force occurs which may be reflective of overall relaxation in the tissue. Upon the activation of the RF ablation power, a downward trend in force may be recorded therein reflective of the tissue undergoing ablation. During ablation, a distinct peak in force may be recorded. This distinct peak is reflective of an event, such as tissue pop, within the tissue during the ablation procedure. As previously suggested, this information may be recorded and ultimately used as a detection tool. The ability to log the location of the event and associated parameters may further be used to help identify future occurrences of the associated event or for the operator to take necessary steps to prevent the occurrence of the selected event.

As previously indicated, all embodiments of the present invention may be incorporated into a machine-based or robotically manipulated system, such as in a closed-loop control configuration.

The following numbered examples are set forth to provide a reader with additional context for a variety of exemplary embodiments of the teachings of the instant disclosure and are intended as illustrative and not limiting at to the breadth and scope of the teachings herein.

EXAMPLES

1. A contact sensing assembly including:
    a catheter including a body having a proximal end and a distal end;
    an electrode including a tip portion and a base portion, and a generally central axis, a portion of the electrode being connected to the distal end of the catheter;
    at least one optical sensor for at least one of emitting and receiving an optical signal, at least a part of the optical signal being transverse to the central axis, the optical sensor being operatively connected to one of the electrode and the catheter body; and
    at least one optical interference member operatively connected to one of the electrode and the catheter body for interfering with the optical signal.
2. An assembly according to example 1, wherein the optical sensor is configured to send and receive one of light energy and a light-based signal.
3. An assembly according to example 1, wherein the distal end of the catheter includes a coupling member having a neck portion.
4. An assembly according to example 3, wherein the neck portion of the coupling member moves relative to an external force exerted on the electrode.
5. An assembly according to example 3, wherein the neck portion of the coupling member includes one of a twist, torsion bar, alpha, dove-tail and spring shaped elastic portion for enabling external axial and transverse forces and torques exerted on the electrode to be sensed by the optical sensor.
6. An assembly according to example 3, wherein the coupling member includes a mounting shaft that defines an internal recessed groove for receiving at least a portion of the optical sensor.
7. An assembly according to example 1, wherein the tip portion of the electrode includes an irrigation port.
8. An assembly according to example 7, wherein a plurality of irrigation ports are disposed along a common axis on the tip portion of the electrode.

9. An assembly according to example 8, wherein the irrigation ports provide directional flow of irrigation fluid.
10. An assembly according to example 1, wherein the electrode includes a lumen provided within an internal cavity of the electrode, the lumen being positioned adjacent to the base and tip portions of the electrode.
11. An assembly according to example 1, wherein the optical sensor includes an emitter and a receiver for respectively emitting and receiving the optical signal.
12. An assembly according to example 11, wherein the emitter and receiver are provided with a single optic fiber.
13. An assembly according to example 11, wherein at least one of the emitter and receiver is positioned to respectively emit or receive the optical signal, a part of which is substantially parallel to the central axis.
14. An assembly according to example 13, further including a reflective surface for altering an angle of the optical signal substantially towards the optical interference member.
15. An assembly according to example 14, wherein the reflective surface is disposed on the emitter.
16. An assembly according to example 14, wherein the reflective surface in disposed on a fiber mirror arrangement.
17. An assembly according to example 11, wherein at least one of the emitter and receiver is positioned to respectively emit or receive the optical signal, the optical signal being substantially transverse to the central axis.
18. An assembly according to example 1, wherein the optical sensor includes at least one emitter and at least one radially positioned receiver for respectively emitting and receiving the optical signal.
19. An assembly according to example 18, wherein at least a part of the optical signal is substantially parallel to the central axis.
20. An assembly according to example 18, wherein the distal end of the catheter includes a coupling member having an elastic neck portion.
21. An assembly according to example 18, wherein the optical signal is substantially transverse to the central axis.
22. An assembly according to example 21, wherein the emitter and receiver are provided with a single optic fiber.
23. An assembly according to example 22, wherein the optical interference member is an appendage formed on the electrode base portion, the single optic fiber is disposed radially outboard of the appendage relative to the central axis.
24. An assembly according to example 22, wherein the optical interference member is an appendage formed on the electrode base portion, the single optic fiber is disposed radially inboard of the appendage relative to the central axis.
25. An assembly according to example 1, wherein the optical interference member is a structure formed on one of the electrode base portion and the catheter distal end.
26. An assembly according to example 1, wherein the optical interference member is an appendage formed on the electrode base portion.
27. An assembly according to example 26, wherein the appendage includes a cutout for allowing passage of a predetermined amount of the optical signal.
28. An assembly according to example 1, wherein the optical interference member is configured to interfere with the optical signal by respectively first and second predetermined amounts related to first and second predetermined positions of the electrode relative to the catheter body.
29. An assembly according to example 28, wherein the first predetermined amount of optical signal interference is zero interference.
30. An assembly according to example 28, wherein the first predetermined amount of optical signal interference is greater then zero interference.
31. An assembly according to example 1, wherein the optical sensor includes a fiber optic cable including at least one lumen and a peripheral wall surrounding the lumen, wherein the optical sensor is connected to the peripheral wall.
32. An assembly according to example 1, wherein a plurality optical sensors are disposed within the body of the catheter, each optical sensor having a means for emitting and receiving light energy.
33. An assembly according to example 32, wherein the optical sensors are circumferentially disposed within the body of the catheter.
34. An assembly according to example 1, wherein the optical sensor includes an emitter and a receiver for respectively emitting and receiving the optical signal, wherein the emitter and receiver are adjacent to one another and are paired.
35. An assembly according to example 1, wherein the optical sensor includes an emitter and a receiver for respectively emitting and receiving the optical signal, wherein a plurality of emitters and a plurality of receivers are distributed about a peripheral wall of a fiber optic cable such that each emitter operatively interacts with at least one receiver.
36. An assembly according to example 1, further including a lumen disposed within the body of the catheter, at least a portion of the lumen extending into the electrode for slidably receiving at least one sensing component.
37. An assembly according to example 1, further including a lumen disposed within the body of the catheter, at least a portion of the lumen extending into the electrode for slidably receiving at least one energizing component.
38. An assembly according to example 37, wherein the energizing component is selected from a radiofrequency current, direct current, high-intensity ultrasound, laser, cryogenic, and combinations thereof.
39. An assembly according to example 1, wherein the tip portion of the electrode includes a portion configured to perform ablation.
40. An assembly according to example 1, wherein the optical sensor is adapted to measure a parameter selected from the group consisting of intensity, wavelength, phase, spectrum, speed, optical path, interference, transmission, absorption, reflection, refraction, diffraction, polarization, and scattering.
41. An optical-based catheter system including:
 a catheter including a body having a proximal end and a distal end;
 an electrode including a tip portion and a base portion, and a generally central axis, a portion of the electrode being connected to the distal end of the catheter;
 at least one optical sensor for at least one of emitting and receiving an optical signal, at least a part of the optical signal being transverse to the central axis, the optical sensor being operatively connected to one of the electrode and the catheter body;
 at least one optical interference member operatively connected to one of the electrode and the catheter body for interfering with the optical signal; a light energy source;
 a processor; and a catheter mapping unit for use in mapping or visualizing the catheter location.
42. A system according to example 41, wherein the system determines a displacement associated with the electrode tip portion using sensed changes in intensity of the optical signal.
43. A system according to example 41, wherein the at least one optical sensor is adapted to measure a parameter selected from the group consisting of intensity, wavelength, phase, spectrum, speed, optical path, interference, transmission, absorption, reflection, refraction, diffraction, polarization, and scattering.
44. An assembly according to example 41, wherein the tip portion of the electrode includes an irrigation port.
45. An assembly according to example 44, wherein a plurality of irrigation ports are disposed along a common axis on the tip portion of the electrode.
46. An assembly according to example 45, wherein the irrigation ports provide directional flow of irrigation fluid.
47. A method for sensing contact force exerted by an electrode on a tissue including:
directing an optical signal along at least a portion of a tubular body of a catheter having a proximal end and a distal end;
connecting an electrode including a tip portion and a base portion, and a generally central axis, to the distal end of the catheter;
at least one of emitting and receiving an optical signal, at least a part of the optical signal being at a predetermined angle relative to the central axis; and
sensing changes in intensity of the optical signal responsive to displacement associated with the electrode tip portion based on the contact force exerted by the electrode on the tissue.
48. A method according to example 47, wherein the predetermined angle is approximately 0°.
49. A method according to example 47, wherein the predetermined angle is greater than approximately 0°.
50. A method according to example 47, further including determining corresponding contact force vectors between the electrode and the tissue in contact with the electrode by evaluating the sensed changes in intensity.
51. A method according to example 50, wherein the contact force vectors include an axial component of the contact force and a transverse component of the contact force.
52. A method according to example 51, further including calibrating an optical sensor that emits and receives the optical signal.
53. A method according to example 51, further including calibrating the optical sensors by measuring an intensity of the respective optical signal for each optical sensor at zero-force (I0x), measuring an intensity of the respective optical signal for each optical sensor at a force greater than zero (Ix), and determining the relative intensity (Irx) between Ix and I0x for each optical sensor as follows: Irx=Ix−I0x.
54. A method according to example 53, further including determining the axial and transverse components of contact force as a function of an angle of attack of the electrode relative to the tissue.
55. A method according to example 53, further including determining regression curves for the axial and transverse components of the contact force for a predetermined contact force range.
56. A method according to example 52, further including using the calibrated optical sensor to determine the axial and transverse components of the contact force.
57. A method according to example 56, further including determining the contact force magnitude as a function of the axial and transverse components of the contact force.
58. A method according to example 56, further including determining an angle of attack of the electrode relative to the tissue as a function of the axial and transverse components of the contact force.
59. A method according to example 56, further including determining an angle of rotation of the electrode relative to the tissue as a function of the change in intensity and phase angle of the optical sensor.
60. A method according to example 47, wherein the electrode performs one of RF ablation, HIFU ablation, laser ablation, cryo ablation, ultrasonic imaging, electrical pacing, EP pacing, electrical sensing, and EP sensing.
61. A method according to example 47, wherein the sensed contact force is utilized for at least one of:
a) automatically limiting a maximum contact force;
b) warning of a high or unacceptable contact force;
c) giving visual or audible feedback to a practitioner regarding a tissue contact force;
d) warning of a loss of contact force or contact; and
e) warning of a contact force which is too low.
62. A method of manufacturing an optical sensing assembly including:
providing an optical sensor having a proximal end and distal end, including an emitter and a receiver, each having a distal end and a proximal end, for respectively emitting and receiving an optical signal;
advancing the distal end of the optical sensor towards a proximal end of an electrode;
retracting the optical sensor from the proximal end of the electrode to dispose the distal end portion of the optical sensor within a base portion of the electrode;
coupling the proximal end of the optical sensor to an amplifier;
positioning the optical sensor within the base portion of the electrode by utilizing optical signals processed by the amplifier;
securing the optical sensor relative to the base portion of the electrode.
63. A method according to example 62, wherein retracting the optical sensor from the proximal end of the electrode includes:
retracting the emitter from the proximal end of the electrode until at least the distal end of the emitter is visible relative to an opening within a base portion of the electrode; and
retracting the receiver from the proximal end of the electrode until at least the distal end of the receiver is visible relative to an opening within a base portion of the electrode.
64. A method according to example 63, further including:
aligning the distal end of the emitter and receiver such that the end portions of the emitter and receiver are aligned with one another.
65. A method according to example 64, wherein the distal ends of the emitter and receiver include angled end surfaces.
66. A method according to example 62, wherein coupling the proximal end of the optical sensor to an amplifier includes the steps of:
connecting a proximal end of the emitter of the optical sensor to the amplifier; connecting a proximal end of the receiver of the optical sensor to the amplifier; and
providing power to the emitter and the receiver through the amplifier.

67. A method according to example 62, wherein positioning the optical sensor within the base portion of the electrode by utilizing optical signals includes:
rotating the distal end of the emitter until an optical signal is in contact with the receiver;
rotating the receiver fiber until a peak voltage level is obtained from the amplifier and secure the receiver fiber; and
rotating the emitter until a peak voltage level is obtained from the amplifier and secure the emitter.

68. A method according to example 67, wherein the peak voltage level is approximately 3 Vdc.

69. A method according to example 67, including:
advancing the emitter and receiver relative to each other proximally and distally to detect a sensed voltage level registered by the amplifier; and
securing the emitter and receiver upon obtaining the sensed voltage level.

70. A method according to example 69, wherein the sensed voltage level ranges from approximately 5.1 Vdc to approximately 5.2 Vdvc.

71. A method according to example 69, including advancing the emitter and receiver into the proximal end of the electrode until approximately 50% of the distal end of the emitter and receiver is in the electrode.

72. A method according to example 62, wherein securing the optical sensor relative to the base portion of the electrode further includes:
disposing adhesive within an opening within the base of the electrode for securing the optical sensor within the electrode.

73. A method according to example 72 wherein the adhesive comprises an ultraviolet adhesive.

74. A method according to example 72, including curing the adhesive with ultraviolet light.

75. A method according to example 62, wherein the method is utilized for a second optical sensor.

76. A method according to example 75, wherein the method is utilized for a third optical sensor.

77. A device for sampling discrete physiological events including:
an optical assembly including a catheter including a body having a proximal end and a distal end;
an electrode including a tip portion and a base portion, and a generally central axis, a portion of the electrode being connected to the distal end of the catheter; and
at least one optical sensor for at least one of emitting and receiving an optical signal, at least a part of the optical signal being transverse to the central axis, the optical sensor being operatively connected to one of the electrode and the catheter body;
wherein the optical assembly is adapted to sample physiological signals of a subject during a discrete temporal duration.

78. A device according example 77, wherein the sample of the discrete temporal duration ranges from approximately 10 Hz to approximately 10 kHz.

79. A device according to example 77, wherein the discrete temporal duration ranges from approximately a few hundredth of a second to approximately a sub-millisecond.

80. A device according to example 77, wherein An assembly is operatively coupled to a processor to process the physiological signals.

81. A device according to example 77, wherein the device includes a memory structure for storing at least one of: the number of, the occurrence of, the spatial coordinates for, the ablation generator settings for, and the magnitude of the physiological signals, respectively.

82. A device for sampling discrete physiological events including:
an optical assembly including a catheter including a body having a proximal end and a distal end;
an electrode including a tip portion and a base portion, and a generally central axis, a portion of the electrode being connected to the distal end of the catheter; and
at least one optical sensor for at least one of emitting and receiving an optical signal, at least a part of the optical signal being transverse to the central axis, the optical sensor being operatively connected to one of the electrode and the catheter body;
a means for sampling physiological signals of a subject during a discrete temporal duration.

83. A device according to example 82, including a means for processing and storing data associated with the physiological signals.

Although a number of embodiments of this invention have been described above with a certain degree of particularity, those skilled in the art could make numerous alterations to the disclosed embodiments without departing from the spirit or scope of this invention. For example, all joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A contact sensing assembly comprising:
a catheter including a body having a proximal end, a distal end, and a longitudinal axis;
an electrode including a tip portion and a base portion, one of the tip portion and the base portion of the electrode being connected to the distal end of the catheter;
at least one optical sensor configured to emit and receive an optical signal along an optical path, at least a part of the optical path being transverse to the longitudinal axis, the optical sensor being operatively connected to one of the electrode and the catheter body; and
at least one optical interference member operatively connected to one of the electrode and the catheter body and configured for interfering with the transverse part of the optical path.

2. The assembly according to claim 1, wherein the distal end of the catheter includes a coupling member having a neck portion.

3. The assembly according to claim 2, wherein the neck portion of the coupling member moves relative to an external force exerted on the electrode.

4. The assembly according to claim 2, wherein the neck portion of the coupling member includes one of a twist, torsion bar, alpha, dove-tail and spring shaped elastic portion for enabling external axial and transverse forces and torques exerted on the electrode to be sensed by the optical sensor.

5. The assembly according to claim 2, wherein the coupling member includes a mounting shaft that defines an internal recessed groove for receiving at least a portion of the optical sensor.

6. The assembly according to claim 1, wherein the tip portion of the electrode includes an irrigation port.

7. The assembly according to claim 6, wherein a plurality of irrigation ports are disposed along a common axis on the tip portion of the electrode.

8. The assembly according to claim 1, wherein the optical sensor includes at least one emitter and at least one radially positioned receiver for respectively emitting and receiving the optical signal.

9. The assembly according to claim 8, wherein the distal end of the catheter includes a coupling member having an elastic neck portion.

10. The assembly according to claim 1, wherein the optical interference member is a structure formed on one of the electrode base portion and the catheter distal end.

11. The assembly according to claim 1, wherein the optical interference member is configured to interfere with the optical path by respectively first and second predetermined amounts related to first and second predetermined positions of the electrode relative to the catheter body.

12. The assembly according to claim 1, wherein a plurality of optical sensors are disposed within the body of the catheter, each optical sensor having a means for emitting and receiving light energy.

13. The assembly according to claim 12, wherein the optical sensors are circumferentially disposed within the body of the catheter.

14. The assembly according to claim 1, wherein the optical sensor includes an emitter and a receiver for respectively emitting and receiving the optical signal, wherein a plurality of emitters and a plurality of receivers are distributed about a peripheral wall of a fiber optic cable such that each emitter operatively interacts with at least one receiver.

15. The assembly according to claim 1, wherein the tip portion of the electrode includes a portion configured to perform ablation.

16. The assembly according to claim 1, wherein the optical sensor is adapted to measure a parameter selected from the group consisting of intensity, wavelength, phase, spectrum, speed, interference, transmission, absorption, reflection, refraction, diffraction, polarization, and scattering.

17. The assembly according to claim 1, further comprising a reflective surface arranged so that the optical signal is reflected by said reflective surface after being emitted and before being received by said optical sensor.

18. An optical-based catheter system comprising:
a catheter including a body having a proximal end, a distal end, and a longitudinal axis;
an electrode including a tip portion and a base portion, one of the tip portion and the base portion of the electrode being connected to the distal end of the catheter;
at least one optical sensor configured to emit and receive an optical signal along an optical path, at least a part of the optical path being transverse to the longitudinal axis, the optical sensor being operatively connected to one of the electrode and the catheter body;
at least one optical interference member operatively connected to one of the electrode and the catheter body and configured for interfering with the transverse part of the optical path;
a light energy source;
a processor; and
a catheter mapping unit for use in mapping or visualizing a location of the catheter.

19. The system according to claim 18, wherein the processor determines a displacement associated with the electrode tip portion using sensed changes in intensity of the optical signal.

20. The system according to claim 18, wherein the optical sensor is adapted to measure a parameter selected from the group consisting of intensity, wavelength, phase, spectrum, speed, interference, transmission, absorption, reflection, refraction, diffraction, polarization, and scattering.

21. The assembly according to claim 18, wherein the tip portion of the electrode includes an irrigation port.

22. An elongate medical device comprising:
an elongate shaft having a distal end portion and defining a longitudinal axis;
an electrode including a tip portion and a base portion, one of the tip portion and the base portion of the electrode being connected to the distal end portion of the elongate shaft;
an optical sensor, the optical sensor comprising an emitter configured to emit an optical signal along an optical path and a receiver configured to receive the optical signal, the optical sensor being operatively connected to one of the electrode and the elongate shaft; and
an appendage operatively connected to one of the electrode and the elongate shaft and arranged and configured so as to interfere with a part of the optical path that is transverse to the longitudinal axis.

23. The elongate medical device of claim 22, wherein the emitter is separate from the receiver.

24. The elongate medical device of claim 23, wherein the emitter is positioned radially from the receiver and emits the optical signal along a direct transverse path to the receiver.

25. The elongate medical device of claim 23, further comprising a reflective surface, wherein the emitter emits the optical signal to the reflective surface and the reflective surface directs the optical signal to the receiver.

26. The elongate medical device of claim 25, wherein the reflective surface comprises two reflective surfaces, wherein the optical path goes from the emitter to a first of the two reflective surfaces, then to a second of the two reflective surfaces, then to the receiver.

27. The elongate medical device of claim 26, wherein the transverse part of the optical path is from the first of the two reflective surfaces to the second of the two reflective surfaces.

28. The elongate medical device of claim 23, wherein the receiver comprises a plurality of separate receivers.

29. The elongate medical device of claim 28, wherein the plurality of separate receivers are positioned radially around the emitter.

30. The elongate medical device of claim 22, wherein the appendage moves longitudinally to interfere with a variable amount of the transverse part of the optical path as external forces on the electrode or catheter body change.

* * * * *